（12）United States Patent
Hatase et al.

(10) Patent No.: US 10,578,855 B2
(45) Date of Patent: Mar. 3, 2020

(54) ENDOSCOPE

(71) Applicant: Panasonic i-PRO Sensing Solutions Co., Ltd., Fukuoka (JP)

(72) Inventors: Yuichi Hatase, Fukuoka (JP); Naoyuki Haraguchi, Saga (JP); Satoru Miyanishi, Fukuoka (JP); Takafumi Sanada, Fukuoka (JP)

(73) Assignee: Panasonic i-PRO Sensing Solutions Co., Ltd., Fukuoka (JP)

( * ) Notice: Subject to any disclaimer, the term of this patent is extended or adjusted under 35 U.S.C. 154(b) by 0 days.

(21) Appl. No.: 15/492,220

(22) Filed: Apr. 20, 2017

(65) Prior Publication Data

US 2017/0307872 A1 Oct. 26, 2017

(30) Foreign Application Priority Data

Apr. 25, 2016 (JP) ................. 2016-087487
Apr. 25, 2016 (JP) ................. 2016-087488
Apr. 25, 2016 (JP) ................. 2016-087491

(51) Int. Cl.
*A61B 1/06* (2006.01)
*G02B 23/24* (2006.01)
*A61B 1/00* (2006.01)
*A61B 1/04* (2006.01)
(Continued)

(52) U.S. Cl.
CPC ...... *G02B 23/2469* (2013.01); *A61B 1/00009* (2013.01); *A61B 1/00137* (2013.01); *A61B 1/04* (2013.01); *A61B 1/06* (2013.01); *A61B 1/0661* (2013.01); *A61B 1/0676* (2013.01); *A61B 1/0684* (2013.01); *A61B 1/0692* (2013.01); *G02B 7/02* (2013.01); *G02B 23/243* (2013.01); *G02B 23/2484* (2013.01); *H04N 5/2256* (2013.01); *A61B 2562/18* (2013.01);
(Continued)

(58) Field of Classification Search
CPC .... G02B 23/2469; G02B 7/02; G02B 23/243; G02B 23/2484; G02B 23/24; A61B 1/00009; A61B 1/00137; A61B 1/04; A61B 1/06; A61B 1/00117; A61B 1/0661; A61B 1/0676; A61B 2562/18; A61B 2562/185; H04N 5/2256; H04N 2005/2255
See application file for complete search history.

(56) References Cited

U.S. PATENT DOCUMENTS 5,569,162 A * 10/1996 Komi ................. A61B 1/00098
600/129
5,868,664 A * 2/1999 Speier ..................... A61B 1/042
348/73

(Continued)

FOREIGN PATENT DOCUMENTS

DE 10 2016 216 380 A1 3/2017
EP 1 371 321 A1 12/2003
JP 2008-212309 A 9/2008

*Primary Examiner* — Robert J Hance
(74) *Attorney, Agent, or Firm* — Seed IP Law Group LLP

(57) ABSTRACT

A lens having a quadrangular outer shape in a direction perpendicular to its center, an imaging element having a quadrangular outer shape in the direction perpendicular to the center axis, an element cover glass covering an imaging surface of the imaging element, a light guide placed outside at least one side of the lens and extending along the center axis, and a cylinder holder disposed between the lens and the light guide are disposed in a tip portion of an endoscope.

8 Claims, 36 Drawing Sheets

(51) Int. Cl.
*G02B 7/02* (2006.01)
*H04N 5/225* (2006.01)

(52) U.S. Cl.
CPC .............................. *A61B 2562/185* (2013.01); *H04N 2005/2255* (2013.01)

(56) References Cited

U.S. PATENT DOCUMENTS

| | | | | |
|---|---|---|---|---|
| 6,080,101 | A * | 6/2000 | Tatsuno | A61B 1/00124 348/65 |
| 6,387,044 | B1 * | 5/2002 | Tachibana | A61B 1/00135 600/114 |
| 2007/0046778 | A1 * | 3/2007 | Ishihara | A61B 1/00009 348/68 |
| 2010/0286475 | A1 * | 11/2010 | Robertson | A61B 1/00096 600/104 |
| 2012/0190990 | A1 * | 7/2012 | Ohzawa | G02B 23/2469 600/478 |
| 2014/0316199 | A1 * | 10/2014 | Kucklick | A61B 1/317 600/109 |
| 2015/0164313 | A1 * | 6/2015 | Ouyang | A61B 1/00103 600/103 |
| 2017/0059848 | A1 | 3/2017 | Haraguchi et al. | |

\* cited by examiner

ENDOSCOPE

CROSS REFERENCE TO RELATED APPLICATIONS

This application is based on Japanese Patent Applications (Nos. 2016-087491, 2016-087488, 2016-087487) filed on Apr. 25, 2016, the contents of which are incorporated herein by reference.

BACKGROUND OF THE INVENTION

1. Field of the Invention

The present disclosure relates to an endoscope.

2. Description of the Related Art

In the related art, a small-diameter endoscope that has a diameter of less than 3 mm is known as illustrated in FIGS. 46 and 47 (refer to, for example, JP-A-2008-212309). FIG. 46 is a front view of a tip portion of a small-diameter electronic endoscope according to the related art. FIG. 47 is a perspective view of a light guide fiber bundle unit in the tip portion of the small-diameter electronic endoscope. In the small-diameter endoscope according to JP-A-2008-212309, an outer periphery of an observation window 501 is fitted into an insulating tube 503 and a tip portion main body inner tube 505 is placed on an outer periphery of the insulating tube 503. An outer edge of the tip portion main body inner tube 505 is scraped off in accordance with the shape of the chord of an injection end face 507 and an injection end portion of a light guide fiber bundle 509 illustrated in FIG. 47 is inserted into a space between a tip portion main body outer tube 511 and the tip portion main body inner tube 505 in a filled state. Three regions are formed in the light guide fiber bundle 509, that is, a hard molded portion 513 as a unit with which a space in the tip portion main body outer tube 511 is filled, the hard molded portion 513 being hardened by an adhesive in the shape of the space, a flexible portion 517 inserted into and placed in an insertion portion in a state where the flexible portion 517 is coated with a flexible protective tube 515, and a transition portion 519 between the hard molded portion 513 and the flexible portion 517.

In the configuration of the small-diameter endoscope according to JP-A-2008-212309, lighting member such as the light guide fiber bundle 509 is placed around an objective optical system (that is, a circular lens) and the observation window 501 having a circular shape. Accordingly, the outer diameter of the endoscope increases to that extent. The configuration in which the lighting member is placed around the circular lens results in a useless space in an insertion tip surface. Then, member placement density cannot be increased in the insertion tip surface. In other words, a low level of space efficiency arises, which results in disadvantages in terms of endoscope size reduction. In addition, it is difficult to stably fix the circular lens and a quadrangular imaging element. Furthermore, it is difficult to reduce the size of the light guide fiber bundle 509 because the light guide fiber bundle 509 is obtained by multiple bare fiber strands being bundled up by being hardened by a low-viscosity adhesive and, as such, the area of its outer periphery increases and leaking light is likely to move into the imaging element. This leaking light becomes stray light in the optical system that leads to image quality deterioration.

SUMMARY OF THE INVENTION

The present disclosure has been made in view of the above-described circumstances, and an object thereof is to provide an endoscope with which stray light from lighting member can be prevented with high-strength fixing of a lens and an imaging element facilitated and size reduction ensured by a useless space being suppressed based on an increase in space efficiency in an insertion tip surface.

The present disclosure provides an endoscope provided with a lens that has a quadrangular outer shape in a direction perpendicular to a center axis of the lens, an imaging element that has a quadrangular outer shape in the direction perpendicular to the center axis, an element cover glass configured to cover an imaging surface of the imaging element, a lighting member that is disposed outside at least one side of the lens and extends along the center axis, and a light-shielding member that is disposed between the lens and the lighting member.

According to the present disclosure, stray light from the lighting member can be prevented, high-strength fixing of the lens and the imaging element can be facilitated, and size reduction is ensured by space efficiency (that is, member placement density) improvement (that is, suppression of a useless space) being allowed in an insertion tip surface.

BRIEF DESCRIPTION OF THE DRAWINGS

FIG. 37 is a perspective view in which the sheath of the endoscope illustrated in FIG. 36 is seen through.

FIG. 40 is a perspective view in which the sheath of the endoscope illustrated in FIG. 39 is seen through.

DETAILED DESCRIPTION OF THE PREFERRED EMBODIMENTS

An embodiment (hereinafter, referred to as "the present embodiment") that specifically discloses an endoscope according to the present invention will be described in detail below with reference to accompanying drawings with excessively detailed description omitted in some cases. Examples of the excessively detailed description include detailed description of matters that are already well known and repetitive description of configurations that are substantially identical to each other. This is to avoid a long and tedious description and allow those skilled in the art to better understand the following description. The accompanying drawings and the following description are for those skilled in the art to sufficiently understand the present disclosure, and the subject matter described in the scope of claims is not limited by the accompanying drawings and the following description.

A basic configuration example common to the endoscope according to the present embodiment will be described first. Configuration examples refer to configuration requirements that the endoscope according to the present invention can be provided with. It is not ruled out that the endoscope according to the present invention is provided with the following respective configuration examples in an overlapping manner.

Basic Configuration Example

Figure 1:
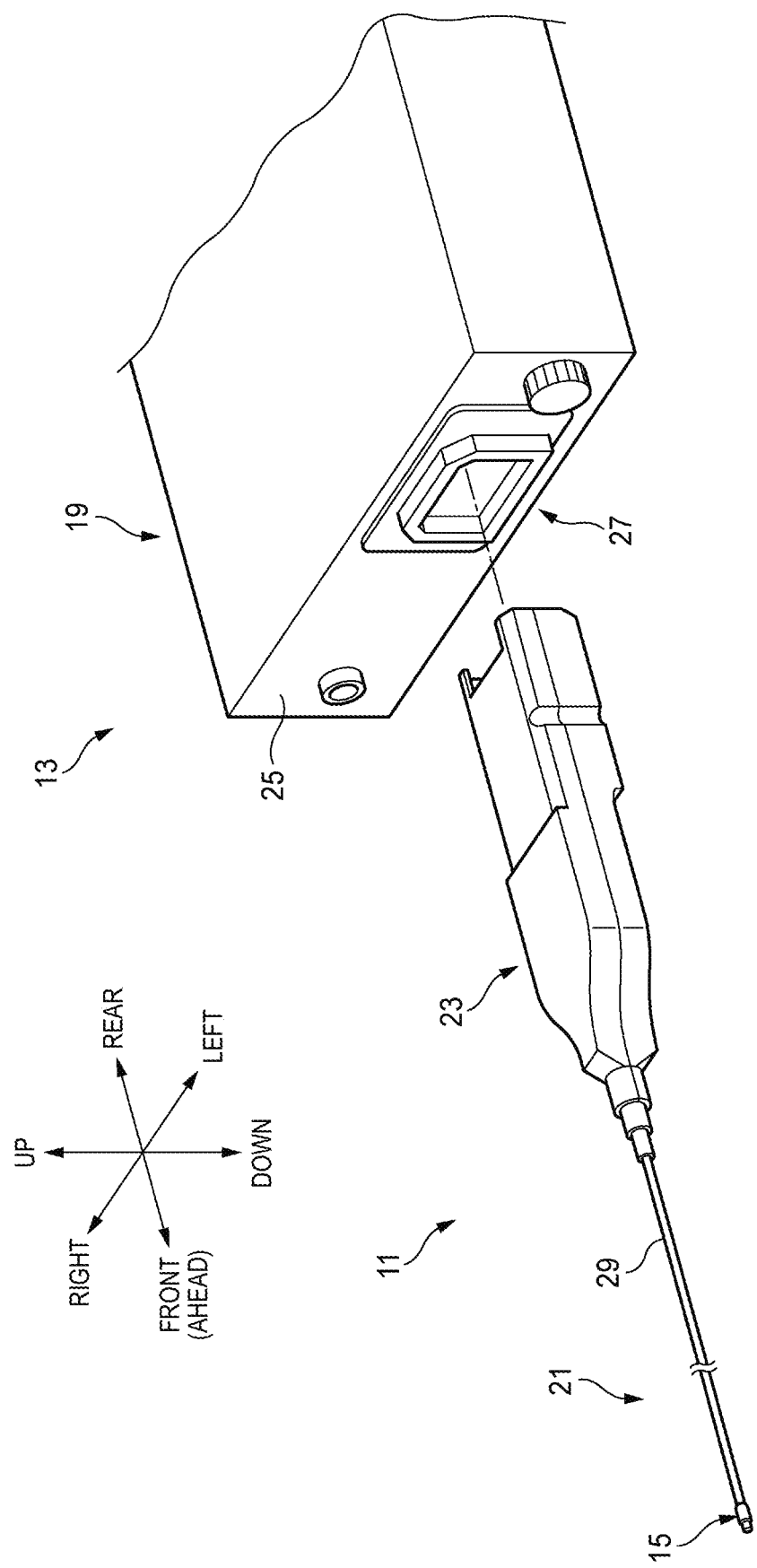
FIG. 1 is an overall configuration diagram illustrating an example of an endoscope system using an endoscope according to the present embodiment.

FIG. 1 is an overall configuration diagram illustrating an example of an endoscope system using the endoscope according to the present embodiment. An overall configuration of an endoscope system 13 including an endoscope 11 and a video processor 19 is illustrated in FIG. 1, which is a perspective view.

Directions used for the description in the present specification follow the illustration of directions in each of the drawings. In the illustration, "up" and "down" correspond to above and below the video processor 19 placed on a horizontal plate, respectively. "Front (ahead)" and "rear" correspond to a tip side of an insertion portion 21 of an endoscope main body (hereinafter, referred to as the "endoscope 11") and a base end side of a plug portion 23 (that is, the video processor 19 side), respectively.

As illustrated in FIG. 1, the endoscope system 13 is configured to include the endoscope 11 and the video processor 19. The endoscope 11 is, for example, a flexible mirror for medical use. The video processor 19 performs known image processing or the like on a still image or a moving image that is obtained by imaging of an inner portion of an object of observation (such as a blood vessel in a human body). The endoscope 11 is provided with the insertion portion 21 and the plug portion 23. The insertion portion 21 extends substantially in a front-rear direction and is inserted into the inner portion of the object of observation. A rear portion of the insertion portion 21 is connected to the plug portion 23.

The video processor 19 has a socket portion 27 that is open to a front wall 25. A rear portion of the plug portion 23 of the endoscope 11 is inserted into the socket portion 27. This insertion allows the endoscope 11 to send and receive electric power and various signals (such as a video signal and a control signal) to and from the video processor 19.

The electric power and the various signals described above are guided from the plug portion 23 to a soft portion 29 via a transmission cable 31 (refer to FIG. 3 or FIG. 4) inserted into an inner portion of the soft portion 29. Image data output by an imaging element 33 disposed in a tip portion 15 is transmitted from the plug portion 23 to the video processor 19 via the transmission cable 31. The video processor 19 performs the known image processing, such as color correction and tone correction, on the image data transmitted from the plug portion 23 and outputs the image-processed image data to a display device (not illustrated). The display device is a monitor device that has a display device such as a liquid crystal display panel and displays an image of a subject imaged by the endoscope 11 (such as image data showing an appearance inside a blood vessel of a person who is the subject).

The insertion portion 21 has the flexible soft portion 29 of which a rear end is connected to the plug portion 23, and the tip portion 15 that leads to a tip of the soft portion 29. The soft portion 29 has an appropriate length responding to various types of endoscopy, endoscopic operations, and the like. Coating performed on an outer periphery of a net covering an outer periphery of a spirally wound metal sheet is an example of what constitutes the soft portion 29 and the soft portion 29 is formed to have a sufficient level of flexibility. The soft portion 29 provides connection between the tip portion 15 and the plug portion 23.

The endoscope 11 according to the embodiment that is to be described below can be inserted into body cavities that have small diameters because the insertion portion 21 is formed to have a small diameter. The small-diameter body cavities are not limited to blood vessels in human bodies and include, for example, the ureter, pancreatic duct, bile duct, and bronchioles. In other words, the endoscope 11 is capable of allowing insertion into blood vessels, ureters, pancreatic ducts, bile ducts, bronchioles, and the like in human bodies.

In other words, lesions in blood vessels can be observed with the endoscope 11. The endoscope 11 is effective for arteriosclerotic plaque identification and can also be applied to endoscope-based observation during cardiac catheter tests. Furthermore, the endoscope 11 is effective for thrombus and arteriosclerotic yellow plaque detection. In arteriosclerotic lesions, color tones (white, light yellow, and yellow) and surfaces (smooth and irregular) are observed. In the thrombus, color tones (red, white, dark red, yellow, brown, and mixed) are observed.

The endoscope 11 can be used for diagnosis and treatment of renal pelvic and ureteral cancers and idiopathic renal bleeding as well. In this case, the endoscope 11 is inserted from the urethra into the bladder and then is moved into the ureter. Then, the insides of the ureter and the renal pelvis can be observed.

The endoscope 11 can be inserted into Vater's papilla open to the duodenum, too. Bile is produced in the liver and discharged from Vater's papilla in the duodenum through the bile duct and pancreatic juice is produced in the pancreas and discharged from Vater's papilla in the duodenum through the pancreatic duct. The endoscope 11 is capable of allowing bile duct or pancreatic duct observation by being inserted from Vater's papillae as opening portions in the bile and pancreatic ducts.

The endoscope 11 can be inserted into the bronchial tubes as well. The endoscope 11 is inserted from the oral cavity or nasal cavity of a specimen (that is, a subject undergoing a medical procedure) in a supine position. The endoscope 11 is inserted into the trachea, while viewing the vocal cords, past the pharynx and larynx. The bronchial tubes become thin every time they branch. With the endoscope 11 that has a maximum outer diameter Dmax of less than 2 mm, for example, lumen confirmation is possible to the point of subsegmental bronchi.

Hereinafter, the various configuration examples of the endoscope according to the present embodiment will be described. The endoscope 11 according to the present embodiment is capable of having each of the configurations ranging from first to twentieth configuration examples.

The term of "adhesive" in the following description is not limited to the strict sense of the word, that is, a substance used for adhesion between surfaces of solid matter. Instead, the term is used in a broad sense of the word, that is, a substance which can be used for bonding between two materials or, in a case where a cured adhesive has high barrier properties with respect to gas and liquid, a substance which has a function as a sealant.

First Configuration Example

Figure 2:
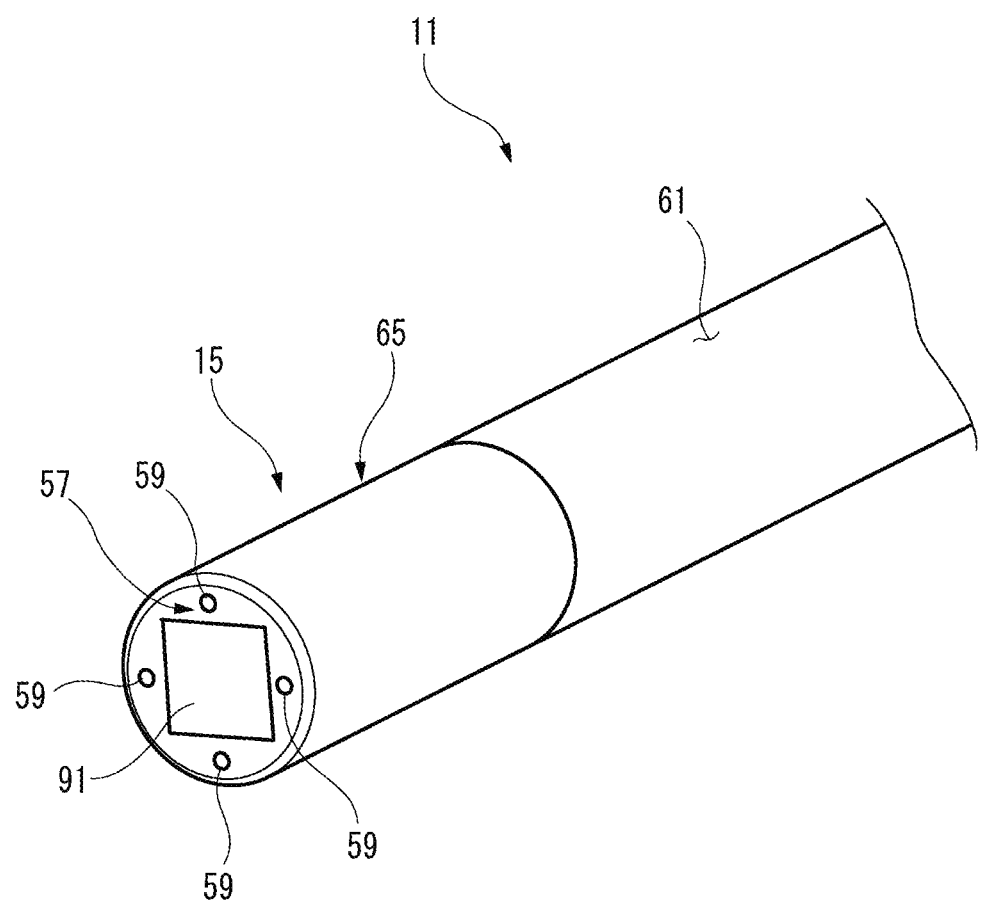
FIG. 2 is a perspective view illustrating an appearance of a tip portion of the endoscope according to the present embodiment that is seen from a front side.
Figure 3:
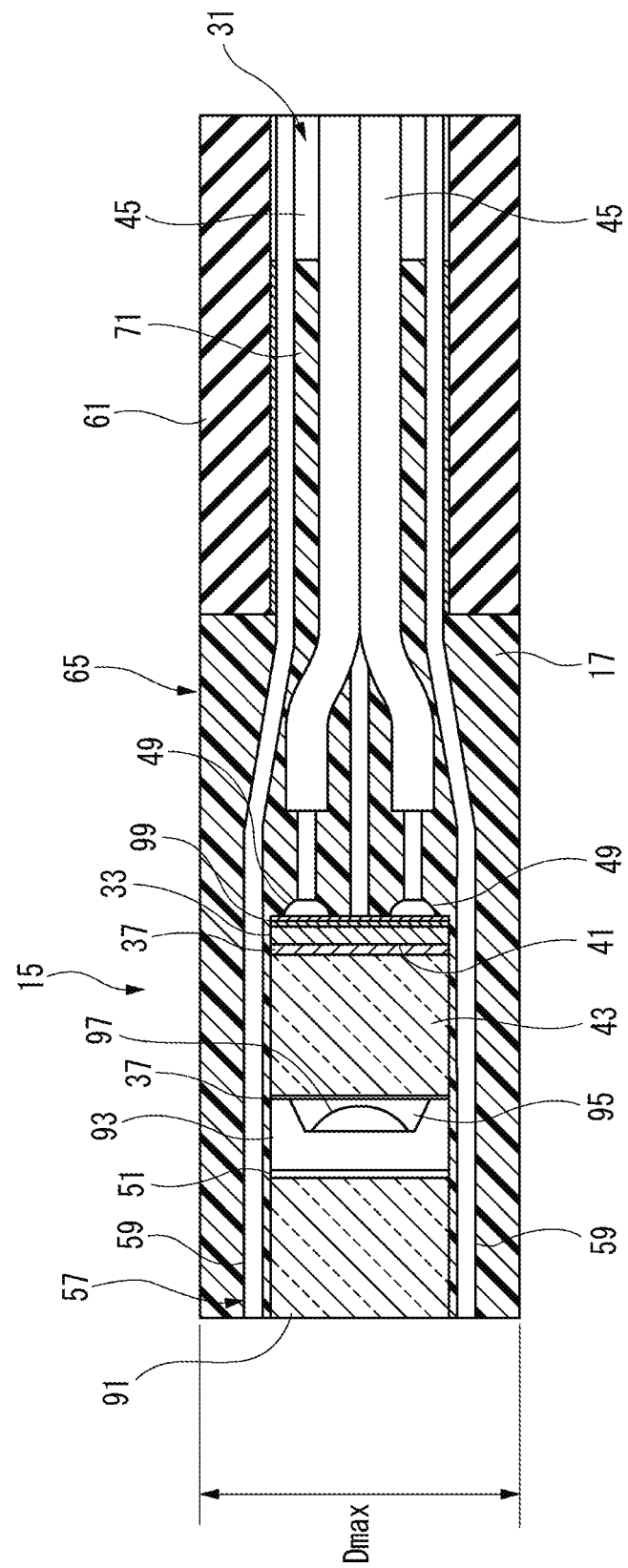
FIG. 3 is a sectional view illustrating a configuration example of the tip portion of the endoscope according to the present embodiment.

FIG. 2 is a perspective view illustrating an appearance of the tip portion 15 of the endoscope 11 according to the present embodiment that is seen from a front side. FIG. 3 is a sectional view illustrating a configuration example of the tip portion 15 of the endoscope 11 according to the present embodiment. In the endoscope 11 illustrated in FIG. 2, the maximum outer diameter Dmax of the tip portion 15 illustrated in FIG. 3 can be formed to have a range of a finite diameter to 1.0 mm, which is equivalent to the diameter of a circle circumscribed about a substrate of the imaging element 33 that can be diced.

In the endoscope 11 according to the present embodiment, an imaging element that has one side having a dimension of 0.5 mm or less is used as the imaging element 33 that has a square cross section in a direction perpendicular to the direction of an optical axis or an axial direction through a center of a lens (a center axis of the lens). Accordingly, the imaging element 33 has a diagonal dimension of approximately 0.7 mm in the endoscope 11, and the maximum outer diameter Dmax can be 1.0 mm or less with light guides 57 (for example, φ50 μm) as lighting member included.

As described above, the maximum outer diameter Dmax is less than 1.0 mm in the endoscope 11 according to the first configuration example, and thus insertion into, for example, the blood vessels in the human body can be further facilitated.

Second Configuration Example

Figure 5:
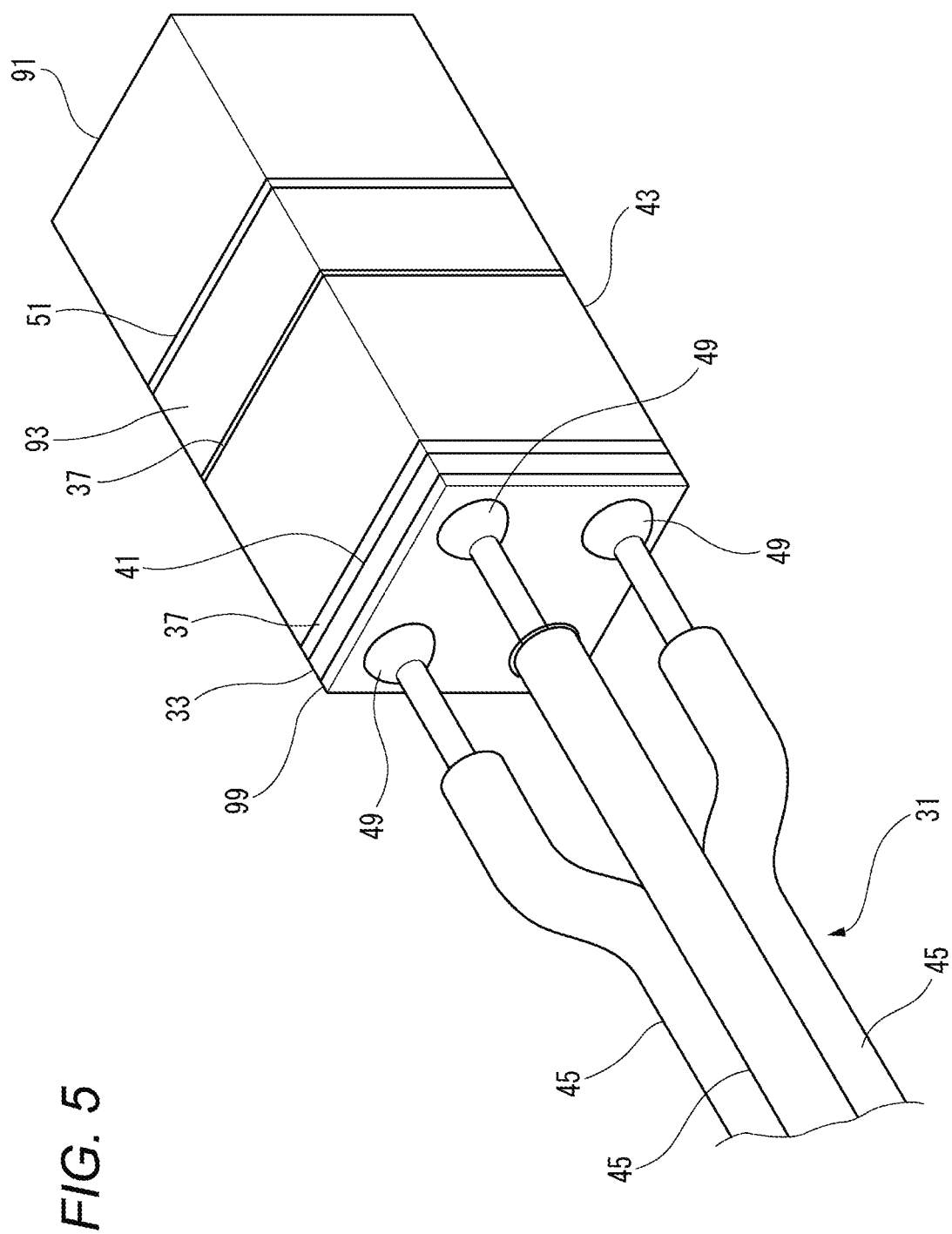
FIG. 5 is a perspective view illustrating an appearance of the imaging element of the endoscope according to the present embodiment that is seen from a rear side with a transmission cable connected to a conductor connection portion.

In the endoscope 11 according to the present embodiment, the endoscope 11 according to the second configuration example has the substrate of the imaging element 33 formed in a square shape and conductor connection portions 49 placed at four corners of the substrate of the imaging element 33 as illustrated in FIG. 5. One of the conductor connection portions 49 is formed in, for example, a circular shape. The four conductor connection portions 49 are placed at the four square corners. As a result, the four conductor connection portions 49 can be placed with a maximum distance of separation from one another.

In the transmission cable 31, conductors of respective electric power and signal lines that are electric wires 45 are covered by insulating coatings. The four electric wires 45 are placed in two, upper and lower, layers with two of the four on the left and the other two on the right. Outer peripheries of the insulating coatings are bundled up by an outer covering, which results in the single transmission cable 31. The respective conductors are formed in the shape of four parallel straight lines in a state where the insulating coatings are peeled off. Tips of the conductors of the electric wires 45 are connected to the conductor connection portions 49 by soldering. The imaging element 33 and the transmission cable 31 are covered by a mold resin 17 as illustrated in FIG. 3. Accordingly, the conductor connection portions 49, the conductors, the insulating coatings of the electric wires 45, and the outer covering of the transmission cable 31 are embedded in the mold resin 17.

In the endoscope 11 according to the second configuration example, the four conductor connection portions 49 can be placed at the four corners of the substrate of the imaging element 33 as described above. Accordingly, the four conductor connection portions 49 can be placed on the square substrate of the imaging element 33 at a maximum distance from one another and in an equally separated state as illustrated in FIG. 5. Accordingly, two of the conductor connection portions 49 that are adjacent to each other are not connected to each other by soldering in a soldering process, ensuring of an insulation distance is facilitated, and a reduction in the diameter of the tip portion 15 can be facilitated.

Third Configuration Example

Figure 4:
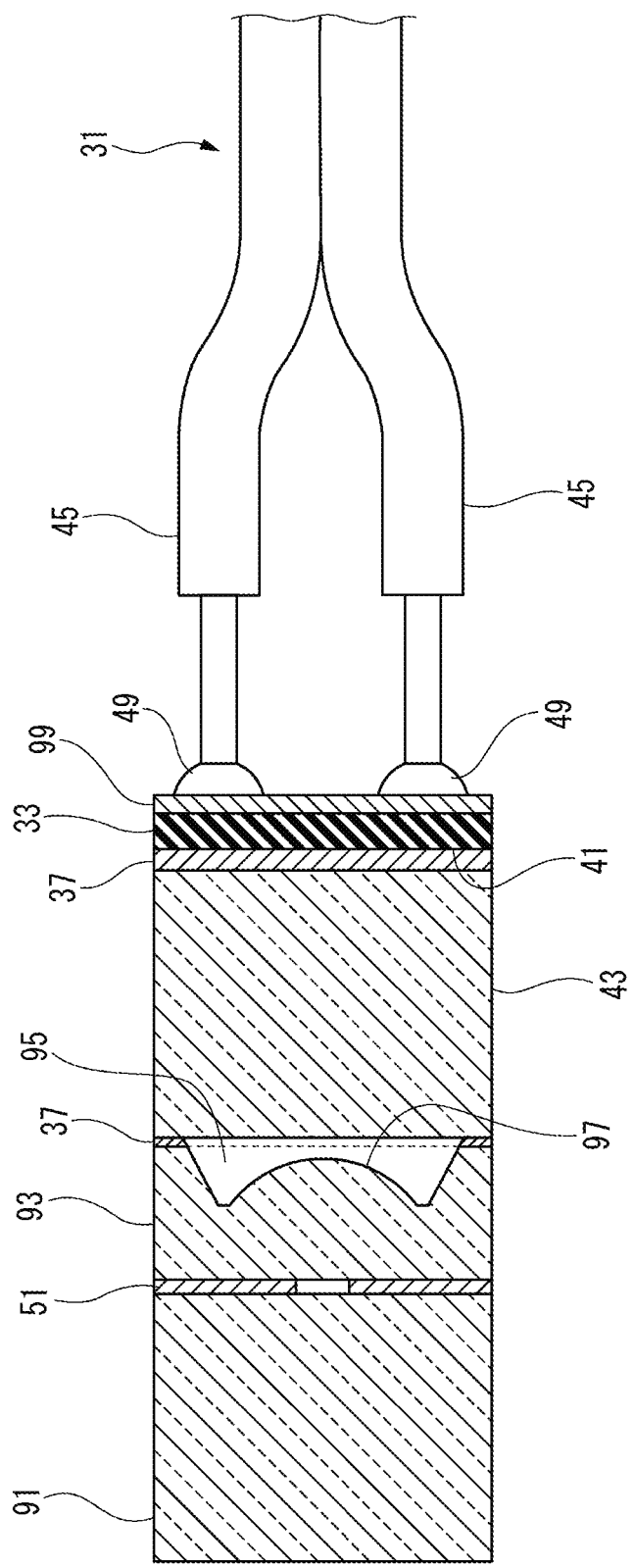
FIG. 4 is a sectional view illustrating a configuration example of a state where a lens and an imaging element of the endoscope according to the present embodiment are attached via an adhesive resin.

FIG. 4 is a sectional view illustrating a configuration example of a state where a lens 93 and the imaging element 33 of the endoscope 11 according to the present embodiment are attached via an adhesive resin 37. As illustrated in FIG. 4, the endoscope 11 according to the third configuration example is provided with an objective cover glass 91, an element cover glass 43, the imaging element 33 where an imaging surface 41 is covered by the element cover glass 43, the lens 93 pinched between the objective cover glass 91 and the element cover glass 43 with its optical axis corresponding to the center of the imaging surface 41, an aperture 51 disposed between the objective cover glass 91 and the lens 93, the adhesive resin 37 fixing the lens 93 and the element cover glass 43, and an air layer 95 disposed between the lens 93 and the element cover glass 43.

A small charge coupled device (CCD) or complementary metal-oxide semiconductor (CMOS) imaging device that has a square shape when seen from the front-rear direction is an example of what constitutes the imaging element 33. In other words, the imaging element 33 has a square outer shape in a direction perpendicular to the axial direction through the optical axis or the lens center of the lens 93. In the imaging element 33, light incident from the outside passes through the aperture 51 disposed between the objective cover glass 91 and the lens 93, and then the light is imaged on the imaging surface 41 by the lens 93 after the passage. In the imaging element 33, in addition, the imaging surface 41 is covered by the element cover glass 43. The element cover glass 43 has a square outer shape in the direction perpendicular to the optical axis. The length of one side of the element cover glass 43 is equal to the length of one side of the imaging element 33.

A UV-curable and thermosetting resin is an example of what constitutes the adhesive resin 37. It is preferable that the adhesive resin 37 is light-transmissive and has a refractive index close to that of air. In a case where the UV-curable and thermosetting resin is used as the adhesive resin 37, an outer surface part can be cured by ultraviolet irradiation and an inner portion of a filling adhesive that cannot be irradiated with ultraviolet rays can be cured by heat treatment. The adhesive resin 37 fixes the lens 93, the optical axis of which corresponds to the center of the imaging surface 41, to the element cover glass 43. As a result, the lens 93 and the imaging element 33 are subjected to direct adhesion and fixing by the adhesive resin 37. In other words, the lens 93 and the imaging element 33 are attached via the adhesive resin 37. The adhesive resin 37 is, for example, a type of adhesive that allows curing to proceed up to a certain level of hardness by ultraviolet irradiation although it requires heat treatment to obtain a final hardness.

The lens 93 and the element cover glass 43 are attached via the adhesive resin 37 in the endoscope 11 according to the present embodiment. As a result, the adhesive resin 37 in the endoscope 11 has a substantially linear shape in a side view (refer to FIG. 5). FIG. 5 is a perspective view illustrating an appearance of the imaging element 33 of the endoscope 11 according to the present embodiment that is seen from a rear side with the transmission cable 31 connected to the conductor connection portions 49. In the endoscope 11 according to the present embodiment, the lens 93 and the element cover glass 43 are attached in edge portions on both end sides of the lens 93 by the adhesive resin 37 and the adhesive resin 37 is applied only to the edge portions.

The lens 93 is, for example, a single lens. The lens 93 is formed in the shape of a prism that has the same outer shape as the imaging element 33 and has a square cross section in the direction perpendicular to the direction of the axis through the optical axis or the lens center. The lens 93 allows incident light from the subject that has passed through the objective cover glass 91 to be imaged on the imaging surface 41 of the imaging element 33 via the element cover glass 43. A recessed portion is formed on a surface of the lens 93 on the element cover glass 43 side. A convex surface portion 97 bulging in a substantially spherical shape is formed on a bottom surface of the recessed portion. With the convex surface portion 97, the lens 93 functions as an optical element performing light focusing. A bulging tip of the convex surface portion 97 is slightly separated from the element cover glass 43. Quadrangular ring-shaped end faces of the lens 93 that surround the recessed portion adhere to the element cover glass 43 via the adhesive resin 37. As a result, a state is achieved where the recessed portion between the lens 93 and the element cover glass 43 is sealed with air inside. It is preferable that the air inside the sealed recessed portion that has become a sealed space is dry air. In addition, the recessed portion may be sealed with nitrogen inside. In this manner, the air layer 95 that has the recessed portion as its internal volume is formed between the lens 93 and the element cover glass 43. The convex surface portion 97 is placed in the air layer 95. In other words, a light-emitting surface of the convex surface portion 97 is in contact with the air in the lens 93.

Whether the number of lenses can be reduced or not is an important requirement for diameter reduction for the endoscope 11 with the maximum outer diameter Dmax of 1.0 mm. Accordingly, important in a case where the lens 93 that is the single lens is disposed in the endoscope 11 is how to make a refractive index difference with respect to the lens in a tiny region in a width direction parallel to the optical axis direction. The endoscope 11 according to the third configuration example is characterized by the air layer with which a large refractive index difference is obtained with respect to the lens 93 being disposed on the optical element surface.

In the endoscope 11 according to the third configuration example, the recessed portion is formed in the lens 93, the convex surface portion 97 is formed on the bottom surface of the recessed portion, and the quadrangular ring-shaped end faces adhere to the element cover glass 43 as described above. Accordingly, the air layer 95 for an increase in refractive index difference with respect to the lens 93 can be ensured in the tiny region. In addition, optical axis alignment between the lens 93 and the imaging surface 41 can be performed with ease. The lens 93 is capable of ensuring the air layer 95, and thus a high level of lens power can be obtained with respect to the lens 93. Accordingly, the number of lenses in the endoscope 11 can be reduced to one. As a result, size and cost reduction for the endoscope 11 can be achieved.

Fourth Configuration Example

In the endoscope 11 according to the present embodiment, the endoscope 11 according to the fourth configuration example is provided with a mold portion 65 and a tubular sheath 61 as illustrated in FIG. 3. The mold portion 65 fixes an outer peripheral surface of the objective cover glass 91 excluding its objective surface, an outer peripheral surface of the lens 93, and the imaging element 33 by coating with the mold resin 17, forms an outer shell of the tip portion 15, and is exposed to the outside. The sheath 61 is formed to have the same outer diameter as the tip portion 15 and is connected to the mold portion 65 by covering at least a part of the mold portion 65.

The sheath 61 is formed of a resin material that has flexibility. The sheath 61 can be provided with a single wire, a plurality of wires, and a braided tensile strength wire on its inner peripheral side so that strength is given. Examples of the tensile strength wire can include an aramid fiber such as a poly-p-phenylene terephthalamide fiber, a polyester fiber such as a polyarylate fiber, a polyparaphenylene benzbisoxazole fiber, and a polyethylene terephthalate fiber, a nylon fiber, a thin tungsten wire, and a thin stainless steel wire. The sheath 61 is formed of the flexible resin material as described above. In addition, the sheath 61 can be provided with the single wire, the plurality of wires, and the braided tensile strength wire on its inner peripheral side so that the strength is given as described above. The material of the tensile strength wire is as described above.

In the endoscope 11, the objective cover glass 91, the lens 93, the element cover glass 43, the imaging element 33 as a whole, a part of the transmission cable 31, and a part of the light guide 57 are coated with the mold resin 17 and fixed with the mold resin 17 exposed to the outside. A radiopaque marker may be included in the tip portion 15 of the endoscope 11. This allows confirmation of the tip position of the endoscope 11 to be facilitated under X-ray fluoroscopy.

The lighting member is disposed along the objective cover glass 91, the lens 93, the element cover glass 43, and the imaging element 33 in the endoscope 11. In other words, the endoscope 11 according to the fourth configuration example has the light guide 57 as an example of the lighting member. This case where the lighting member is the light guide 57 will be described as an example below. Still, the lighting member can also be an LED attached to an insertion tip surface of the tip portion 15. In this case, the light guide 57 is unnecessary.

The light guide 57 is made up of a single strand of optical fiber 59. A plastic optical fiber (POF) or the like is preferably used as the optical fiber 59. Both the core and cladding of the plastic optical fiber are formed from plastic with a silicone resin and an acrylic resin used as its materials. The optical fiber 59 may also be, for example, a bundle fiber in which a plurality of optical fiber strands is bundled up with terminal fittings attached to both of its ends. A tip of the optical fiber 59 is an emission end face in the tip portion 15 and a base end of the optical fiber 59 is connected to a ferrule of the plug portion 23. A light source is an LED disposed in, for example, the socket portion 27. The plug portion 23 is connected to the socket portion 27 in the endoscope 11, and thus light from the LED propagates through the optical fiber 59 of the light guide 57 and is emitted from the tip. According to this configuration, the single strand of optical fiber can constitute the path reaching an illumination light emission end from the light source, and thus optical loss reduction can be achieved.

The endoscope 11 according to the fourth configuration example is provided with the light guide 57 as described above, and thus imaging in a dark portion can be conducted with the endoscope 11 alone.

As illustrated in FIG. 2, the endoscope 11 according to the fourth configuration example has a configuration in which the plurality of light guides 57 as an example of the lighting member is respectively disposed around the objective cover glass 91, the lens 93, the element cover glass 43, and the imaging element 33. For example, the four light guides 57 can be disposed at equal intervals and in a uniform manner. Since the four light guides 57 are respectively disposed at the equal intervals and in the uniform manner as described above around the objective cover glass 91, the lens 93, the element cover glass 43, and the imaging element 33, the endoscope 11 according to the fourth configuration example is unlikely to create a shade above, below, to the left of, and to the right of the subject. Accordingly, the endoscope 11 is capable of obtaining a clearer captured image than in a configuration in which the number of the light guides 57 is one and a configuration in which the number of the light guides 57 is two.

The imaging element 33 is formed to have the square shape in the endoscope 11 according to the present embodiment. The optical fibers 59 of the four light guides 57 are arranged substantially at the centers of respective side portions of the substrate of the imaging element 33 in a space that is sandwiched by the substrate of the imaging element 33 and the circle circumscribed about the substrate of the imaging element 33.

In the endoscope 11 according to the fourth configuration example described above, the space that is sandwiched by the square imaging element 33 and the circular mold portion 65 substantially circumscribed about the imaging element 33 can be effectively used, and thus the plurality of (four, in particular) optical fibers 59 can be easily arranged without an increase in the outer diameter of the tip portion 15. Accordingly, the endoscope 11 can be manufactured with ease and a clear image can be obtained from it without an increase in the outer diameter of the tip portion 15.

In the endoscope 11, the objective cover glass 91, the lens 93, the element cover glass 43, the imaging element 33, the part of the transmission cable 31, and the part (imaging unit) of the light guide 57 are coated with the mold resin 17 and fixed, and thus few components intervene during the fixing of each of these members. Accordingly, the diameter of the tip portion 15 of the endoscope 11 can be reduced, and a minimum-dimension configuration is available in a case where further diameter reduction is pursued. Component costs can be reduced as well. For example, the endoscope 11 can be realized to be capable of being applied such that imaging can be performed on affected areas with extremely small diameters such as the blood vessels in the human body. As a result, size and cost reduction for the endoscope 11 can be achieved.

The mold resin 17 is molded to cover the section that reaches the objective cover glass 91 from the imaging element 33, and thus contributes to an increase in the fixing strength of these imaging units. The mold resin 17 adds to the airtightness (that is, the absence of very small gaps), watertightness, and light-shielding property of the air layer 95 as well. The mold resin 17 adds to the light-shielding property at a time when the optical fiber 59 for the light guide 57 is embedded, too.

The light guide 57 is molded by the mold resin 17 in the tip portion 15 of the endoscope 11, and thus the connection strength between the soft portion 29 and the tip portion 15 can be improved even in the small-diameter endoscope 11 with the light guide 57 allowed to act as a structural material. In the endoscope 11, the coating with the mold resin 17 covers the objective cover glass 91 of the tip portion 15 and the four optical fibers 59 in a case where the tip portion 15 is seen from an insertion side outermost surface (refer to FIG. 2, for example), and thus no clearance exists around (that is, no gap exists around) each of the objective cover glass 91 and the four optical fibers 59. Accordingly, once the endoscope 11 is sterilized (that is, washed) after being used during an inspection or surgery, unnecessary adhesion of residue from the washing, such as a liquid, to the endoscope 11 is mitigated and much more convenience in terms of hygiene can be provided with regard to the use of the endoscope 11 during the next inspection or surgery.

Axes of tip portions and optical axes of lens units are eccentric in some of existing endoscopes. In this type of configuration, the distance to a subject is likely to vary with the rotation angle of the tip portion and stable acquisition of an acceptable image is unlikely. In addition, when the axis of the tip portion and the optical axis of the lens unit are eccentric, the degree of interference between a pipe inner wall and the tip portion varies with the rotation angle of the tip portion and operability is reduced during a movement into a hole with a small diameter in particular. In the endoscope 11, in contrast, the objective cover glass 91, the lens 93, the element cover glass 43, and the imaging element 33 are coaxially connected. In other words, the objective cover glass 91 is placed concentrically with respect to the tip portion 15. As a result, the endoscope 11 according to the fourth configuration example facilitates diameter reduction, allows an acceptable image to be obtained in a stable way, and is capable of adding to insertion operability.

Fifth Configuration Example

It is preferable that the thickness of the sheath 61 ranges from 0.1 to 0.3 mm in the endoscope 11 according to the fifth configuration example.

The mold portion 65 of the endoscope 11 has a small-diameter extending portion 71 that is illustrated in FIG. 3 and extends backwards from a rear end covering the imaging element 33. The small-diameter extending portion 71 is molded in the form of a cylinder and the four optical fibers 59 are embedded therein. The transmission cable 31 is embedded inside the four optical fibers 59 in the small-diameter extending portion 71. An inner diameter side of the sheath 61 is fixed to an outer periphery of the small-diameter extending portion 71 by an adhesive or the like. In other words, the mold portion 65 and the sheath 61 lead to each other with a coaxial maximum outer diameter Dmax of 1.0 mm.

In the endoscope 11 according to the fifth configuration example described above, the thickness of the sheath 61 can be increased up to 0.3 mm, and thus the tensile strength of the sheath 61 can be increased with ease. The transmission cable 31 has a minimum outer diameter of approximately 0.54 mm at this moment. The thickness of the sheath 61 becomes 0.23 mm in a case where the maximum outer diameter Dmax of the tip portion 15 becomes 1.0 mm. In this manner, the maximum outer diameter Dmax of the tip portion 15 can become 1.0 mm in the endoscope 11 by the thickness of the sheath 61 being within the range of 0.1 to 0.3 mm described above.

Sixth Configuration Example

Figure 6:
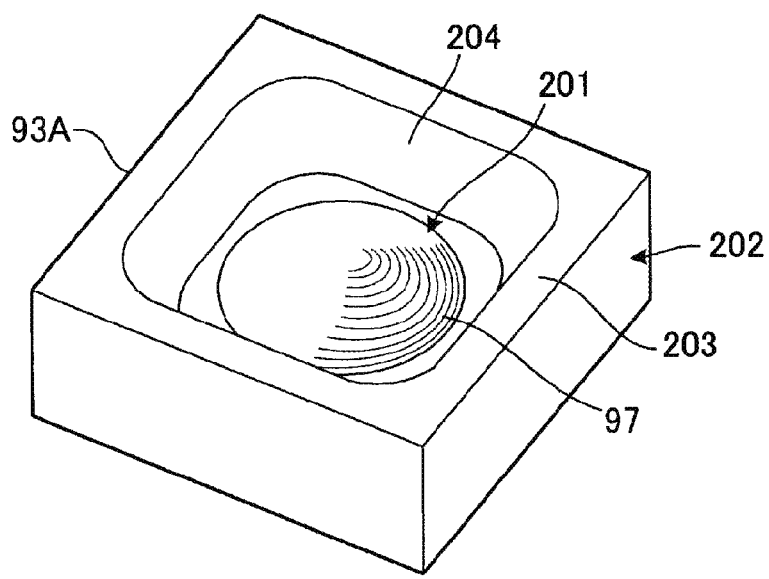
FIG. 6 is a diagram illustrating a first example of a lens shape in the endoscope according to the present embodiment.
Figure 7:
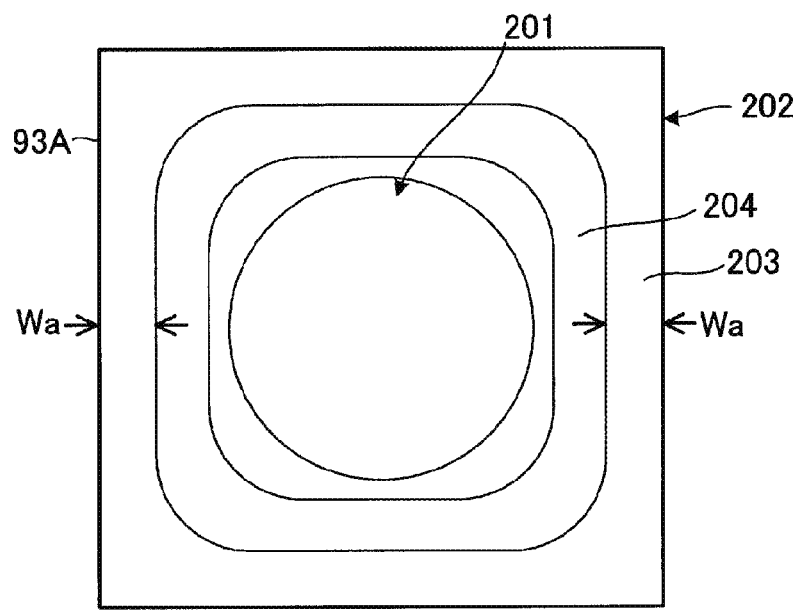
FIG. 7 is a diagram illustrating the first example of the lens shape in the endoscope according to the present embodiment.
Figure 8:
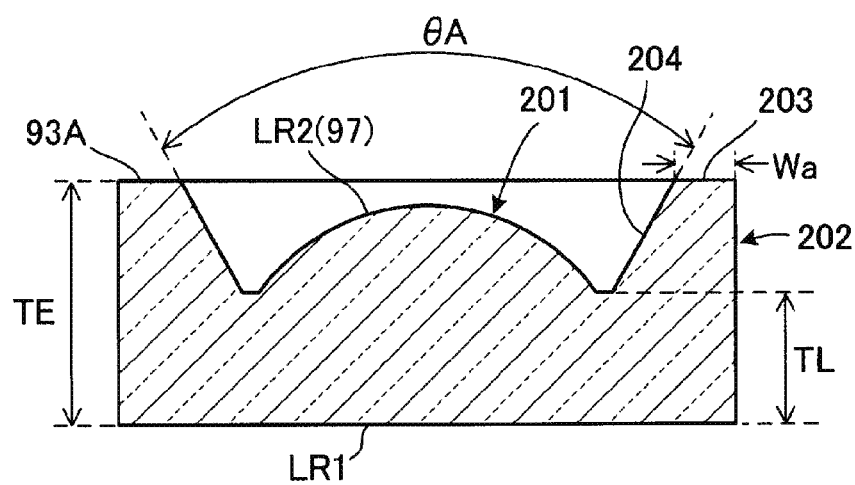
FIG. 8 is a diagram illustrating the first example of the lens shape in the endoscope according to the present embodiment.

The sixth configuration example shows a configuration example of the lens shape as a specific example of the configuration of the lens 93 in the endoscope 11. FIGS. 6 to 8 are drawings illustrating a first example of the lens shape in the endoscope 11 according to the present embodiment.

A single lens constitutes a lens 93A according to the first example. In this single lens, a first surface LR1 on the subject side is a flat surface and a second surface LR2 on an imaging side is a convex surface. An optical element portion 201 is formed in a middle portion of the imaging side of the lens 93A, the optical element portion 201 has the convex surface portion 97 constituting the lens surface of the convex second surface LR2, bulging in a substantially spherical shape, and having the shape of a circular dome, and an edge portion 202 is integrally formed in a peripheral edge portion as a frame that has an adhesion surface 203 which has a flat end face. The edge portion 202 is larger in thickness-direction (optical axis-direction) dimension than a central portion of the convex surface portion 97 of the optical element portion 201, is shaped such that the adhesion surface 203 of the edge portion 202 protrudes more than the convex surface portion 97, and is a part that is fixed to the element cover glass 43 by the adhesive resin 37 adhering to the entire region of the adhesion surface 203. The adhesion surface 203 of the edge portion 202 has a substantially square shape, in which an outer peripheral portion has a square shape and an inner peripheral portion has a rounded square shape, and its four sides excluding corner portions have substantially the same width. An adhesion width Wa at the parts of the adhesion surface 203 of the edge portion 202 where the four sides have the same width is, for example, at least 50 μm. Inside the edge portion 202, the air layer 95 is formed between the convex surface portion 97 as the lens surface of the second surface LR2 and the element cover glass 43.

The lens 93 has a thickness-direction dimension (thickness SRt) of, for example, 100 μm to 500 μm. In the illustrated example, the edge portion 202 has a thickness TE of 200 μm and a thickness TL between the first surface LR1 and an outer peripheral portion of the convex surface portion 97 (second surface LR2) of the optical element portion 201 is 110 μm to 120 μm. An inclined surface 204, which widen from the lens center toward the outer periphery, ranges from the outer peripheral portion of the convex surface portion 97 of the optical element portion 201 to the inner peripheral portion of the adhesion surface 203 of the edge portion 202. The inclined surface 204 has an angle $\pi A$ of, for example, 60° assuming that the angle $\theta A$ is an angle of an opening seen from the lens center.

Figure 9:
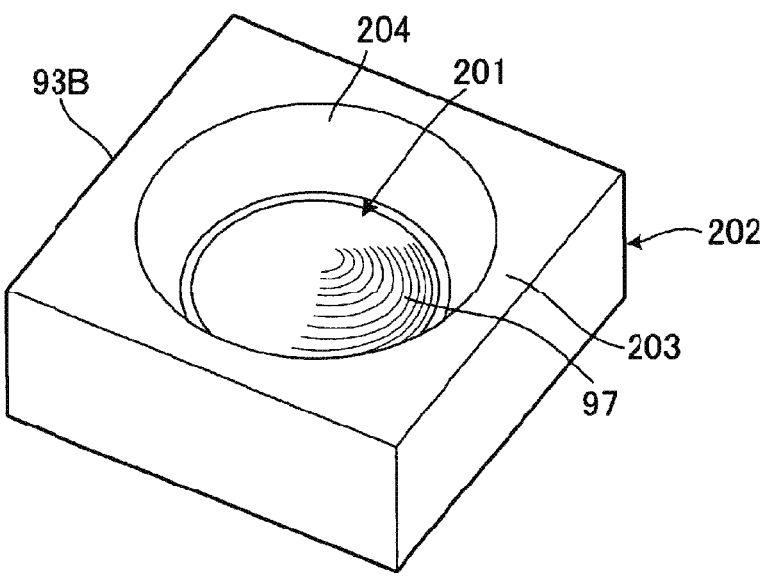
FIG. 9 is a diagram illustrating a second example of the lens shape in the endoscope according to the present embodiment.
Figure 10:
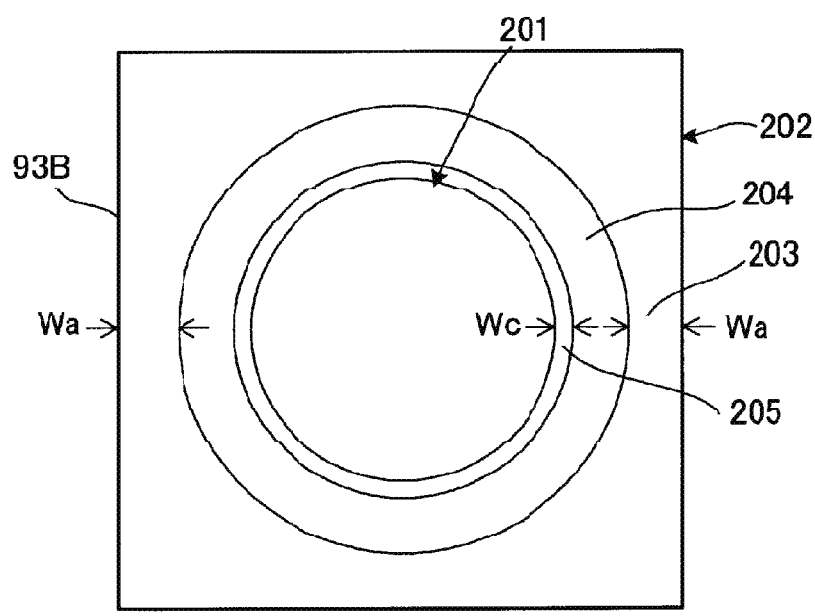
FIG. 10 is a diagram illustrating the second example of the lens shape in the endoscope according to the present embodiment.
Figure 11:
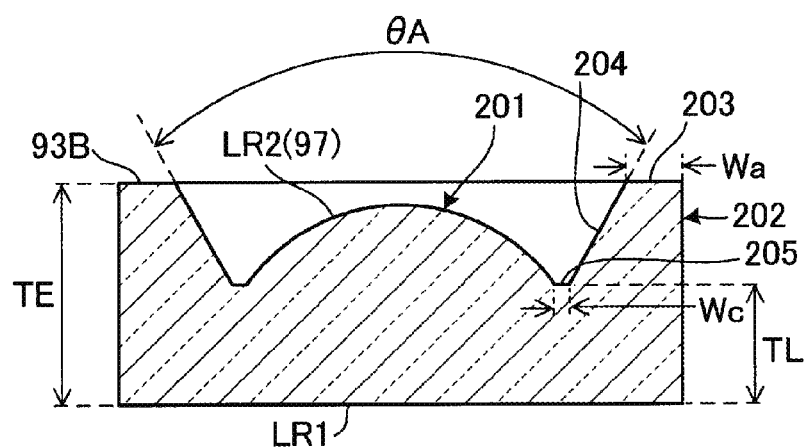
FIG. 11 is a diagram illustrating the second example of the lens shape in the endoscope according to the present embodiment.
Figure 12:
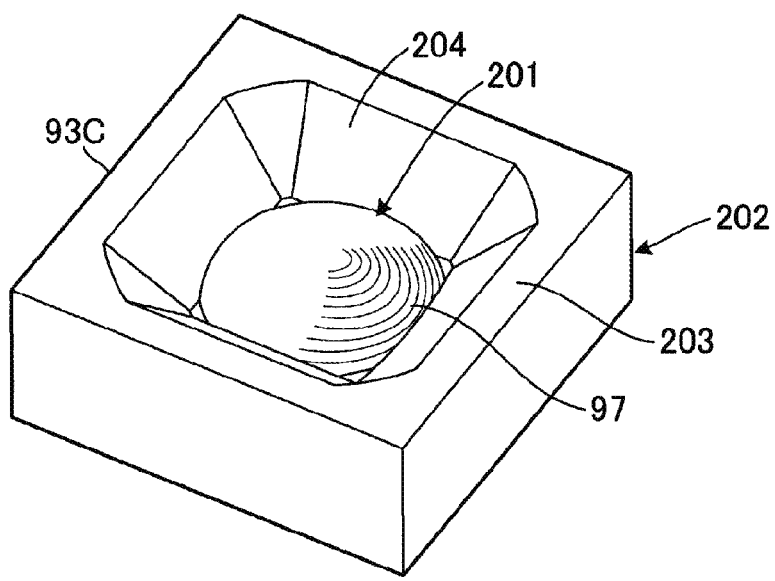
FIG. 12 is a diagram illustrating a third example of the lens shape in the endoscope according to the present embodiment.
Figure 13:
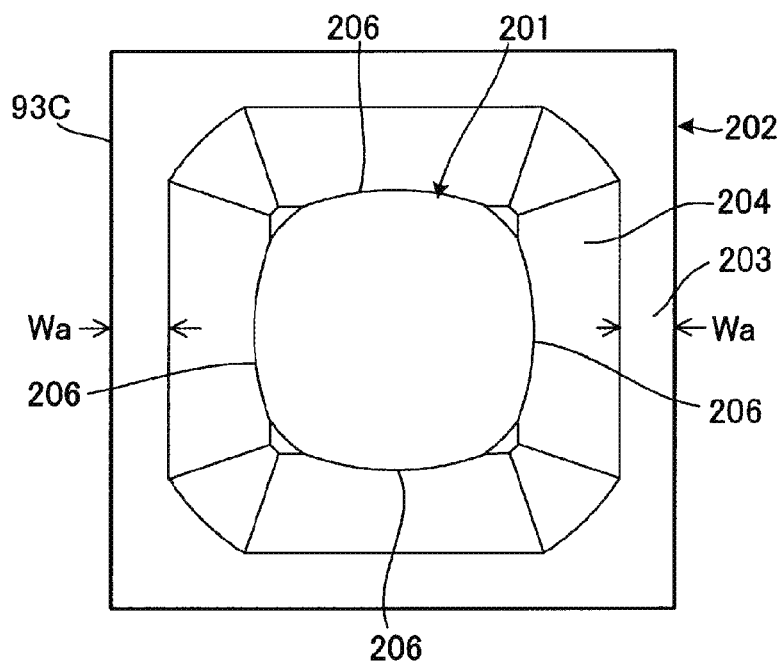
FIG. 13 is a diagram illustrating the third example of the lens shape in the endoscope according to the present embodiment.
Figure 14:
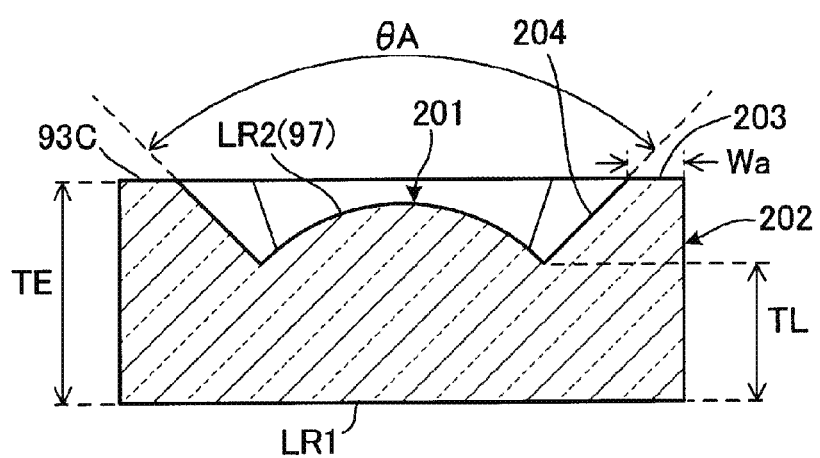
FIG. 14 is a diagram illustrating the third example of the lens shape in the endoscope according to the present embodiment.

FIGS. 9 to 11 are drawings illustrating a second example of the lens shape in the endoscope 11 according to the present embodiment. In a lens 93B according to the second example, the optical element portion 201 is formed in the middle portion of the imaging side of the lens 93B, the optical element portion 201 has the convex surface portion 97 constituting the lens surface of the convex second surface LR2, bulging in a substantially spherical shape, and having the shape of a circular dome, and the edge portion 202 is integrally formed in the peripheral edge portion as the frame that has the adhesion surface 203 which has the flat end face. The following description will focus on the configuration of the parts that differ from those of the first example and description of the parts that are similar to those of the first example will be omitted. The adhesion surface 203 of the edge portion 202 has the shape of a circle concentric with respect to the convex surface portion 97, in which the outer peripheral portion has a square shape and the inner peripheral portion has a circular dome shape, and the adhesion width Wa of the minimal part is, for example, 50 μm. A flat portion 205 that is formed in the outer peripheral portion of the convex surface portion 97 (second surface LR2) of the optical element portion 201 has a width We of, for example, 13 μm. The inclined surface 204, which widens from the lens center toward the outer periphery, ranges from the flat portion 205 in the outer peripheral portion of the optical element portion 201 to the inner peripheral portion of the adhesion surface 203 of the edge portion 202. The angle $\theta A$ of the inclined surface 204 is, for example, 60° assuming that the angle $\theta A$ is the angle of the opening seen from the lens center.

Figure 15:
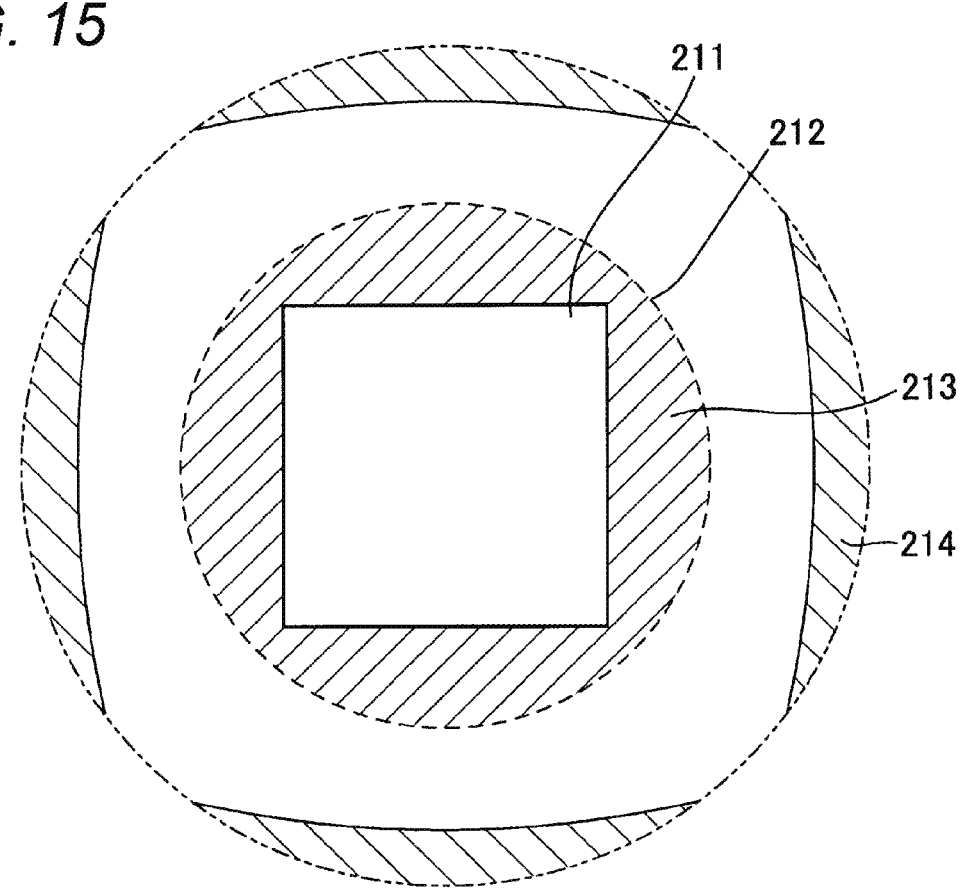
FIG. 15 is a diagram illustrating the third example of the lens shape in the endoscope according to the present embodiment.

FIGS. 12 to 15 are drawings illustrating a third example of the lens shape in the endoscope 11 according to the present embodiment. In a lens 93C according to the third example, the optical element portion 201 is formed in the middle portion of the imaging side of the lens 93C, the optical element portion 201 has the convex surface portion constituting the lens surface of the convex second surface LR2, bulging in a substantially spherical shape, and having the shape of a circular dome, and the edge portion 202 is integrally formed in the peripheral edge portion as the frame that has the adhesion surface 203 which has the flat end face. The following description will focus on the configuration of the parts that differ from those of the first example and description of the parts that are similar to those of the first example will be omitted. The optical element portion 201 in the middle portion has the shape of a mold in which four parts 206 on the circumference corresponding to the four sides of the square shape that is the outer shape of the lens are partially notched in the outer peripheral portion of the circular dome-shaped convex surface portion 97. The inclined surface 204 is formed in the edge portion 202 of the peripheral edge portion and ranges from the inner peripheral portion of the adhesion surface 203 to the outer peripheral portion of the optical element portion 201 that has a barrel shape. As illustrated in FIG. 15, the lens 93C according to the third example is shaped by unnecessary parts of an image circle 212 of the circular lens 93C, that is, four outer periphery regions 214 into which beams imaged on a region 213 outside the four sides of an imaging surface 211 are incident, being cut with respect to the imaging surface 211 of the imaging element 33 that has a square shape. The angle $\theta A$ of the inclined surface 204 in the inner peripheral portion of the edge portion 202 is, for example, 90° assuming that the angle $\theta A$ is the angle of the opening seen from the lens center and the slope can be formed to be gentler than in the first example and the second example. When the angle $\theta A$ of the inclined surface 204 in the inner peripheral portion of the edge portion 202 is 60° as in the first example and the second example, the adhesion width Wa of the adhesion surface 203 of the edge portion 202 can be increased.

The lens 93 is fabricated by nanoimprint, injection molding, or the like. The lens 93 is fabricated by a lens group in which a plurality of tiny lenses that has the same shape is arranged being formed by a mold based on an original plate for the nanoimprint or the like being used, the lens group being released as a molded object, and then it being cut into individual lenses by dicing or the like. A draft needs to be provided during the fabrication of the lens 93 for the lens 93 to be removed from the mold, and the inclined surface 204 of the lens 93 acts as the draft. The higher the level of the draft of the molded object, the better in terms of releasability. Accordingly, it is desirable in terms of releasability that the inclined surface 204 of the lens 93 is gentle with respect to a surface perpendicular to the optical axis of the lens 93. For a decrease in the external dimension of the lens 93, the inclined surface 204 of the lens 93 should be upright to the maximum extent possible. In addition, it is preferable in terms of adhesive strength that the adhesion surface 203 of the edge portion 202 to which the adhesive resin 37 adheres has the largest possible adhesion area in a case where the lens 93 is allowed to adhere to the element cover glass 43 by the adhesive resin 37.

Accordingly, the dimension of the adhesion surface 203 of the edge portion 202 is set by comprehensive consideration being given to each of the factors of the reduction of the diameter of the lens 93, releasability, and adhesive strength so that reliable adhesion can be conducted between the lens 93 and the element cover glass 43 in the edge portion 202. The adhesion width Wa of the adhesion surface 203 of the edge portion 202 is, for example, at least 50 μm in a case where, for example, 0.5 mm is the dimension of one side of the square shape of the cross section perpendicular to the optical axis direction or the axial direction through the lens center as an example of the size of the lens 93 with the external shape of a quadrangular prism. In this case, the dimension of one side of the outer shape of the lens 93 is 0.5 mm or less and the adhesion width Wa of at least 50 μm is ensured for the adhesion surface 203 in the edge portion 202 in the endoscope 11 in which the maximum outer diameter Dmax of the tip portion 15 is 1.0 mm or less. In addition, the angle θA of the inclined surface 204 ranges, for example, from 60° to 90° assuming that the angle θA is the angle of the opening seen from the lens center so that a reduction in the size of the lens 93 and releasability can be achieved at the same time. In this case, the angle of the inclined surface 204 ranges from 30° to 45° with respect to the optical axis direction of the lens 93 (direction parallel to the release direction) and ranges from 45° to 60° with respect to a surface perpendicular to the axial direction through the optical axis or the lens center of the lens 93.

With the endoscope 11 according to the sixth configuration example described above, the small-diameter lens 93 can be realized in which the maximum outer diameter Dmax of the tip portion 15 can be 1.0 mm or less. In addition, a sufficient adhesion area between the lens 93 and the element cover glass 43 can be ensured when the adhesion width Wa of the adhesion surface 203 of the edge portion 202 is at least 50 μm in the lens 93 with a reduced diameter, and thus reliable adhesion and fixing can be conducted. Furthermore, releasability can be improved during lens fabrication when the angle θA of the opening seen from the lens center ranges from 60° to 90° as the angle of the inclined surface 204 between the optical element portion 201 in the middle portion of the lens 93 and the edge portion 202 in the peripheral edge portion.

Seventh Configuration Example

The seventh configuration example shows a configuration example of the surface of the lens 93 adhering to the element cover glass 43 in the endoscope 11.

Figure 16:
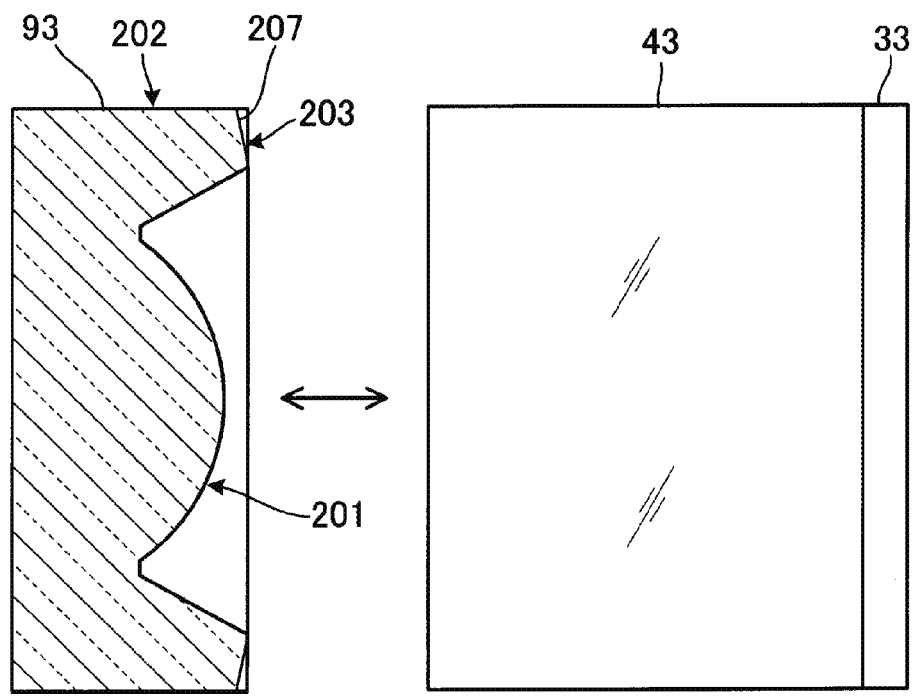
FIG. 16 is a diagram illustrating a configuration example of a surface of the lens of the endoscope according to the present embodiment that adheres to an element cover glass.

FIG. 16 is a diagram illustrating the configuration example of the surface of the lens 93 of the endoscope 11 according to the present embodiment that adheres to the element cover glass 43. The lens 93 is allowed to adhere by the adhesive resin 37 with its quadrangular prismatic external shape corresponding to the element cover glass 43 of the imaging element 33. In this manner, fixing can be conducted with optical axis alignment between the imaging surface 41 of the imaging element 33 and the element cover glass 43 performed with ease. The adhesion surface 203 of the edge portion 202 of the lens 93 may also have an inclined portion 207 inclined to have a predetermined angle, instead of the flat surface parallel to the end face of the element cover glass 43, in a state where it faces the element cover glass 43 for adhesion and fixing. The inclined portion 207 of the adhesion surface 203 has a tapered shape and is inclined from the inner peripheral portion toward the outer peripheral portion of the edge portion 202 with the thickness dimension of the outer peripheral portion very slightly reduced. The inclined portion 207 of the adhesion surface 203 has an inclination angle of, for example, at least 0.5°. In a case where a very small amount of the adhesive resin 37 is applied to the adhesion surface 203 of the edge portion 202 for adhesion between the lens 93 and the element cover glass 43, the adhesive resin 37 on the adhesion surface is likely to move to the outer periphery side and is unlikely to move to the inside of the edge portion 202 because of the inclined portion 207 of the adhesion surface 203, and thus the adhesive resin 37 interfering with the air layer 95 formed in the optical element portion 201 can be prevented.

In the endoscope 11 according to the seventh configuration example described above, penetration of the air layer 95 between the lens 93 and the element cover glass 43 by the adhesive resin 37 can be prevented and reliable adhesion and fixing can be conducted between the lens 93 and the element cover glass 43 with the air layer 95 ensured.

Eighth Configuration Example

The eighth configuration example shows a specific example of the configuration of an optical system in the endoscope 11.

The specific example of the configuration of the optical system including the objective cover glass 91, the lens 93, and the element cover glass 43 will be shown below.

Figure 17:
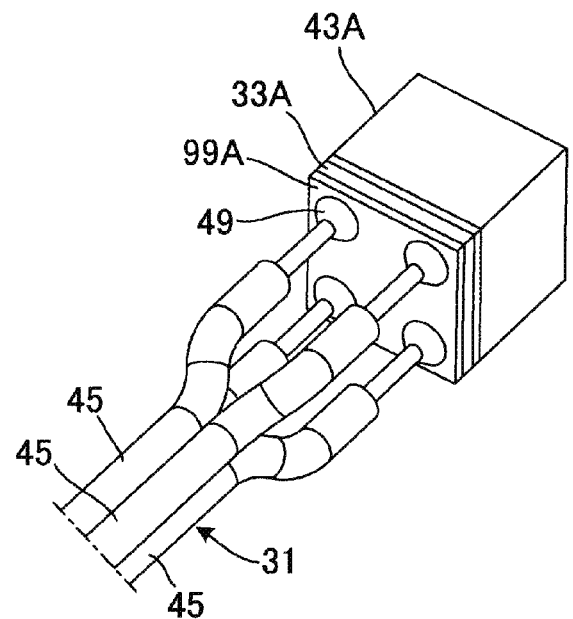
FIG. 17 is a diagram illustrating a first example of the imaging element of the endoscope according to the present embodiment.
Figure 18:
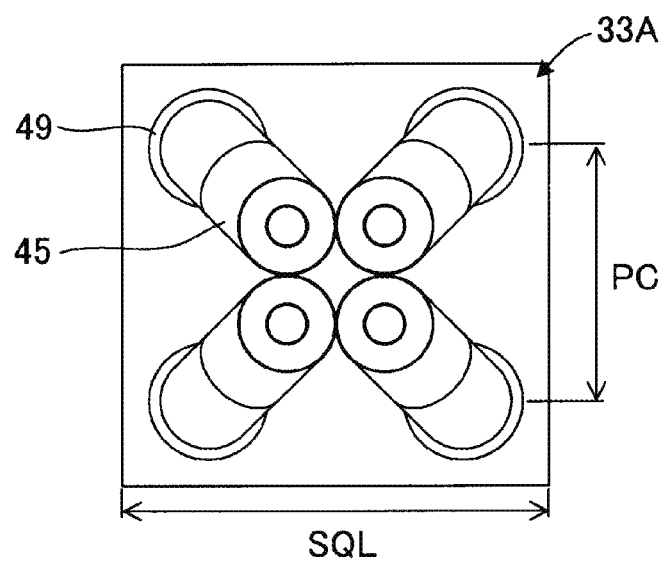
FIG. 18 is a diagram illustrating the first example of the imaging element of the endoscope according to the present embodiment.

Objective Cover Glass 91
Thickness TGt of objective cover glass 91: TGt=0.1 to 0.5 mm
Example of material of objective cover glass 91: BK7 (manufactured by Schott), nd=1.52, vd=64.2
Refractive index ndF of objective cover glass 91: $1.3 \leq ndF$
Abbe number vdF of objective cover glass 91: $30 \leq vdF$
Element Cover Glass 43
Thickness SGt of element cover glass 43: SGt=0.1 to 0.5 mm
Example of material of element cover glass 43: BK7 (manufactured by Schott), nd=1.52, vd=64.2
Refractive index ndR of element cover glass 43: $1.3 \leq ndR \leq 2.0$, $ndF \leq ndR$
Abbe number vdR of element cover glass 43: $40 \leq vdR$, $vdF \leq vdR$
Lens 93
Focal distance f of lens 93: $0.1 \text{ mm} \leq f \leq 1.0 \text{ mm}$
F number FNO of lens 93: $1.4 \leq FNO \leq 8.0$ Ninth Configuration Example The ninth configuration example shows a specific example of the configuration of the imaging element 33 in the endoscope 11. FIGS. 17 and 18 are drawings illustrating a first example of the imaging element 33 in the endoscope 11 according to the present embodiment.

An imaging element 33A according to the first example is formed such that it has a quadrangular sectional shape when cut by a plane perpendicular to the axial direction through the optical axis or the lens center of the lens 93. In this case, the imaging surface on an element cover glass 43A side and the terminal surface on the transmission cable side have a quadrangular outer shape and the imaging element 33A and the element cover glass 43A are formed in the external shape of a quadrangular prism. In addition, the imaging element 33A and the element cover glass 43A are formed to have the same quadrangular prismatic external shape as the lens 93 (not illustrated).

An electric circuit 99A following a circuit pattern is disposed on a substrate (terminal surface) disposed on a rear end side of the imaging element 33A with the conductor connection portions (connection clamps) 49 respectively disposed at the four corner portions and the transmission cable 31 based on the four electric wires 45 connected by soldering or the like. In other words, the four electric wires 45 are connected to the four corner portions of the terminal surface of the imaging element 33A. The four electric wires 45 are positioned in and connected to the four corner portions of the terminal surface of the imaging element 33A in a state where each of their end portions is molded in a crank shape. The width (length of one side of the quadrangular section) SQL of the outer shape of the imaging element 33A is, for example, 0.5 mm or less. The pitch PC between those of the four electric wires 45 that are next to each other is, for example, at least 0.3 mm.

Figure 19:
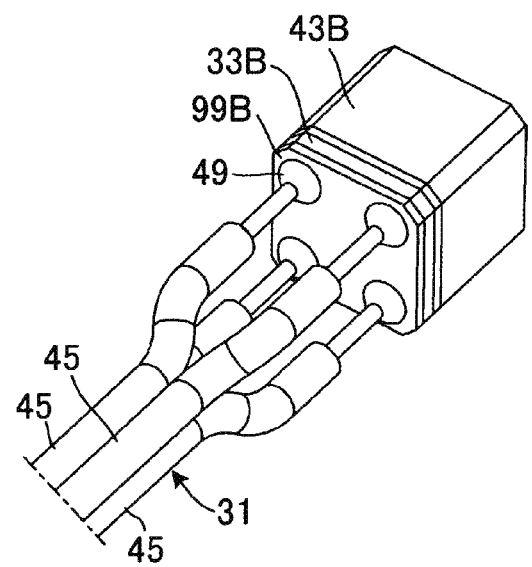
FIG. 19 is a diagram illustrating a second example of the imaging element of the endoscope according to the present embodiment.
Figure 20:
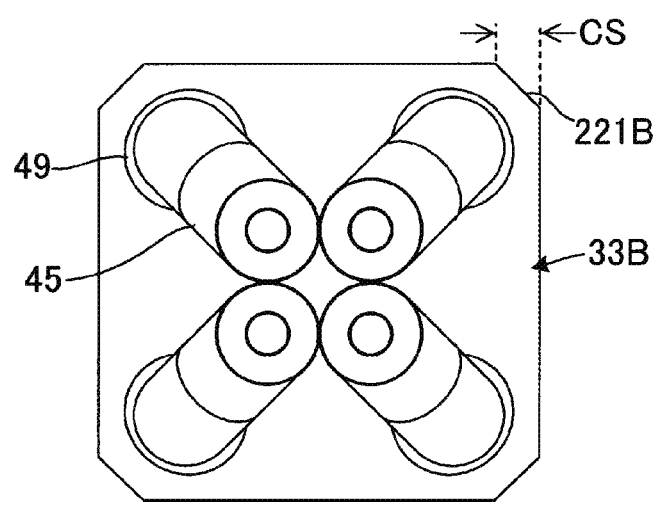
FIG. 20 is a diagram illustrating the second example of the imaging element of the endoscope according to the present embodiment.

FIGS. 19 and 20 are drawings illustrating a second example of the imaging element 33 in the endoscope 11 according to the present embodiment. An imaging element 33B according to the second example is formed such that it has an octagonal sectional shape when cut by the plane perpendicular to the axial direction through the optical axis or the lens center of the lens 93 and the imaging element 33B and a element cover glass 43B are formed to have the external shape of an octagonal prism. In addition, the imaging element 33B, the element cover glass 43B, and an electric circuit 99B are formed to have the same octagonal prismatic external shape as the lens 93 (not illustrated). The following description will focus on the configuration of the parts that differ from those of the first example and description of the parts that are similar to those of the first example will be omitted.

The second example is an example that has an octagonal shape obtained by each of the four corner portions (four corners) of the quadrangular sectional shape of the imaging element 33B being cut (chamfered) in the form of one cut surface 221B. When it comes to the dimension of the cut part of the outer shape of the imaging element 33B, a dimension CS to the end portion of the cut surface 221B with respect to the vertex of the quadrangular shape is, for example, 20 to 50 μm. When the four corner portions of the outer shape of the imaging element 33B are cut in the form of the cut surface 221B as described above, the inter-electric wire pitch PC of the four electric wires 45 can be separated to the maximum extent possible and the external dimension of the imaging element 33B in a diagonal direction can be reduced, which can contribute to further endoscope diameter reduction. When the dimension CS of the cut part is 21.2 μm, for example, the external dimension of the imaging element 33B in the diagonal direction is reduced by 15 μm at one place and the diameter is reduced by 30 μm in both ends in the diagonal direction. When this configuration of the cut surface 221B is applied to an imaging element in which the external dimension SQL of one side is 0.5 mm and the external dimension in the diagonal direction is 0.705 mm in a state where the external shape is a square shape, the external dimension in the diagonal direction is reduced to 0.675 mm by the chamfering and a small-diameter endoscope in which φ is 0.7 mm or less can be realized.

Figure 21:
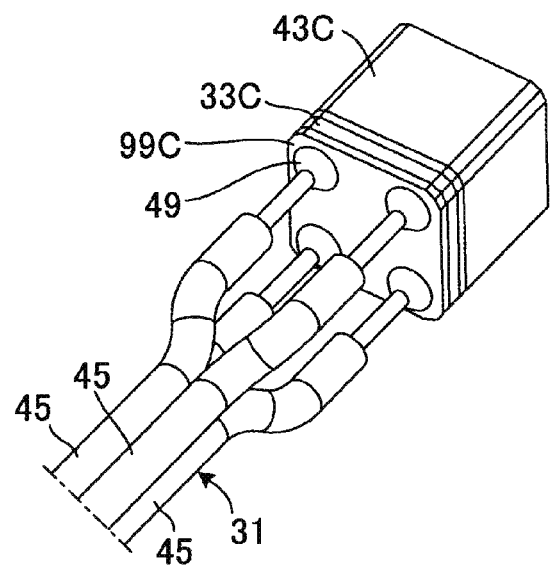
FIG. 21 is a diagram illustrating a third example of the imaging element of the endoscope according to the present embodiment.
Figure 22:
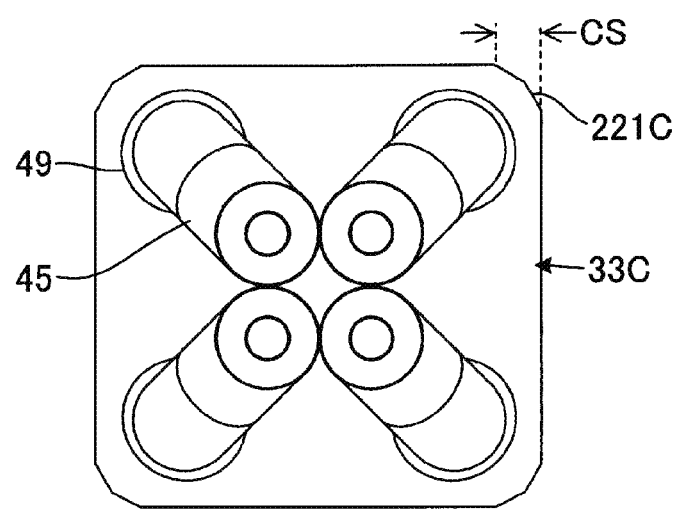
FIG. 22 is a diagram illustrating the third example of the imaging element of the endoscope according to the present embodiment.

FIGS. 21 and 22 are drawings illustrating a third example of the imaging element 33 in the endoscope 11 according to the present embodiment. An imaging element 33C according to the third example is formed such that it has a dodecagonal sectional shape when cut by the plane perpendicular to the axial direction through the optical axis or the lens center of the lens 93 and the imaging element 33C and a element cover glass 43C are formed to have the external shape of a dodecagonal prism. In addition, the imaging element 33C, the element cover glass 43C, and an electric circuit 99C are formed to have the same octagonal prismatic external shape as the lens 93 (not illustrated). The following description will focus on the configuration of the parts that differ from those of the first example and description of the parts that are similar to those of the first example will be omitted. The third example is an example that has a dodecagonal shape obtained by each of the four corner portions of the quadrangular sectional shape of the imaging element 33C being cut in the form of two cut surfaces 221C. When it comes to the dimension of the cut part of the outer shape of the imaging element 33C, the dimension CS to the end portion of the cut surface with respect to the vertex of the quadrangular shape can exceed that of the second example because of the cutting with the two surfaces. Accordingly, the diameter of the imaging element can be further reduced.

The sectional shape in the direction perpendicular to the axial direction through the lens optical axis or the lens center of the imaging element 33 is not limited to the quadrangular, octagonal, and dodecagonal shapes and may be a shape that has 4×n sides (n being a natural number) such as the shape of a hexadecagon. When the imaging element 33 is configured to have a sectional shape that has the 4×n sides as described above, the diameters of the imaging element and the endoscope can be further reduced while the transmission cable 31 based on the four electric wires 45 is allowed. When the four corners of the sectional shape of the imaging element 33 that has the 4×n sides have a chamfered shape, the dimension of the imaging element 33 in the diagonal direction can be further reduced, and then contribution can be made to further diameter reduction.

With the endoscope 11 according to the ninth configuration example described above, the small-diameter imaging element 33 can be realized in which the maximum outer diameter Dmax of the tip portion 15 can be 1.0 mm or less.

The endoscope 11 according to the present embodiment is provided with the imaging element 33 disposed in the tip portion 15 of the insertion portion 21 with the imaging surface 41 covered by the element cover glass 43, the lens 93 that allows the incident light from the subject to be imaged on the imaging surface 41, and the adhesive resin 37 fixing the lens 93 and the element cover glass 43 to each other. The lens 93 is formed to have a prismatic external shape with the single lens in which the first surface on the subject side is the flat surface and the second surface on the imaging side is the convex surface constituting the lens 93. The optical element portion 201 is formed in the middle portion of the imaging side of the lens 93, the optical element portion 201 has the convex surface portion 97 constituting the convex lens surface and bulging in a substantially spherical shape, and the edge portion 202 that has the adhesion surface 203 which has the flat end face is integrally formed in the peripheral edge portion. In this manner, the small-diameter lens 93 can be realized in which the maximum outer diameter Dmax of the tip portion 15 can be 1.0 mm or less.

In the endoscope 11 according to the present embodiment, the adhesion surface 203 of the lens 93A has a substantially square shape in which the outer peripheral portion has a square shape and the inner peripheral portion has a rounded square shape.

In the endoscope 11 according to the present embodiment, the adhesion surface 203 of the lens 93B has the shape of a circle concentric with respect to the convex surface portion 97, in which the outer peripheral portion has a square shape and the inner peripheral portion has a circular dome shape.

In the endoscope 11 according to the present embodiment, the optical element portion 201 of the lens 93C has the shape of a mold in which the four parts on the circumference corresponding to the four sides of the square shape that is the outer shape of the lens are partially notched in the outer peripheral portion of the circular dome-shaped convex surface portion 97. As a result, the inclined surface 204 between the optical element portion 201 and the edge portion 202 can be formed to have a gentle slope and releasability can be improved during lens fabrication. In a case where the slope of the inclined surface 204 is the same, the adhesion width Wa of the adhesion surface 203 of the edge portion 202 can be increased and adhesive strength can be improved.

In the endoscope 11 according to the present embodiment, the lens 93 has the inclined surface 204 that widens from the lens center toward the outer periphery and ranges from the outer peripheral portion of the convex surface portion 97 to the inner peripheral portion of the adhesion surface 203, the angle of the inclined surface 204 ranges from 60° to 90° assuming that it is the angle θA of the opening seen from the lens center, and the adhesion width Wa of the adhesion surface 203 is at least 50 μm. Accordingly, reliable adhesion and fixing can be conducted between the lens 93 and the element cover glass 43 with the lens 93 that has a reduced diameter. Since the angle of the inclined surface 204 can be sufficiently ensured, releasability can be improved during lens fabrication.

In the endoscope 11 according to the present embodiment, the adhesion surface 203 of the lens 93 has the tapered inclined portion 207 inclined from the inner peripheral portion toward the outer peripheral portion of the edge portion 202. Accordingly, the adhesive resin 37 applied to the adhesion surface 203 is likely to move to the outer periphery side and is unlikely to move to the inside of the edge portion 202, and thus the adhesive resin 37 interfering with the air layer 95 formed in the optical element portion 201 can be prevented.

The endoscope 11 according to the present embodiment is provided with the objective cover glass 91, which covers the surface of the lens 93 on the subject side, as well as the imaging element 33, the element cover glass 43, the adhesive resin 37, and the lens 93. When it comes to an optical material that constitutes the objective cover glass 91, the thickness TGt satisfies 0.1 mm≤TGt≤0.5 mm, the refractive index ndF satisfies 1.3≤ndF, and the Abbe number vdF satisfies 30≤vdF. When it comes to an optical material that constitutes the element cover glass 43, the thickness SGt satisfies 0.1 mm≤SGt≤0.5 mm, the refractive index ndR satisfies 1.3≤ndR≤2.0 and ndF≤ndR, and the Abbe number vdR satisfies 40≤vdR and vdF≤vdR. When it comes to the lens 93 based on the single lens, the focal distance f satisfies 0.1 mm≤f≤1.0 mm and the F number FNO satisfies 1.4≤FNO≤8.0. In this manner, the small-diameter lens 93 can be realized in which the maximum outer diameter Dmax of the tip portion 15 can be 1.0 mm or less.

When the distance from an imaging point on the imaging side in the focal distance of the lens 93 to the subject side end face of the element cover glass 43 is x (0≤x≤f), the maximum angle of the beam emitted to the imaging point from the lens 93 in an air-only state with respect to the optical axis is θair, and the maximum angle of the beam emitted to the imaging point from the lens 93 in a state including the element cover glass 43 through the element cover glass 43 with respect to the optical axis is θgl in the endoscope 11 according to the present embodiment, the lens 93 and the element cover glass 43 is based on a combination of the focal distance f, the F number FNO, and the refractive index ndR satisfying 0.1≤x·(tan θair)/(tan θgl)≤0.5. As a result, a desired optical performance can be obtained from the small-diameter lens 93.

The endoscope 11 according to the present embodiment is provided with the transmission cable 31 that has the four electric wires 45 which are respectively connected to the four conductor connection portions 49 disposed on the surface of the imaging element 33 on the side opposite to the imaging surface 41 as well as the imaging element 33, the element cover glass 43, the adhesive resin 37, and the lens 93. The imaging element 33 has a sectional shape that has the 4×n sides (n being a natural number) in the direction perpendicular to the axial direction through the optical axis or the lens center of the lens 93 and the four electric wires 45 are respectively connected to the four conductor connection portions 49 placed at the four corners of the rear end face of the imaging element 33 which has the 4×n sides. As a result, the small-diameter imaging element 33 can be realized in which the maximum outer diameter Dmax of the tip portion 15 can be 1.0 mm or less.

In the endoscope 11 according to the present embodiment, the four corners of the sectional shape of the imaging element 33 that has the 4×n sides have a chamfered shape. As a result, the dimension of the imaging element 33 in the diagonal direction can be further reduced and contribution can be made to further diameter reduction.

In the endoscope 11 according to the present embodiment, the imaging element 33 and the element cover glass 43 have the same prismatic external shape that has the 4×n sides as the lens 93. As a result, the outer diameter reaching the imaging element 33 through the element cover glass 43 from the lens 93 can be further reduced.

The length of one side of the cross section of the imaging element 33 in the endoscope 11 according to the present embodiment that has the 4×n sides is 0.5 mm or less in the direction perpendicular to the axial direction through the optical axis or the lens center. As a result, the external dimension of the imaging element 33 in the diagonal direction can be reduced to approximately 0.7 mm.

In the endoscope 11 according to the present embodiment, the tip portion 15 is formed to have a maximum outer diameter ranging from the finite diameter to 1.0 mm, which is equivalent to the diameter of the circle circumscribed about the substrate of the imaging element 33. As a result, the maximum outer diameter Dmax can be less than 1.0 mm, and thus insertion into the blood vessels in the human body can be further facilitated.

Tenth Configuration Example

Figure 23:
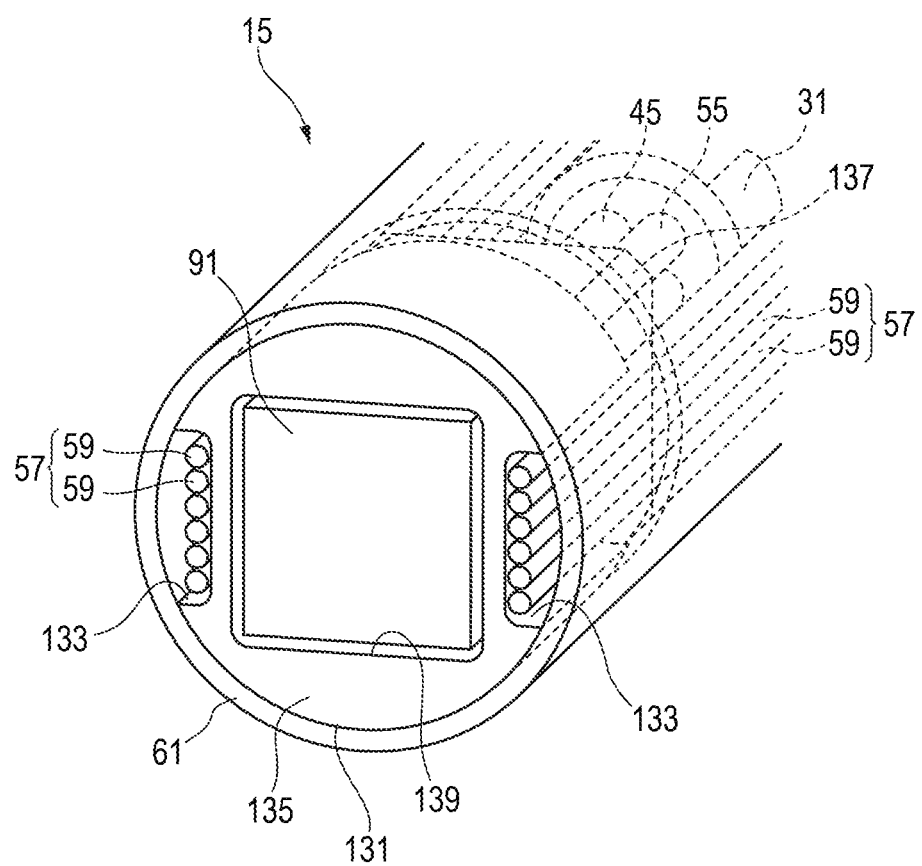
FIG. 23 is an enlarged perspective view of a main part, in which a light-shielding member of the endoscope according to the present embodiment is a notched holder.
Figure 24:
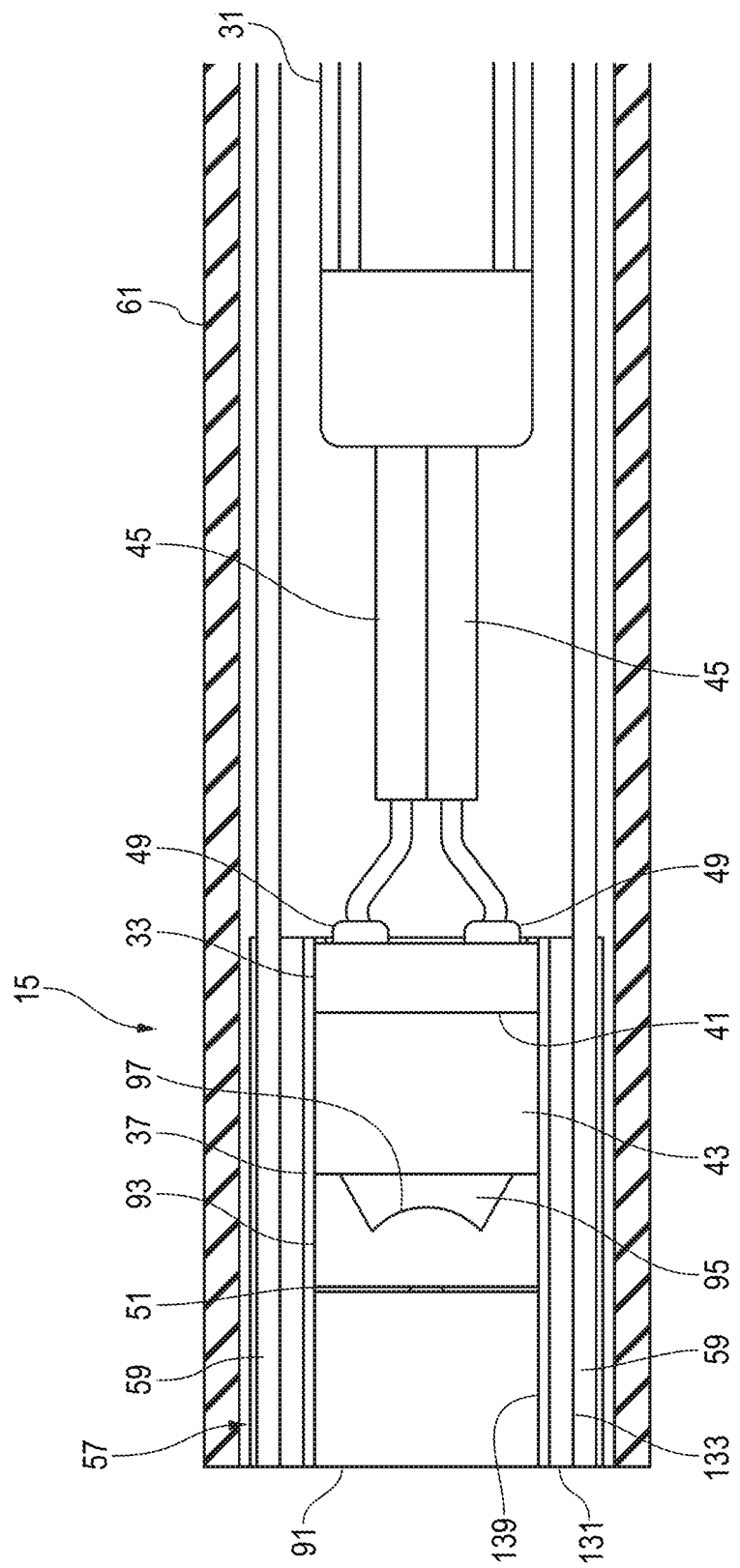
FIG. 24 is a plan sectional view of the endoscope illustrated in FIG. 23.
Figure 25:
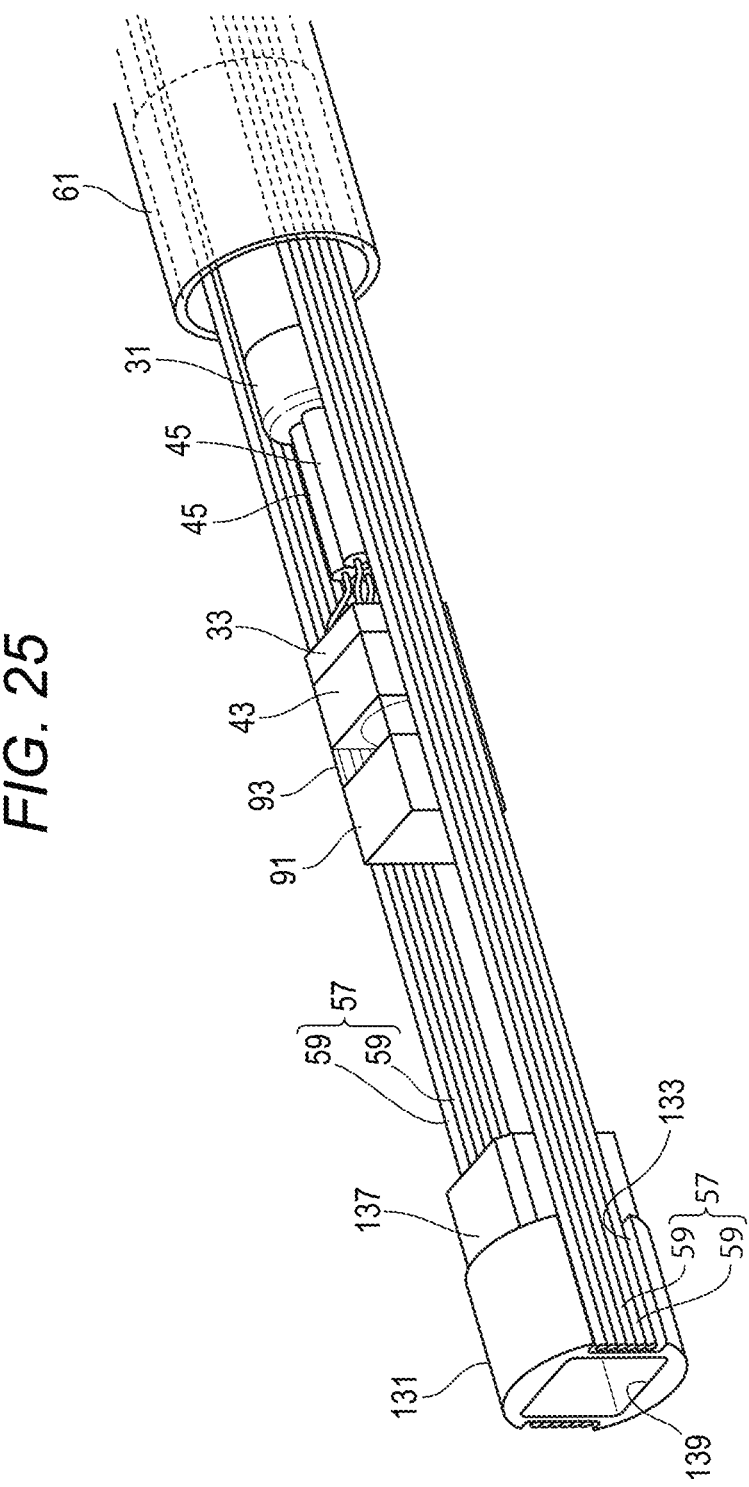
FIG. 25 is an exploded perspective view of the endoscope illustrated in FIG. 23.

FIG. 23 is an enlarged perspective view of a main part, in which a light-shielding member of the endoscope 11 according to the present embodiment is a notched holder. FIG. 24 is a plan sectional view of the endoscope 11 illustrated in FIG. 23. FIG. 25 is an exploded perspective view of the endoscope 11 illustrated in FIG. 23.

The endoscope 11 according to the tenth configuration example is provided with a single lens (such as the lens 93) that has a quadrangular outer shape (such as a square shape and a rectangular shape) in the direction perpendicular to the optical axis or the lens center, the sheath 61 placed coaxially with respect to the optical axis or the lens center and surrounding the lens 93 with the surrounding outer periphery having a circular shape, the lighting member (such as the light guide 57) placed between the outer periphery of the sheath 61 and at least one side of the lens 93 and extending along the optical axis or the lens center, and the light-shielding member (such as a cylinder holder 131) disposed between the lens 93 and the light guide 57. The endoscope 11 further includes the imaging element 33 that has a quadrangular outer shape (such as a square shape and a rectangular shape) in the direction perpendicular to the optical axis or the lens center with the length of its one side being equal to the length of one side of the lens and the element cover glass 43 covering the imaging surface 41 of the imaging element 33 and having the same outer shape as the imaging element 33 in the direction perpendicular to the optical axis or the lens center.

This endoscope 11 is assembled as follows. Specifically, a camera Assy (that is, a unit made up of a plurality of components related to a camera, the same applies hereinafter) is completed by assembly of the lens 93, the imaging element 33, and the transmission cable 31 illustrated in FIG. 25. Then, a fiber Assy (that is, a unit made up of a plurality of components related to the optical fiber 59, the same applies hereinafter) is assembled. The fiber Assy is made up of, for example, the plurality of light guides 57 and the cylinder holder 131 as an example of the light-shielding member. Then, the camera Assy and the fiber Assy are fixed by insertion into an opening portion at the center of a housing of the cylinder holder 131 that is the fiber Assy. A distance of approximately 50 (μm) or more is ensured between one side of the objective cover glass 91 and a notch 133. Finally, the cylinder holder 131 is wrapped with the sheath 61 and the sheath 61 is fixed without a gap by the adhesive resin 37.

In the endoscope 11 according to the tenth configuration example, the light guide 57 is placed between the sheath 61 that has the circular outer periphery and at least one side of the quadrangular lens 93. As a result, that space that is attributable to the shape difference between the circular part of the sheath 61 and the quadrangular part of the lens 93 can be used for the placement of the light guide 57 and member placement density in the tip portion 15 can be increased. In other words, space efficiency can be improved compared to existing configurations in which the light guide 57 is placed on the outer periphery of a circular lens. As a result, a useless space can be suppressed and size reduction can be facilitated. Since the lens 93 and the imaging element 33 have a quadrangular shape in the endoscope 11, alignment between the lens center and the imaging center can be performed with ease. In addition, the four sides of the lens 93 and the four sides of the imaging element 33 can be fixed to each other by the adhesive resin 37 and the four corners of the lens 93 and the imaging element 33 can be fixed to each other by the adhesive resin 37, and thus an increase in fixing area can be achieved. As a result, the lens 93 and the imaging element 33 can be fixed with a high level of strength.

In the endoscope 11 according to the tenth configuration example, the imaging element 33 has a quadrangular outer shape. The sheath 61 has a circular outer shape. In a case where the inner diameter of the sheath 61 is allowed to approach the corner portion of the quadrangular imaging element 33 to the maximum extent allowed by strength, the area that can be used in the sheath becomes the space other than the space where the quadrangular imaging element 33 that is positioned at the center is placed. This residual space is made up of four arcs and a half-moon columnar-shaped portion connecting both ends of this arc with one quadrangular side (straight line slightly longer than the one side to be specific). In the endoscope 11, the light-shielding member (cylinder holder 131) is formed as a square hole tube in which the four half-moon columnar-shaped portions are respectively connected in the thin portion outside the corner portion of the imaging element 33. In other words, the cylinder holder 131 of the endoscope 11 is formed by the residual space other than the essential space being made the most of. As a result, size reduction can be realized while light leaking from the extension-direction outside surface of the optical fiber 59 is reliably blocked. This cylinder holder 131 can be a metallic holder (made from, for example, a SUS material).

The maximum outer diameter of the endoscope 11 illustrated in FIG. 23 being 1.0 mm or less will be described in detail below with reference to FIG. 23. In FIG. 23, the shortest distance between the inner peripheral surface of the sheath 61 and the four corners (corner portions) of the objective cover glass 91 that has a quadrangular outer shape (such as a square shape) in the direction perpendicular to the lens center is approximately 50 μm in view of the manufacturability (including process ability) and handling property (that is, being unlikely to be broken during assembly) of the endoscope 11. In addition, the length of one side of each of the objective cover glass 91, the lens 93, the element cover glass 43, and the imaging element 33 that has a quadrangular outer shape (such as a square shape) in the direction perpendicular to the lens center is 500 μm, and thus its diagonal dimension is approximately 705 μm. In addition, the thickness of the sheath 61 currently used is 97 (μm) and the maximum outer diameter Dmax of the endoscope 11 is 705 (μm)+50 (μm)+50 (μm)+97 (μm)≅1,000 (μm)=1.0 (mm), which is 1.0 (mm) or less.

Because the notch 133 is disposed in the thick half-moon columnar-shaped portion or a through-hole is drilled in this cylinder holder 131, the insertion space of the light guide 57 can be easily ensured with little decrease in the strength of the holder. In other words, it can be said that the shape is extremely high in terms of space efficiency. When the notch 133 is formed in a rectangular shape in which a long side is along one side in this case, the light guide can be efficiently placed and assemblability can be improved.

In the endoscope 11 according to the tenth configuration example, the cylinder holder 131 is longer than the length between the imaging surface 41 of the imaging element 33 and an insertion tip surface 135 of the endoscope 11 in the tip portion 15.

In the endoscope 11 according to the tenth configuration example, the cylinder holder 131 shields the lens side surface of the lens 93 by extending more backwards than the imaging surface 41, and thus penetration of a medium from the lens side surface by leaking light from the extension-direction outside surface of the optical fiber 59 can be reliably prevented.

In the endoscope 11 according to the tenth configuration example, the notch 133 is formed in the cylinder holder 131. When the notch 133 is formed in the rectangular shape in which the long side is along one side of the imaging element 33, the plurality of optical fibers 59 can be efficiently placed and processing can be facilitated. In a case where the optical fiber 59 has an outer diameter of 0.052 mm in the endoscope 11 according to the tenth configuration example, for example, six on one side, that is, 12 on both sides, can be accommodated at least in the direction along the chord of the half-moon columnar-shaped portion. The required number may vary with the object of observation, the distance to the object of observation, and the light source that is used.

In the endoscope 11 according to the tenth configuration example, the plurality of light guides 57 is placed substantially in point symmetry with respect to the lens center.

The light guides 57 are placed in point symmetry with respect to the lens center of the lens 93 in this endoscope 11, and thus illumination light can be distributed upward, downward, leftward, and rightward in a uniform manner when the circular inner peripheral surface is illuminated with the illumination light in particular. As a result, a shadow is unlikely to be created from the subject and the captured image becomes more likely to be seen. Since the light guide 57 is in point symmetry with respect to the axis of the tip portion 15, distribution of the illumination light is unlikely to change depending on the rotation angle of the tip portion 15 as well, and operability is improved during a movement into the blood vessel with a small diameter or the like in particular.

In the endoscope 11 according to the tenth configuration example, the plurality of optical fibers 59 is placed in parallel to the lens side surface along the lens center of the lens 93 and is arranged in a row along one side of the lens 93.

In this endoscope 11, the optical fiber 59 can be vertically placed along one side of the lens 93. As a result of this configuration, effective space utilization 59 can be conducted compared to placement of the optical fiber only at the center of one side. In addition, a wide range of the illumination light can be distributed in a uniform manner by the endoscope 11 because the plurality of optical fibers 59 is arranged in a row along one side.

In the cylinder holder 131, a square tube connecting portion 137 for ensuring the thickness of the sheath 61 may also be disposed to extend in a rear portion on the side opposite to the insertion tip surface 135. By the square tube connecting portion 137 being disposed, the cylinder holder 131 is capable of increasing the connection strength of the sheath 61. In other words, the sheath 61 can be thickened with the extrapolated part of the square tube connecting portion 137. In addition, it is preferable in terms of space efficiency improvement that a square hole 139 for accommodating the objective cover glass 91 that is drilled in the cylinder holder 131 is formed by being allowed to approach a cylinder outer peripheral circle to the maximum extent allowed by strength.

Accordingly, the space efficiency (member placement density) of the insertion tip surface 135 can be increased (suppression of useless space) in the endoscope 11 according to the tenth configuration example, and thus size reduction can be achieved, the lens 93 and the imaging element 33 can be easily fixed with a high level of strength, and stray light from the light guide 57 can be prevented as well.

In the insertion tip surface 135 of the endoscope 11, the space between the sheath 61 and the camera Assy and the fiber Assy is filled without a gap with the adhesive resin 37, and thus penetration of the tip portion 15 by a liquid can be prevented and washing can be facilitated.

Eleventh Configuration Example

Figure 26:
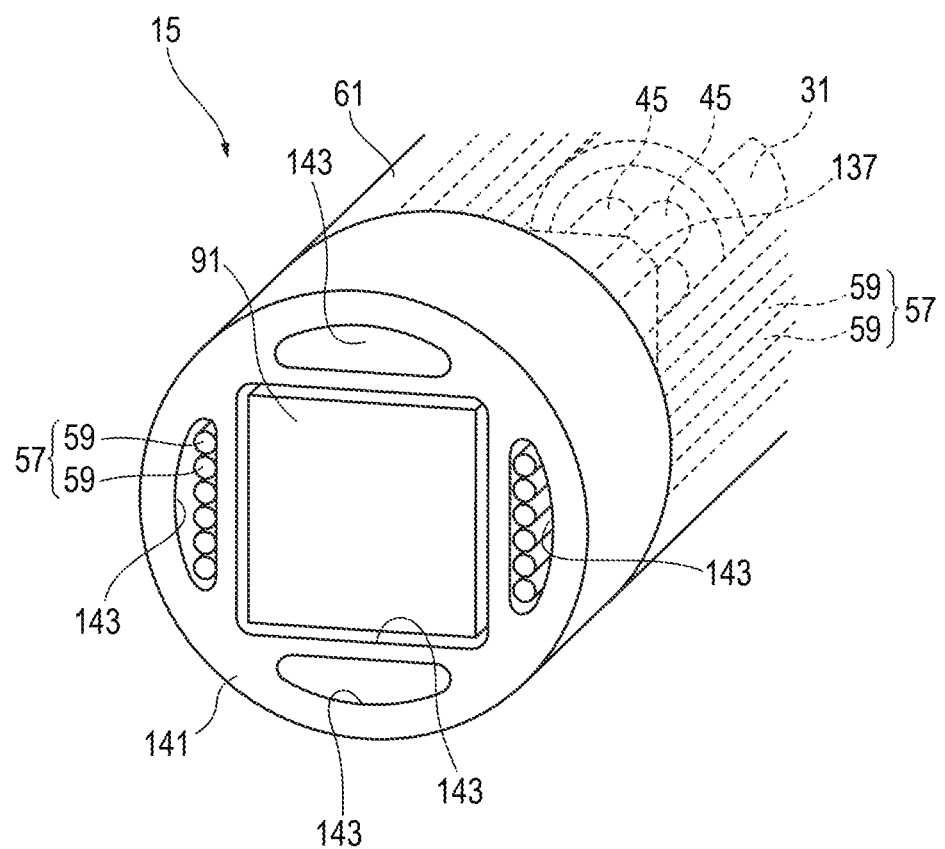
FIG. 26 is an enlarged perspective view of the main part, in which the light-shielding member of the endoscope according to the present embodiment is a through-holed holder.
Figure 27:
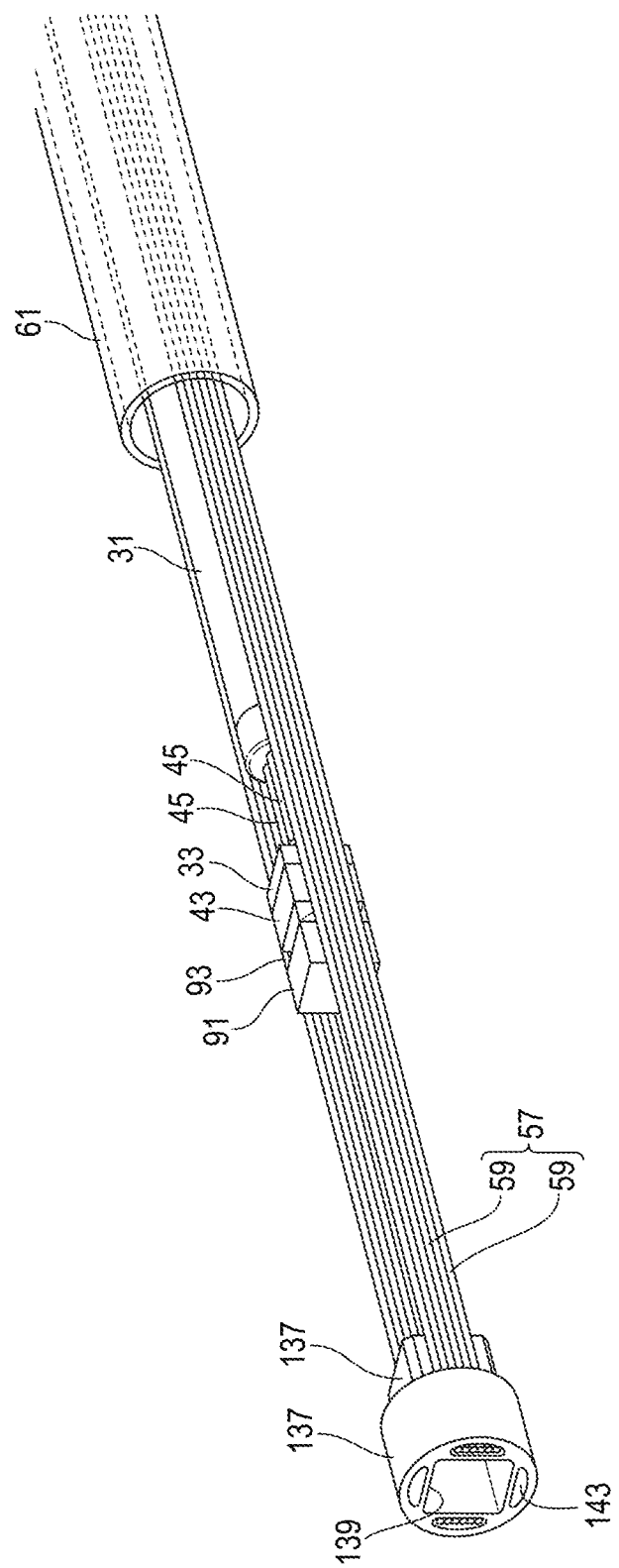
FIG. 27 is an exploded perspective view of the endoscope illustrated in FIG. 26.

FIG. 26 is an enlarged perspective view of the main part, in which the light-shielding member of the endoscope 11 according to the present embodiment is a through-holed holder. FIG. 27 is an exploded perspective view of the endoscope 11 illustrated in FIG. 26.

The light-shielding member in the endoscope 11 according to the eleventh configuration example is a cylinder holder 141 that coaxially accommodates the lens 93 and a through-hole 143 in a direction along the lens center is formed between one side of the lens 93 and the holder outer peripheral surface of the cylinder holder 141. The plurality of optical fibers 59 is inserted into the through-hole 143. In a case where the optical fiber 59 has an outer diameter of 0.052 mm in the endoscope 11 according to the eleventh configuration example, for example, six on one side, that is, 12 on both sides, can be accommodated at least in the direction along the chord of the through-hole 143. The required number may vary with the object of observation, the distance to the object of observation, and the light source that is used.

This endoscope 11 is assembled as follows. Specifically, a camera Assy is completed by assembly of the lens 93, the imaging element 33, and the transmission cable 31 illustrated in FIG. 27. Then, a fiber Assy is assembled by the plurality of light guides 57 being attached to the cylinder holder 141. The fiber Assy is made up of, for example, the plurality of light guides 57 and the cylinder holder 141 as an example of the light-shielding member. The plurality of light guides 57 is inserted into and fixed to the through-hole 143 of the cylinder holder 141. Then, the camera Assy is mounted on the cylinder holder 141 of the fiber Assy. Likewise, a distance of approximately 50 (μm) or more is ensured between one side of the objective cover glass 91 and the through-hole 143. Finally, the cylinder holder 141 is wrapped with the sheath 61 and the gaps between the sheath 61 and the camera Assy and the fiber Assy are filled with the adhesive resin 37 to be fixed.

In the endoscope 11 according to the eleventh configuration example, the through-hole 143 in the direction along the lens center is formed in the half-moon columnar-shaped portion in the cylinder holder 141 as a square hole tube. The through-hole 143 is a hole that has a substantially half-moon shape with the chord in the direction along one side, and thus the light guide 57 can be efficiently placed.

The gaps (including the through-holes 143) that are attributable to the fixing of the camera Assy and the fiber Assy in the insertion tip surface of the endoscope 11 are filled with the adhesive resin 37, and thus penetration of the tip portion 15 by a liquid can be prevented and washing can be facilitated.

Twelfth Configuration Example

Figure 28:
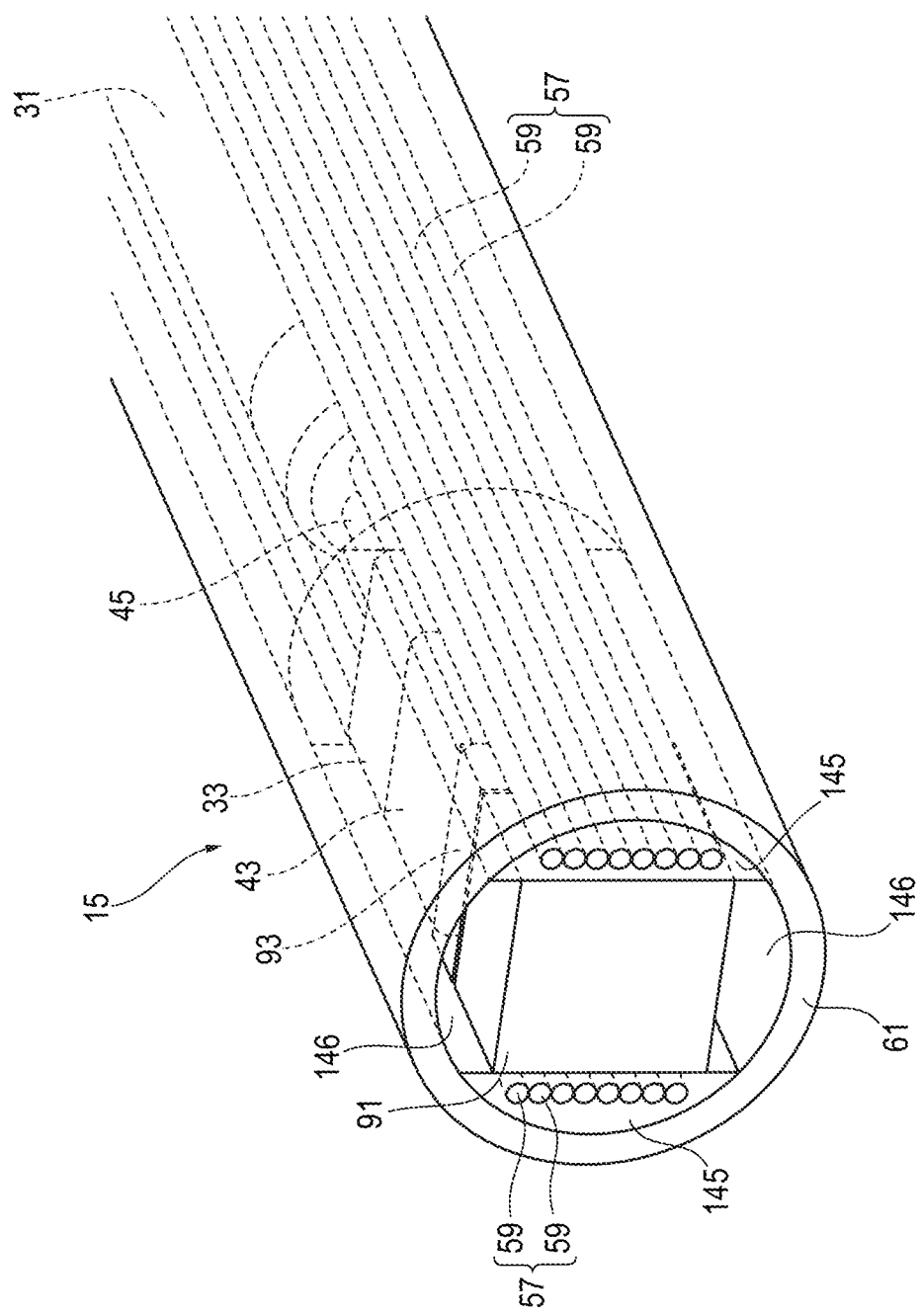
FIG. 28 is an enlarged perspective view of the main part, in which the light-shielding member of the endoscope according to the present embodiment is a resin mold.
Figure 29:
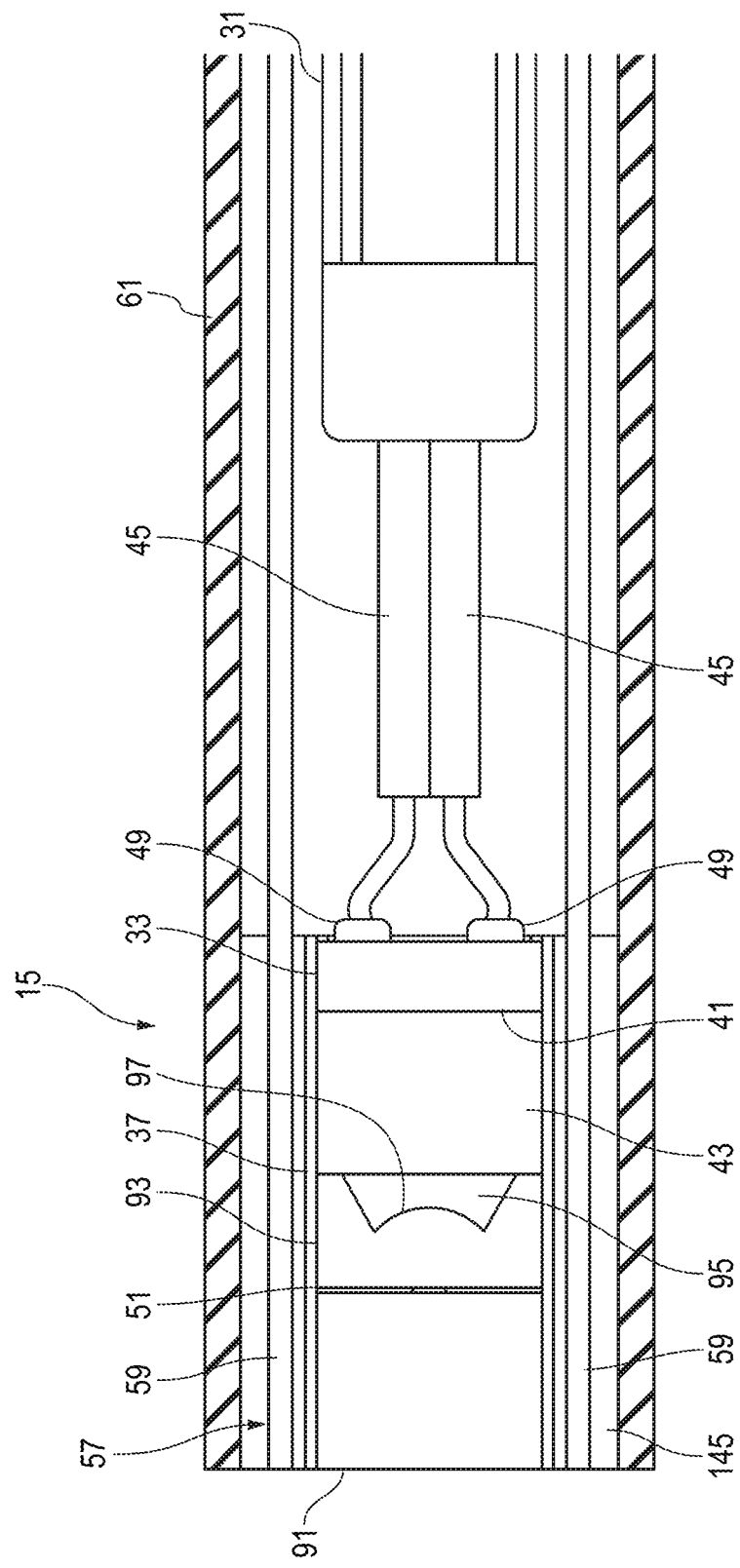
FIG. 29 is a plan sectional view of the endoscope illustrated in FIG. 28.
Figure 30:
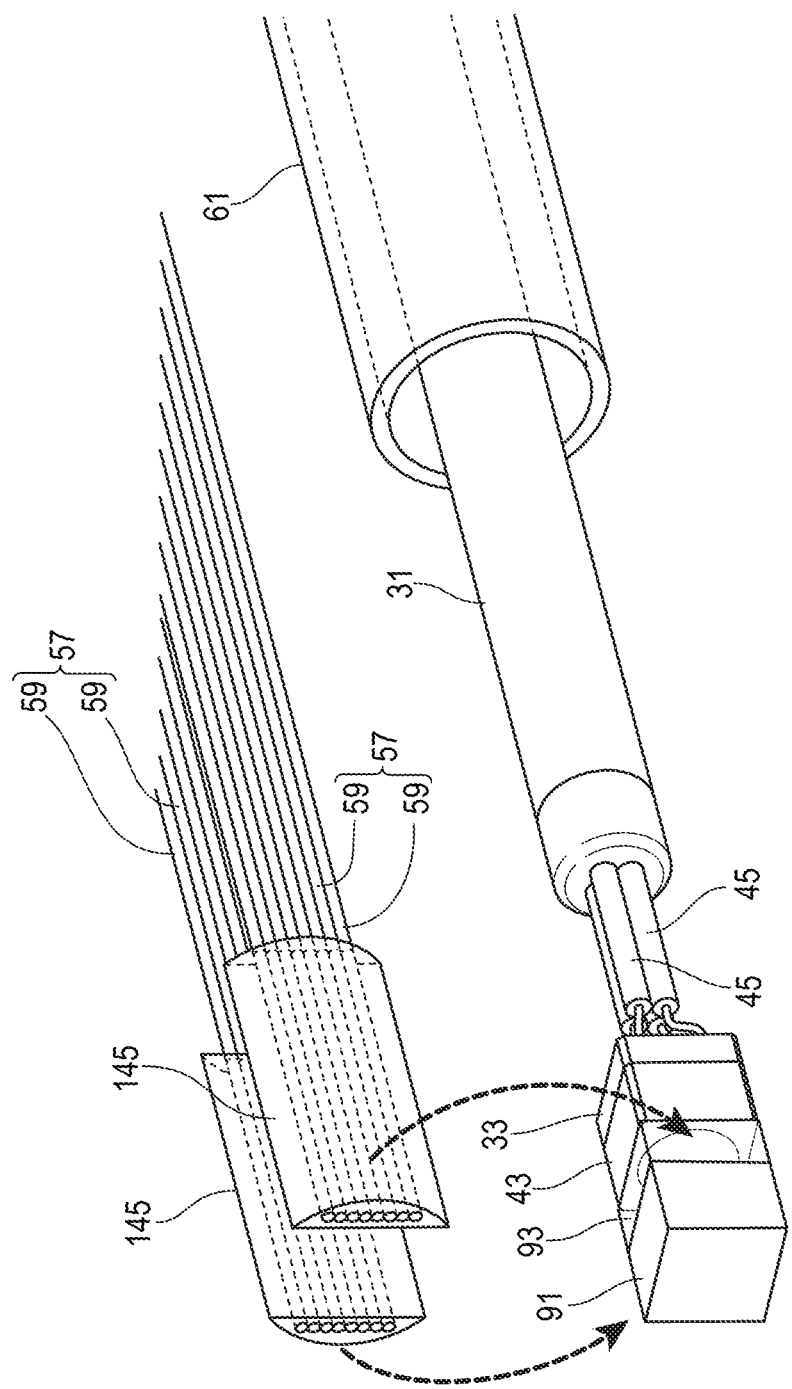
FIG. 30 is an exploded perspective view of the endoscope illustrated in FIG. 28.

FIG. 28 is an enlarged perspective view of the main part, in which the light-shielding member of the endoscope 11 according to the present embodiment is a mold resin. FIG. 29 is a plan sectional view of the endoscope 11 illustrated in FIG. 28. FIG. 30 is an exploded perspective view of the endoscope 11 illustrated in FIG. 28.

The light-shielding member in the endoscope 11 according to the twelfth configuration example is a mold resin 145 that covers the extension-direction outside surface of the light guide 57.

This endoscope 11 is assembled as follows. Specifically, a camera Assy is completed by assembly of the lens 93, the imaging element 33, and the transmission cable 31 illustrated in FIG. 30. Then, a fiber Assy is completed by resin molding. Then, the fiber Assy is fixed to the camera Assy (refer to the dotted line). Finally, the fiber Assy to which the camera Assy fixed is covered with the sheath 61 from its outside and the gaps between the fiber Assy and the camera Assy and the sheath 61 are filled with a mold resin 146, which results in fixing without a gap.

In the endoscope 11 according to the twelfth configuration example, the plurality of optical fibers 59 that constitutes the light guide 57 is allowed to form a fiber bundle by the mold resin 145. The plurality of optical fibers 59 is arranged in a row along one side of the lens 93. In a case where the optical fiber 59 has an outer diameter of 0.052 mm in the endoscope 11 according to the twelfth configuration example, for example, eight on one side, that is, 16 on both sides, can be accommodated at least in the direction along the chord. The mold resin 145 is molded in the same shape as the half-moon columnar-shaped portion at the position of any one of the four half-moon columnar-shaped portions described above. Regarding the mold resin 145, molten resin filling is performed by the resin mold being used with the optical fiber 59 placed in a cavity already filled with molten resin. In this manner, the plurality of optical fibers 59 is integrally molded in the half-moon columnar-shaped portion in a state where the optical fibers 59 are arranged in a row and inserted.

In a case where it is feared that light will leak from the extension-direction outside surface of the optical fiber 59 due to a decrease in thickness, a carbon-containing resin (such as a carbon black-containing resin) can be used for the mold resin 145. In addition, a vapor deposited metallic film or the like or a screen printing-based on light-shielding film may be formed on the lens side surface. In this manner, its light-shielding performance can be further enhanced despite the light-shielding member being the mold resin 145. In the insertion tip surface of the endoscope 11, the space between the sheath 61 and the camera Assy and the fiber Assy is filled without a gap with the mold resin 146, and thus penetration of the tip portion 15 by a liquid can be prevented and washing can be facilitated.

Thirteenth Configuration Example

Figure 31:
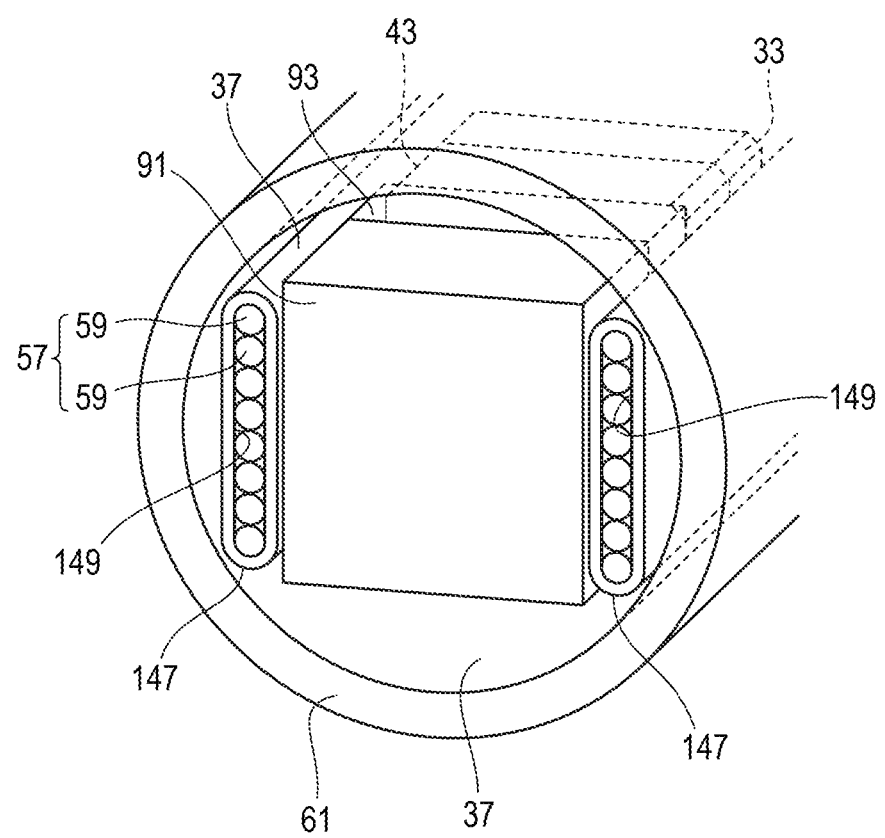
FIG. 31 is an enlarged perspective view of the main part, in which the light-shielding member of the endoscope according to the present embodiment is a pipe.
Figure 32:
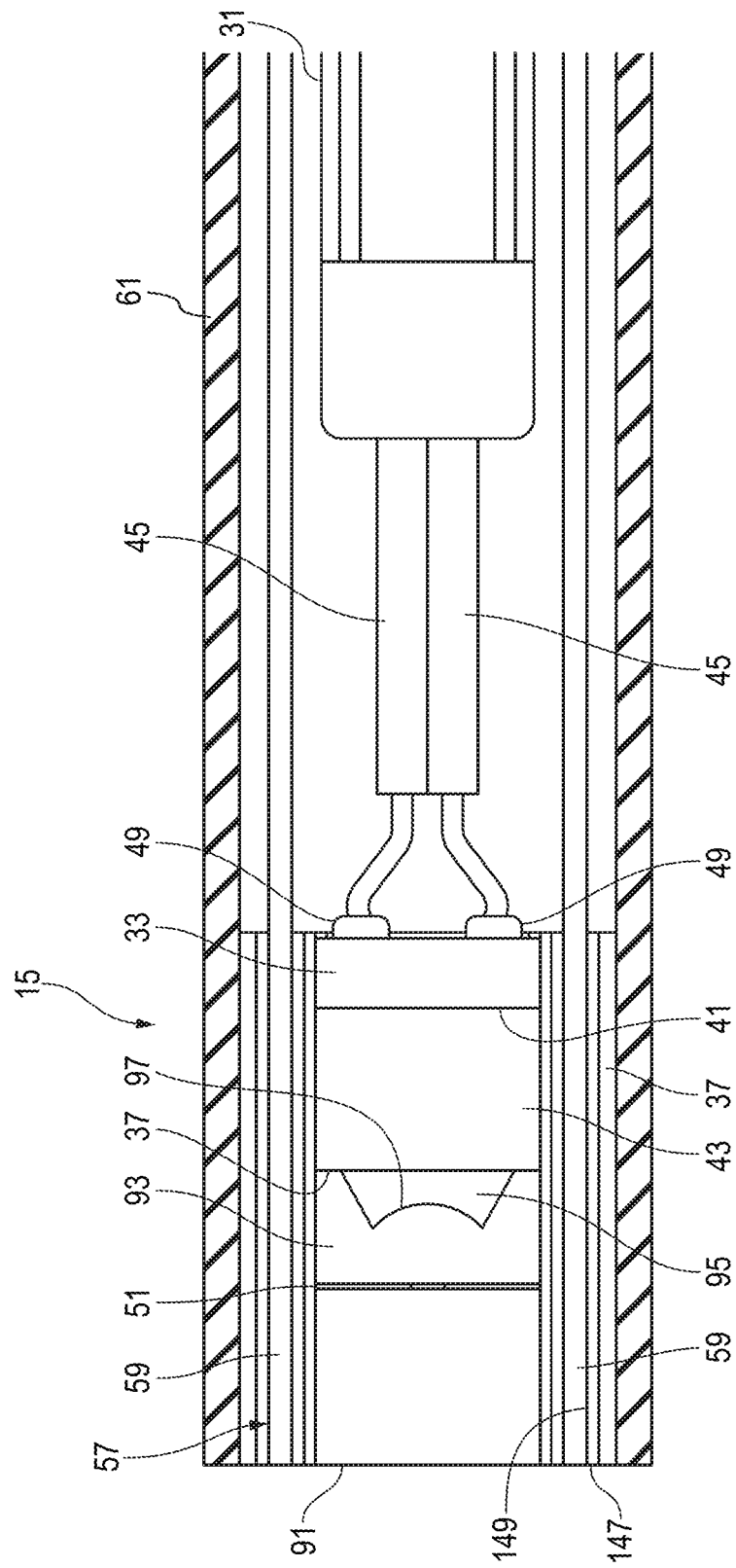
FIG. 32 is a plan sectional view of the endoscope illustrated in FIG. 31.
Figure 33:
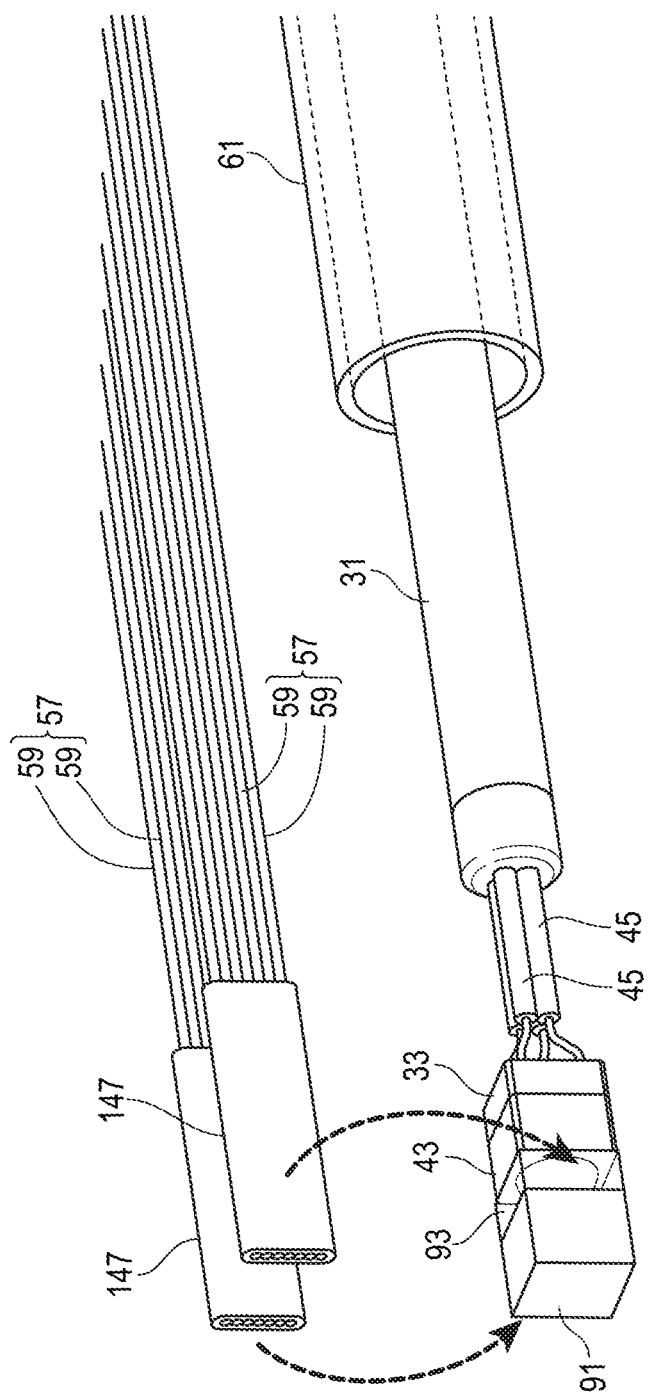
FIG. 33 is an exploded perspective view of the endoscope illustrated in FIG. 31.

FIG. 31 is an enlarged perspective view of the main part, in which the light-shielding member of the endoscope 11 according to the present embodiment is a pipe 147. FIG. 32 is a plan sectional view of the endoscope 11 illustrated in FIG. 31. FIG. 33 is an exploded perspective view of the endoscope 11 illustrated in FIG. 31.

In the endoscope 11 according to the thirteenth configuration example, the light-shielding member is the pipe 147 that is inserted into the light guide 57.

This endoscope 11 is assembled as follows. Specifically, a camera Assy is completed by assembly of the lens 93, the imaging element 33, and the transmission cable 31 illustrated in FIG. 33. Then, a fiber Assy is assembled by the optical fiber 59 being inserted into the pipe 147 and fixed without a gap by the adhesive resin 37. Then, the fiber Assy is fixed without a gap by the adhesive resin 37 to a facing side surface of the camera Assy. Finally, the outside of the fiber Assy fixed to the camera Assy is covered by the sheath 61 inserted into the transmission cable 31 and the gaps between the sheath 61 and the camera Assy and the fiber Assy are filled with the adhesive resin 37 to be fixed. The adhesive resin 37 is not illustrated in FIG. 31. Still, the gaps between the sheath 61 and the camera Assy and the fiber Assy are filled with the adhesive resin 37. Although the adhesive resin 37 is illustrated in FIG. 32 as providing adhesion at least up to the terminal end face of the imaging element 33 (that is, the terminal end face of the pipe 147), the range of adhesion of the adhesive resin 37 is not limited to the range of up to the terminal end face of the imaging element 33. For example, the adhesive resin 37 may provide adhesion including parts of the conductor connection portion 49, the electric wire 45, and the transmission cable 31 further on the rear end side than the terminal end face of the imaging element 33 (that is, the side opposite to the objective side) in the sheath 61.

In the endoscope 11 according to the thirteenth configuration example, the plurality of optical fibers 59 that constitutes the light guide 57 can be shielded by insertion into an oval hole 149 of the pipe 147. In a case where the optical fiber 59 has an outer diameter of 0.052 mm in the endoscope 11 according to the thirteenth configuration example, for example, eight on one side, that is, 16 on both sides, can be accommodated at least in the direction along the oval hole 149. The pipe 147 is formed as an elongated cylinder. A Ni electroforming material or the like can be used as a material of the pipe 147. A minor axis of the elongated cylinder substantially corresponds to the outer diameter of the optical fiber 59. Accordingly, the pipe 147 allows the plurality of optical fibers 59 to be arranged in a row in a major-axis direction and bundled up. It is preferable that the optical fiber 59 inserted into the pipe 147 is fixed by the adhesive resin 37 described above. This pipe 147 is capable of having a surface in the direction along a long axis fixed to the lens side surface. Because the elongated and cylindrical pipe 147 is used as the light-shielding member, shielding and bundling of the plurality of optical fibers 59 can be performed with ease, reliability, and a high level of strength. In the tip surface of the endoscope 11, the space between the sheath 61 and the camera Assy and the fiber Assy is filled without a gap with the adhesive resin 37, and thus penetration of the tip portion 15 by a liquid can be prevented and washing can be facilitated.

Fourteenth Configuration Example

Figure 34:
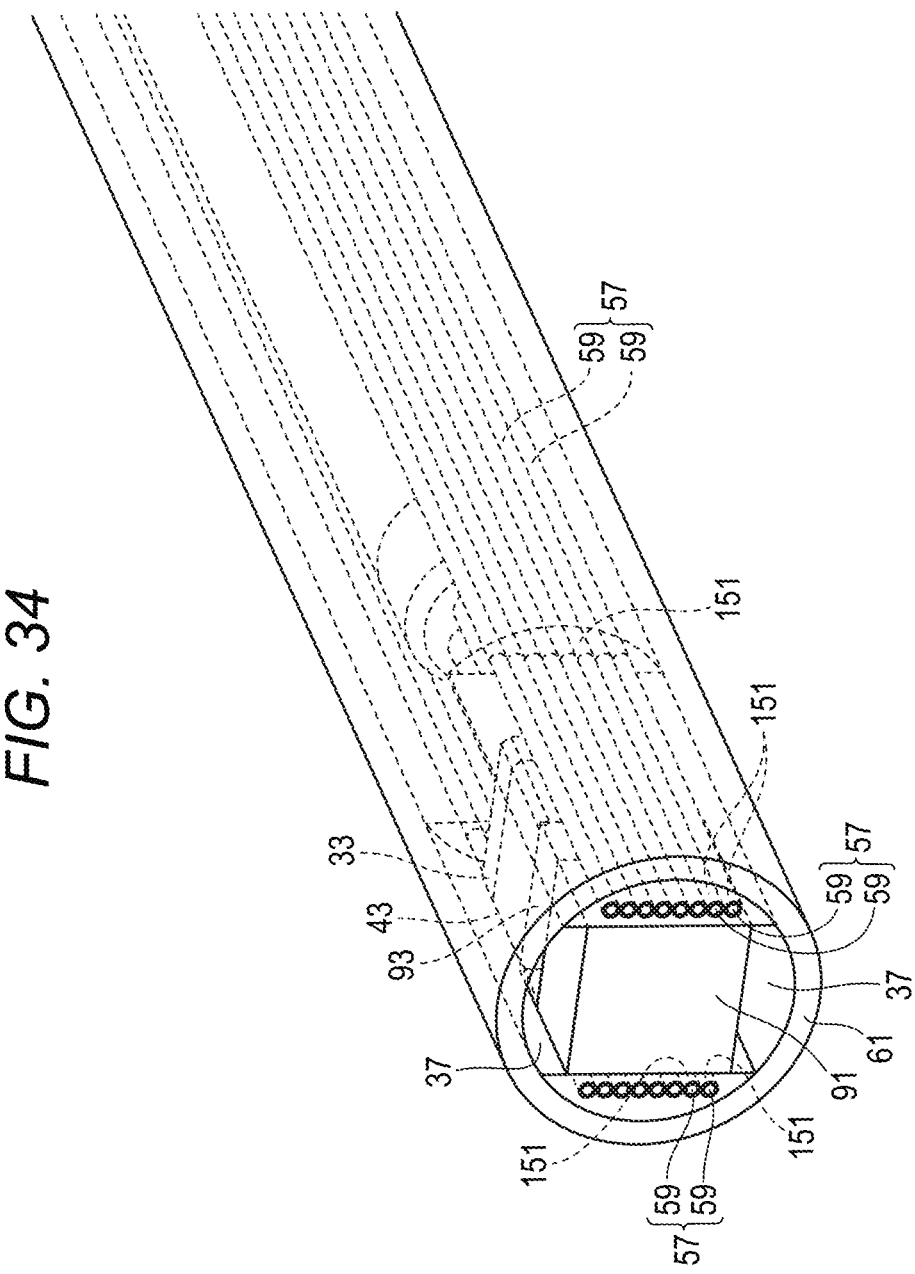
FIG. 34 is an enlarged perspective view of the main part, in which the light-shielding member of the endoscope according to the present embodiment is a jacket.
Figure 35:
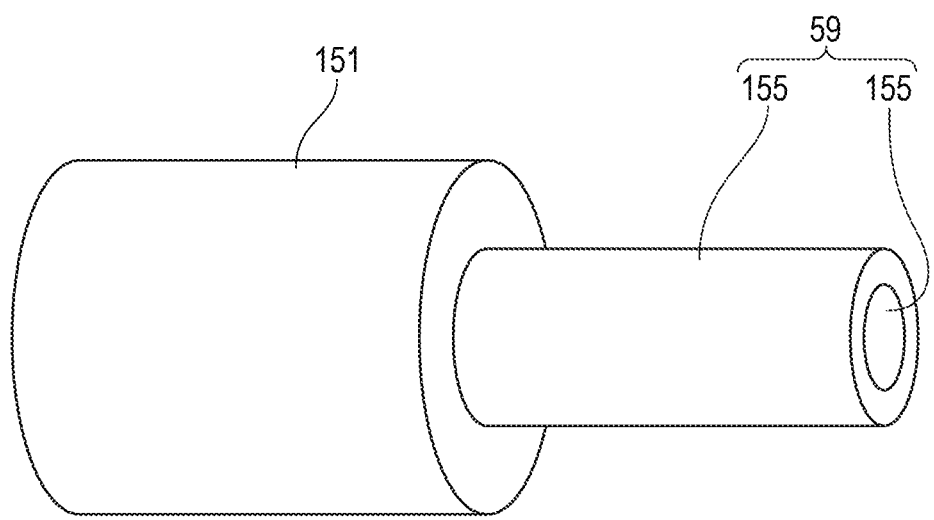
FIG. 35 is an enlarged perspective view of an optical fiber covered by the jacket.

FIG. 34 is an enlarged perspective view of the main part, in which the light-shielding member of the endoscope according to the present embodiment is a jacket 151. FIG. 35 is an enlarged perspective view of the optical fiber 59 covered by the jacket 151 in FIG. 34.

The endoscope 11 according to the fourteenth configuration example is provided with a single lens (such as the lens 93) that has a quadrangular outer shape (such as a square shape and a rectangular shape) in the direction perpendicular to the optical axis or the lens center, the sheath 61 placed coaxially with respect to the optical axis or the lens center and surrounding the lens 93 with the surrounding outer periphery having a circular shape, the lighting member (such as the light guide 57) placed between the outer periphery of the sheath 61 and at least one side of the lens 93 and extending along the optical axis or the lens center, and the light-shielding member disposed between the lens 93 and the light guide 57. The light-shielding member is the jacket 151 covering the extension-direction outside surface of the light guide 57. The jacket 151 is disposed for each of the optical fibers 59 constituting the light guide 57. The endoscope 11 according to the fourteenth configuration example further includes the imaging element 33 that has a quadrangular outer shape (such as a square shape and a rectangular shape) in the direction perpendicular to the optical axis or the lens center with the length of its one side being equal to the length of one side of the lens 93 and the element cover glass 43 covering the imaging surface 41 of the imaging element 33 and having the same outer shape as the imaging element 33 in the direction perpendicular to the optical axis or the lens center.

This endoscope 11 is assembled as follows. Specifically, a camera Assy is completed by assembly of the lens 93, the imaging element 33, and the transmission cable 31 illustrated in FIG. 30. Then, a fiber Assy including the plurality of optical fibers 59 where the jackets 151 are disposed is completed by resin molding. Then, the fiber Assy is fixed to the camera Assy (refer to the dotted line). Finally, the fiber Assy to which the camera Assy fixed is covered with the sheath 61 from its outside and the gaps between the fiber Assy and the camera Assy and the sheath 61 are filled with the mold resin 146, which results in fixing without a gap. The mold resin 146 in the gaps between the fiber Assy and the camera Assy and the sheath 61 is not illustrated in FIG. 34. Still, the gaps between the fiber Assy and the camera Assy and the sheath 61 are filled with the mold resin 146. Although the mold resins 145 and 146 are illustrated in FIG. 34 as providing coating at least up to the terminal end face of the imaging element 33, the range of coating of the mold resins 145 and 146 is not limited to the range up to the terminal end face of the imaging element 33. For example, the mold resins 145 and 146 may provide coating and fixing including parts of the conductor connection portion 49, the electric wire 45, and the transmission cable 31 further on the rear end side than the terminal end face of the imaging element 33 (that is, the side opposite to the objective side) in the sheath 61.

In the endoscope 11 according to the fourteenth configuration example, the extension-direction outside surface of each of the optical fiber 59s is covered by the cylindrical jacket 151. A highly light-shielding material is used for the jacket 151. Examples of the highly light-shielding material can include a carbon-containing resin.

In general, quartz glass and resin are used for a core 153 and cladding 155 of the optical fiber 59. The light condensing capability of the optical fiber 59 increases and bonding with a light source becomes easier as its maximum acceptance angle NA (numerical aperture: number of openings) increases. Still an increase in NA leads to an increase in optical loss and light dispersion between the core 153 and the cladding 155. Accordingly, an optimum NA value needs to be obtained. Since the jacket 151 is disposed on the optical fiber 59, light leaking that arises in a case where the optimum NA value is set can be reliably blocked with a simple structure.

Fifteenth Configuration Example

The endoscope according to the fifteenth configuration example (not illustrated) is provided with a single lens (such as the lens 93) that has a quadrangular outer shape (such as a square shape and a rectangular shape) in the direction perpendicular to the optical axis or the lens center, a sheath (such as the sheath 61) placed coaxially with respect to the optical axis or the lens center and surrounding the lens with the surrounding outer periphery having a circular shape, the lighting member (such as the light guide 57) placed between the outer periphery of the sheath and at least one side of the lens and extending along the optical axis or the lens center, and the light-shielding member disposed between the lens and the light guide. The light-shielding member is a light-shielding film (not illustrated) formed on the lens side surface along the lens center of the lens. The endoscope 11 according to the fifteenth configuration example further includes the imaging element 33 that has a quadrangular outer shape (such as a square shape and a rectangular shape) in the direction perpendicular to the optical axis or the lens center with the length of its one side being equal to the length of one side of the lens 93 and the element cover glass 43 covering the imaging surface 41 of the imaging element 33 and having the same outer shape as the imaging element 33 in the direction perpendicular to the optical axis or the lens center. In the endoscope 11 according to the fifteenth configuration example, leaking light from the light guide 57 may be blocked by member of an appropriate combination with the configuration of the endoscope according to the tenth to fourteenth configuration examples between the sheath 61 and the light guide 57 and between the sheath 61 and the objective cover glass 91, the lens 93, the element cover glass 43, and the imaging element 33.

Since the light-shielding film is formed on the lens side surface in the endoscope 11 according to the fifteenth configuration example, incidence of light leaking from the extension-direction outside surface of the optical fiber placed in its vicinity toward the lens side surface is prevented. The light-shielding film can be formed by vacuum deposition. During the vacuum deposition, a film-forming material goes through evaporation and sublimation in a vacuum and its particles are subjected to adhesion and deposition. Examples of the film-forming material can include aluminum, chromium, and gold.

In the tenth to fourteenth configuration examples described above, the maximum outer diameter Dmax is 1 mm or less. The maximum outer diameter Dmax of the endoscope 11 may be less than 2 mm (such as 1.8 mm) as well. One side of the imaging element 33 has a maximum length of 0.51 mm and the thickness of the imaging element 33 is 0.51 mm. The optical fiber 59 has a maximum outer diameter of 0.052 mm. The light guides 57 as the lighting member are placed at, for example, two respective places in point symmetry.

Sixteenth Configuration Example

Figure 36:
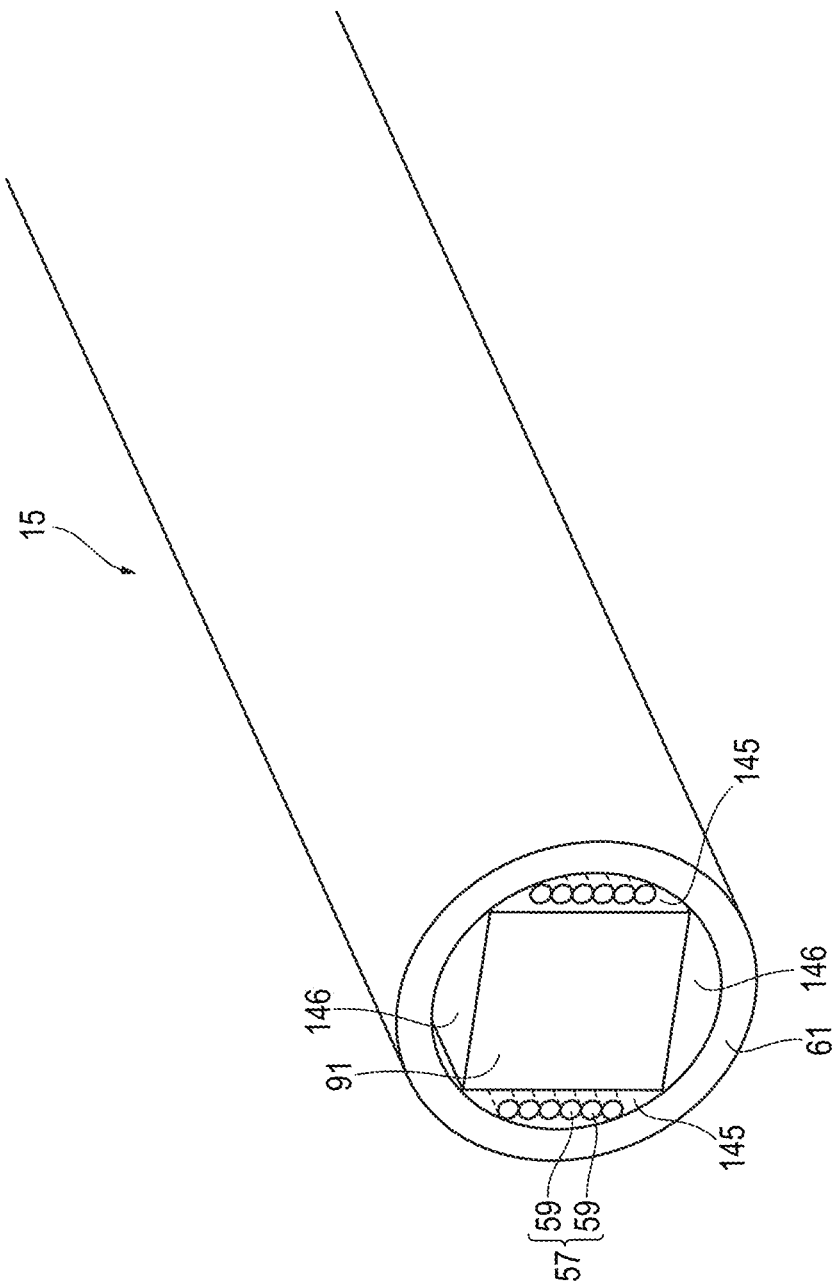
FIG. 36 is a perspective view of the tip portion of the endoscope according to the present embodiment in which the imaging element and a sheath are substantially in contact with each other and four corners of the imaging element are not chamfered.
Figure 37:
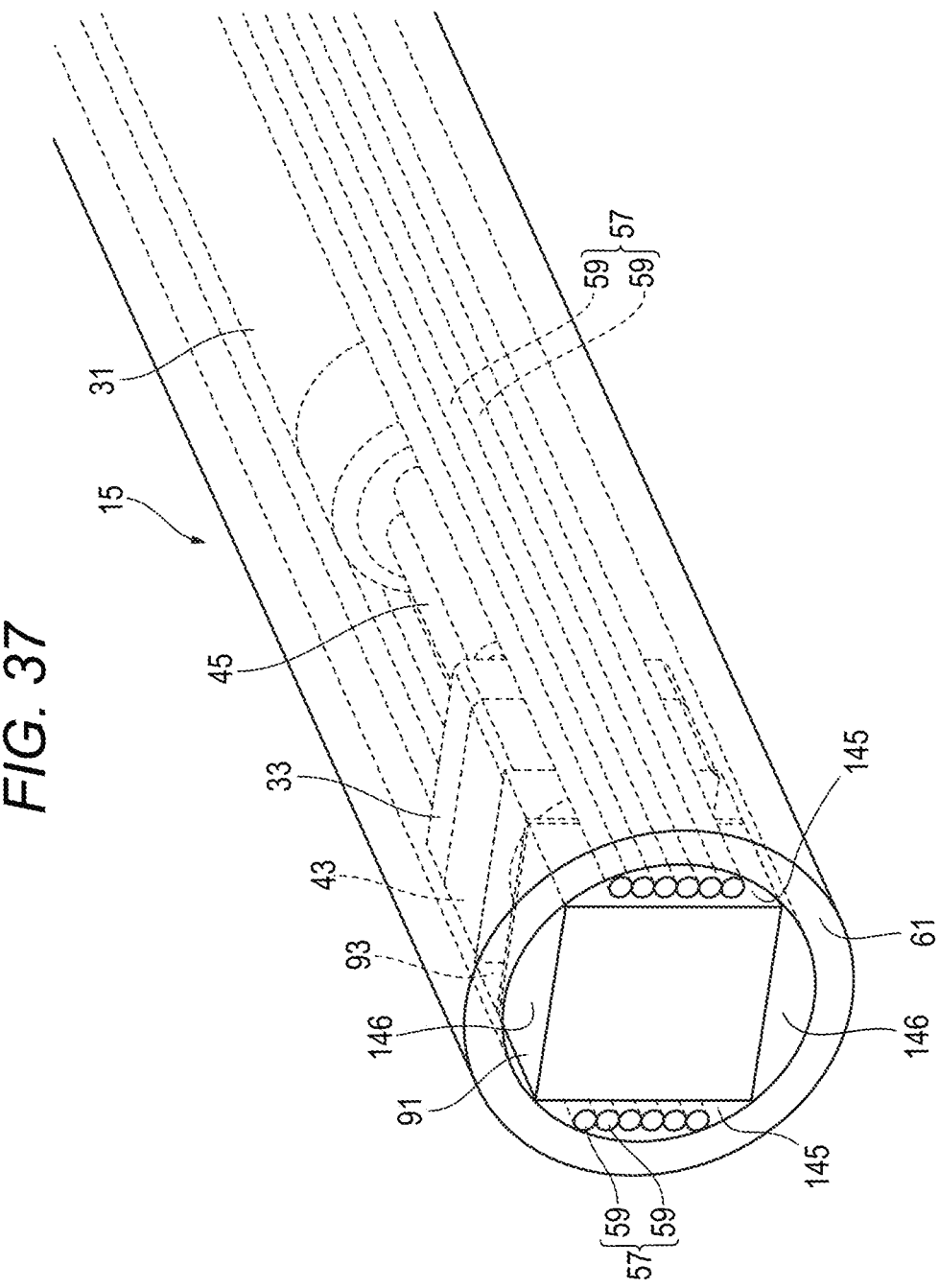
Figure 38:
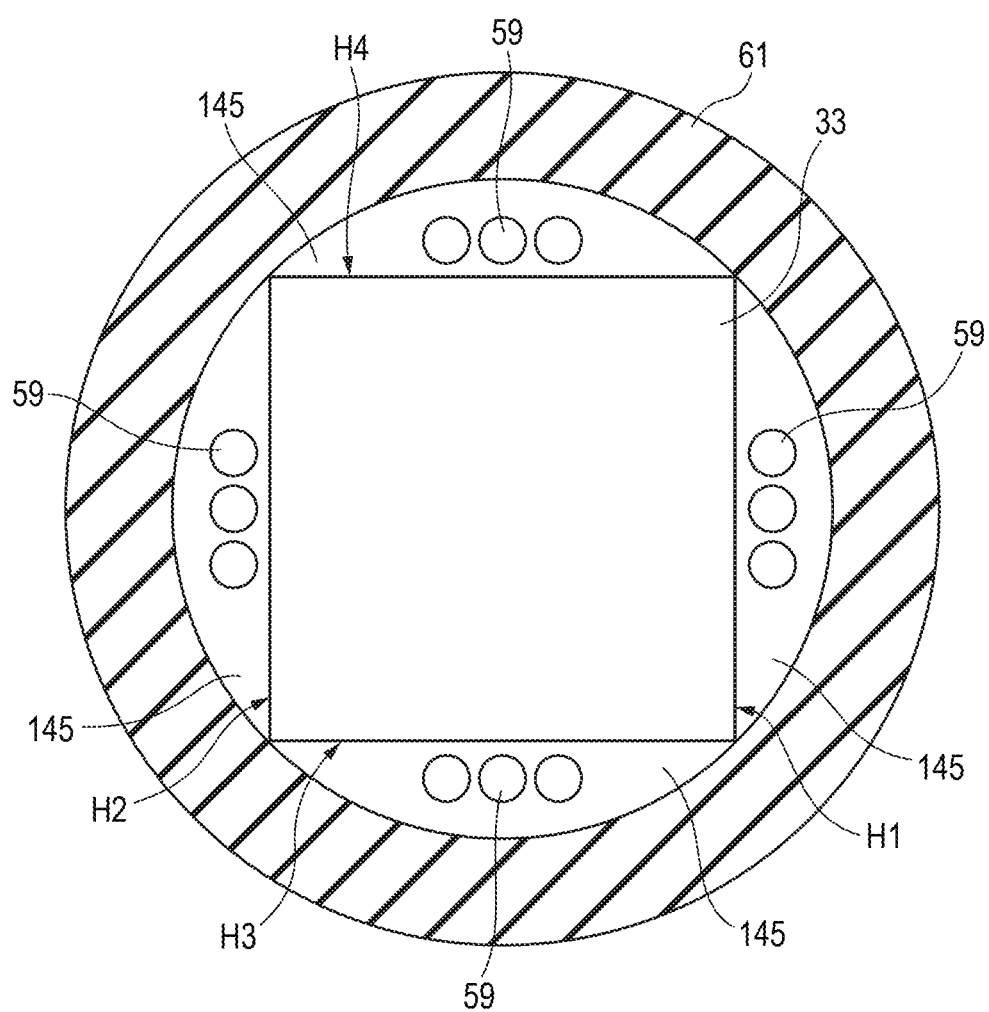
FIG. 38 is a front sectional view including the imaging element of the endoscope illustrated in FIG. 36.

FIG. 36 is a perspective view of the tip portion 15 of the endoscope 11 according to the present embodiment in which the imaging element 33 and the sheath 61 are substantially in contact with each other and the four corners of the imaging element 33 are not chamfered. FIG. 37 is a perspective view in which the sheath 61 of the endoscope 11 illustrated in FIG. 36 is seen through. FIG. 38 is a front sectional view including the imaging element 33 of the endoscope 11 illustrated in FIG. 36. The front sectional view shows the appearance of the section perpendicular to the axial direction through the optical axis or the lens center.

FIG. 29 described above can also be used as a plan sectional view of the endoscope 11 illustrated in FIG. 36. When FIG. 29 is applied to the present configuration example, the thickness of the mold resin with which the gap between the imaging element 33 and the sheath 61 is filled is reduced as the gap is narrowed based on the substantial contact between the imaging element 33 and the sheath 61.

Description of the configuration of the present configuration example that is similar to those of the configuration examples described above may be omitted or provided in a simplified manner.

The endoscope according to the sixteenth configuration example is provided with a single lens (such as the lens 93) that has a substantially quadrangular outer shape (such as a square shape and a rectangular shape) in the direction perpendicular to the optical axis or the lens center. The endoscope 11 is provided with the imaging element 33 that has a substantially quadrangular outer shape (such as a square shape and a rectangular shape) in the direction perpendicular to the lens center with the length of its one side being equal to the length of one side of the single lens. The endoscope 11 is provided with the element cover glass 43 covering the imaging surface 41 of the imaging element 33 and having the same outer shape as the imaging element 33 in the direction perpendicular to the lens center. The endoscope 11 is provided with the sheath 61 placed coaxially with respect to the lens center, surrounding the respective outside surfaces of the single lens, the element cover glass 43, and the imaging element 33, and having a circular outer shape. The sheath 61 is substantially in contact with the imaging element 33.

This endoscope 11 is assembled as follows. Specifically, for example, a camera Assy is completed by assembly of the lens 93, the imaging element 33, and the transmission cable 31. Then, the light guide 57 including the plurality of optical fibers 59 is placed along at least one side of the members such as the imaging element 33, the element cover glass 43, the lens 93, and the objective cover glass 91 and fixed to the side by pasting or the like. Then, the covering with the sheath 61 is conducted from the outside of the light guide 57 fixed to the camera Assy. Finally, the gaps between the fiber Assy and light guide 57 and the sheath 61 are filled with the mold resins 145 and 146, which results in fixing without a gap.

Herein, being "substantially in contact" member that a tiny gap (void) may be present or absent at the position where the imaging element 33 and the sheath 61 are at the shortest distance from each other, that is, between the four corners (corner portions) of the imaging element 33 and the sheath 61.

In a case where the tiny void is present, assembly performance improvement is available during endoscope assembly. In other words, when the camera Assy and the fiber Assy are covered from the outsides with the sheath 61 during the assembly of the endoscope 11, hindrance to a smooth assembly of the sheath 61 attributable to the sheath 61 being caught by the imaging element 33 of the camera Assy or the fiber Assy can be suppressed.

In a case where the tiny void is absent, the four corners of the imaging element 33 and the sheath 61 are in contact with each other. In this case, a heat-shrinkable tube is used as the sheath 61. Gaps are present between the four corners of the imaging element 33 and the sheath 61 before, for example, heating in the assembly process described above. Once the sheath 61 is heated after the covering with the sheath 61 or the filling with the mold resin 146, the sheath 61 contracts and the four corners of the imaging element 33 and the inner peripheral surface of the sheath 61 abut against each other. The state of the abutting (such as whether the imaging element 33 and the sheath 61 are to be slightly in contact with each other or to be put into a state where they are completely in contact with each other) may be adjusted depending on, for example, the degree to which the sheath 61 is heated.

When the heat-shrinkable tube is used as described above, the diagonal length of the imaging element 33 and the length of the diameter of the sheath 61 can be substantially equal to each other. Then, the diameter of the tip portion 15 of the endoscope 11 can be further reduced.

The number of the outside surfaces that are present in the imaging element 33 is equal to the number of individual sides of the imaging element 33, and thus the number is four in a case where the imaging element 33 has a quadrangular outer shape.

A holder that holds the lens 93 and the imaging element 33 can be omitted from the endoscope 11 according to the sixteenth configuration example. Accordingly, a space that is equivalent to the holder can be removed. In addition, since the imaging element 33 and the sheath 61 are substantially in contact with each other, the diagonal length of the quadrangular sectional shape in a front view of the imaging element 33 and the length of the diameter of the circular section in a front view of the sheath 61 are substantially equal to each other, which contributes to a reduction in the diameter of the tip portion 15 of the endoscope 11.

Despite the absence of the holder, the sheath 61 is substantially in contact with the four corners of the imaging element 33 in the endoscope 11. Accordingly, the imaging element 33 is held with the position of the imaging element 33 fixed at a predetermined position in the plane direction perpendicular to the axial direction through the optical axis or the lens center of the lens 93. Since the surrounding by the sheath 61 covers the outside surfaces of the imaging element 33, the element cover glass 43, and the lens 93, strength improvement is available in the outer peripheries of the imaging element 33, the element cover glass 43, and the lens 93. Accordingly, an unintended deformation of the tip portion 15 can be suppressed even if an external force is generated with respect to the tip portion 15 of the endoscope 11.

With the endoscope 11 described above, both a reduction in the size of the endoscope 11 and an improvement in robustness in the tip portion 15 can be achieved.

In the endoscope 11, the sheath 61 and the lens 93 may be substantially in contact with each other as well while the sheath 61 is substantially in contact with the imaging element 33. This allows the position of the imaging element 33 and the sheath 61 to be fixed at predetermined positions in the plane direction perpendicular to the axial direction through the optical axis or the lens center of the lens 93. Alternatively, the sheath 61 and the lens 93 may be substantially in contact with each other instead of the sheath 61 being substantially in contact with the imaging element 33. The sheath 61 may also be substantially in contact with one or both of the element cover glass 43 and the objective cover glass 91.

In the endoscope 11, the objective cover glass 91 is placed further on the objective side than the lens 93 and it has the same outer shape as the lens 93 in the direction perpendicular to the lens center. The objective cover glass 91 and the sheath 61 are disposed substantially on the same plane on the insertion tip surface 135 of the tip portion 15 including the objective cover glass 91 and the lens 93.

In other words, the sheath 61 extends up to the tip of the tip portion 15 outside the lens 93, the element cover glass 43, and the imaging element 33. As a result, surrounding by the sheath 61 continues from the imaging element 33 on the back face side to the objective cover glass 91 at the tip of the tip portion 15, and thus robustness improvement is available up to the tip of the tip portion 15.

The endoscope 11 may also be provided with the lighting member (such as the light guide 57) placed along the lens center and inserted between the respective outside surfaces of the lens 93 and the imaging element 33 and the inner peripheral surface of the sheath.

This leads to member placement density improvement in the tip portion 15 of the endoscope 11 because the space resulting from the difference in shape between the part of the sheath 61 that has a circular section in the front view and the parts of the lens 93 and the imaging element 33 that have a quadrangular sectional shape in the front view can be used for the placement of the light guide 57. As a result, the subject can be illuminated with a useless space suppressed.

In addition, the space between the outside surface of each of the lens 93 and the imaging element 33 and the inner peripheral surface of the sheath 61 in the endoscope 11 may be filled with a mold portion (such as the mold resins 145 and 146). The mold resins 145 and 146 according to the twelfth configuration example are not illustrated in FIGS. 36 and 37. Still, it is filled with the mold resins 145 and 146 as in FIG. 28.

As a result, the robustness of the endoscope 11 can be maintained by the mold resins 145 and 146, with which the space between the sheath 61 and the imaging element 33 or the like is filled, with its diameter reduced by the sheath and the imaging element 33 or the like being substantially in contact with each other. Since the space between the sheath 61 and the imaging element 33 or the like is filled without a gap with the mold resin, the waterproofness and dustproofness of the endoscope 11 can be improved as well.

Seventeenth Configuration Example

Figure 39:
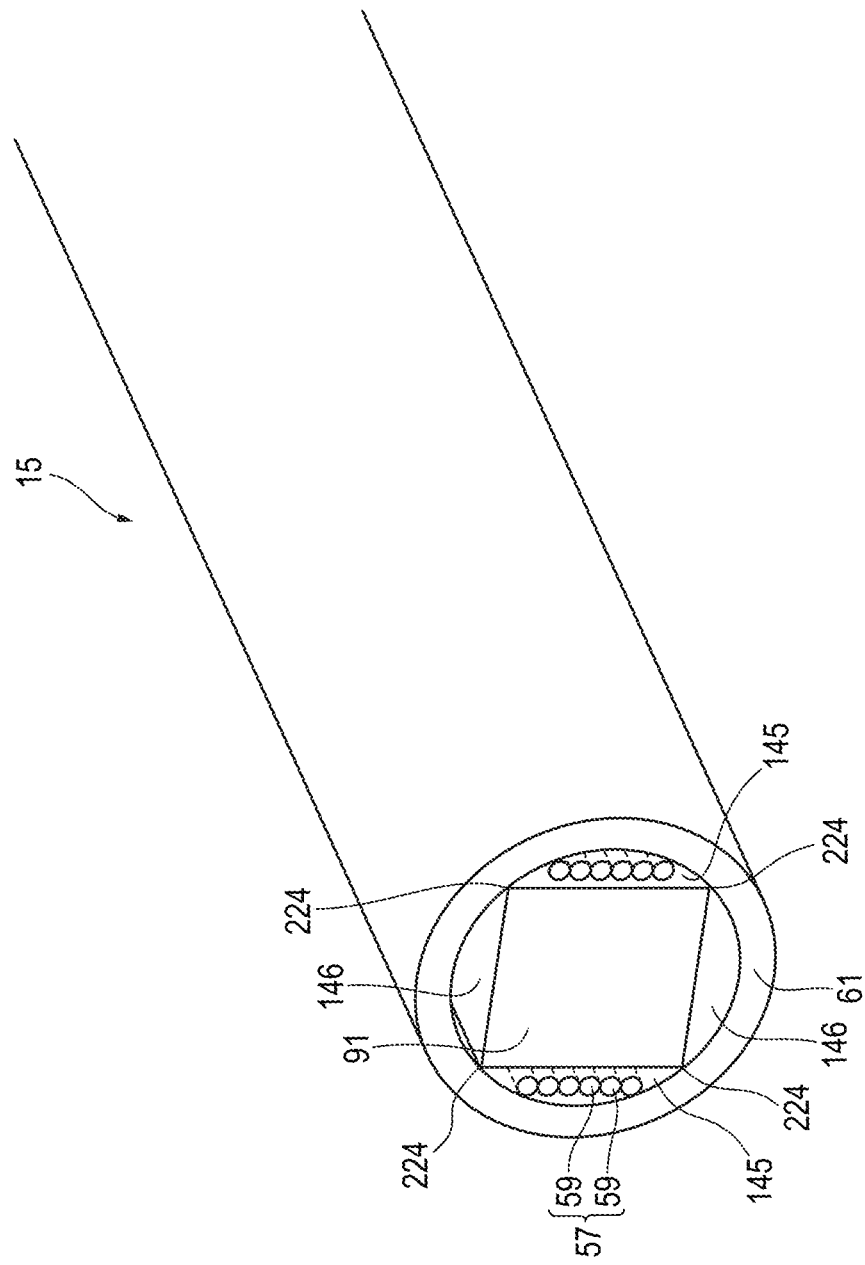
FIG. 39 is a perspective view of the tip portion of the endoscope according to the present embodiment in which the imaging element and the sheath are substantially in contact with each other and the four corners of the imaging element are chamfered.
Figure 40:
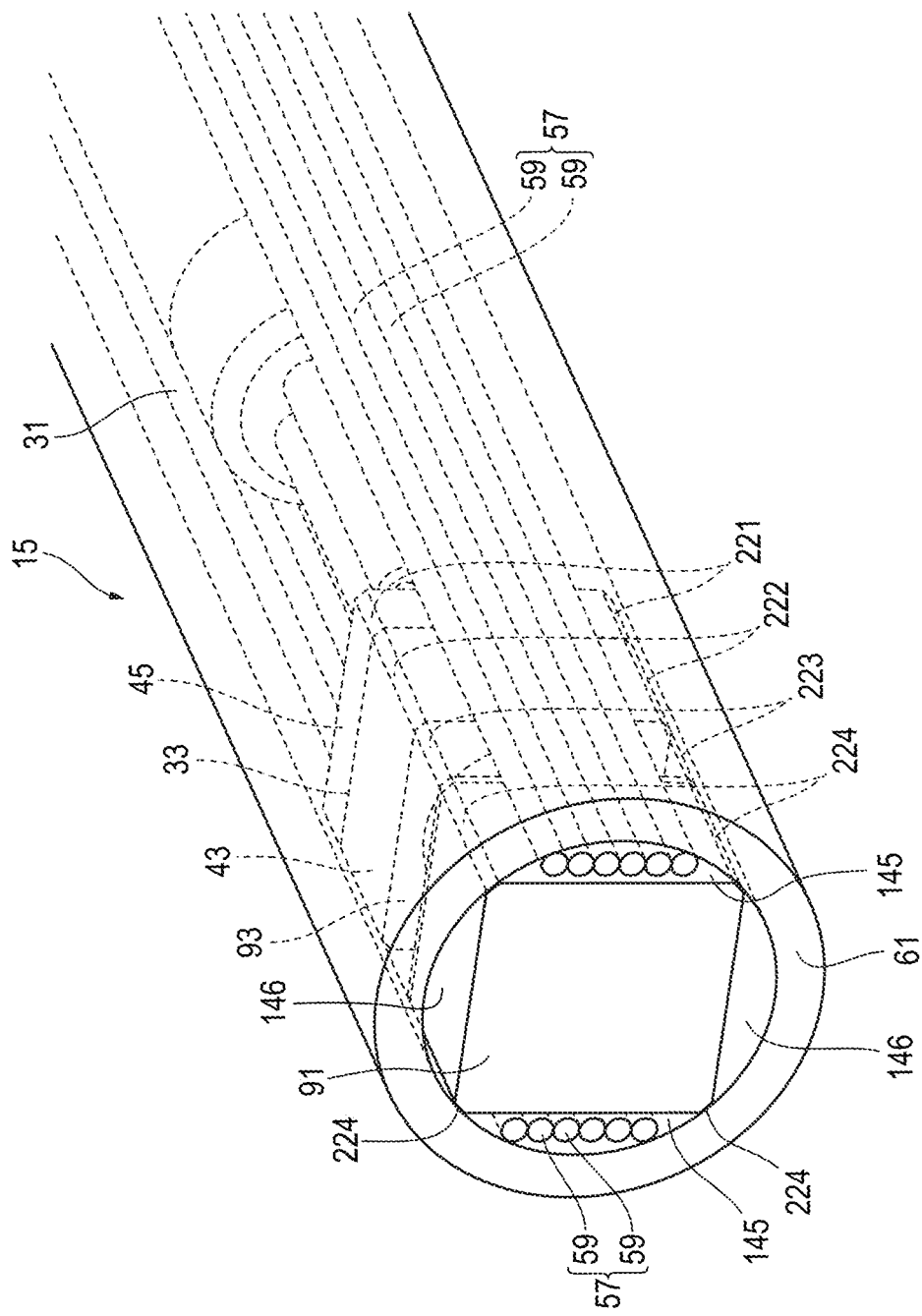
Figure 41:
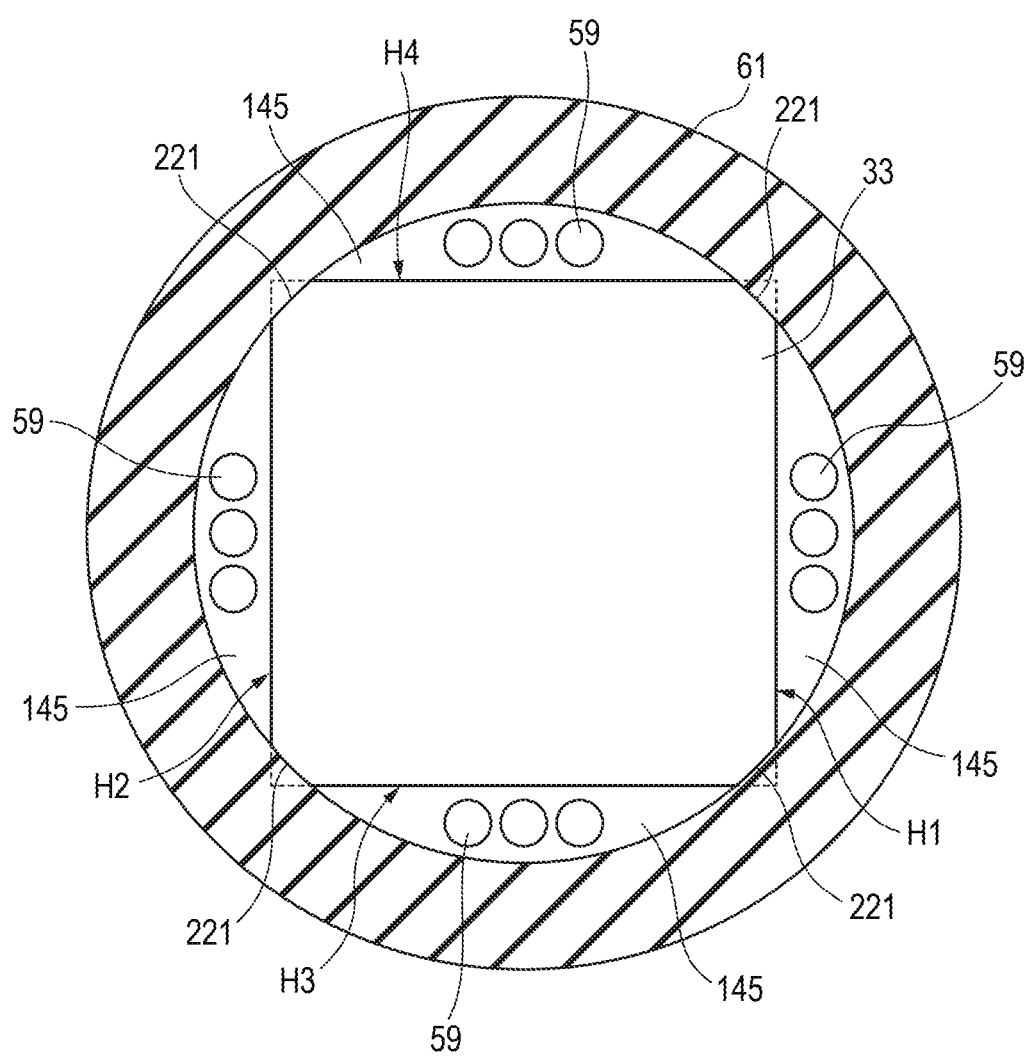
FIG. 41 is a front sectional view including a sensor of the endoscope illustrated in FIG. 39.
Figure 42:
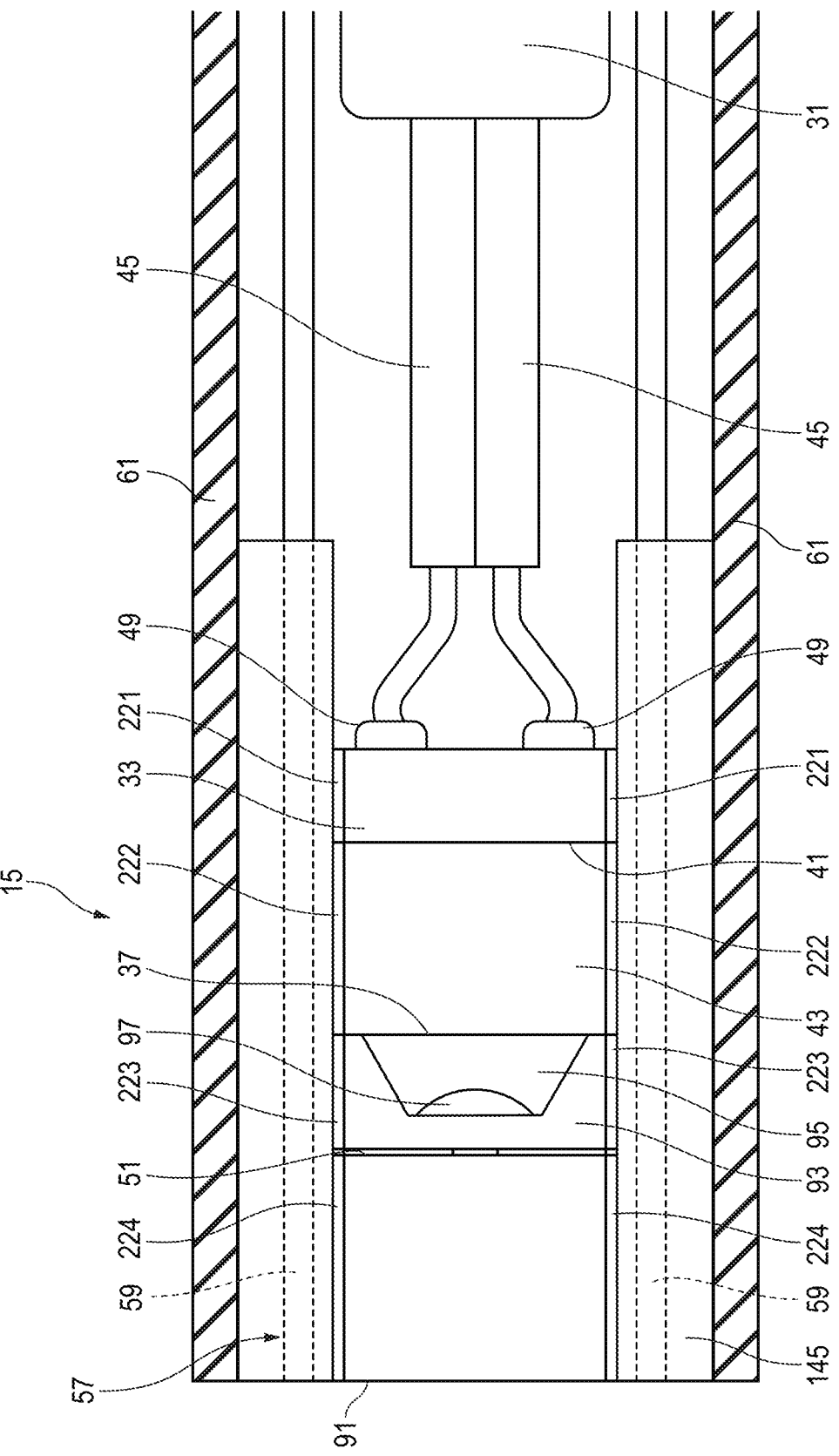
FIG. 42 is a plan sectional view of the endoscope illustrated in FIG. 39.

FIG. 39 is a perspective view of the tip portion 15 of the endoscope 11 according to the present embodiment in which the imaging element 33 and the sheath 61 are substantially in contact with each other and the four corners of the imaging element 33 are chamfered. FIG. 40 is a perspective view in which the sheath 61 of the endoscope 11 illustrated in FIG. 39 is seen through. FIG. 41 is a front sectional view including the imaging element 33 of the endoscope 11 illustrated in FIG. 39. FIG. 42 is a plan sectional view of the endoscope 11 illustrated in FIG. 39.

Description of the configuration of the present configuration example that is similar to those of the configuration examples described above may be omitted or provided in a simplified manner.

In FIGS. 39 to 42, the four corners of the imaging element 33 are chamfered and the chamfered corners are illustrated as cut surfaces 221. Cut surfaces at the four corners of the element cover glass 43 are illustrated as cut surfaces 222. Cut surfaces at the four corners of the lens 93 are illustrated as cut surfaces 223. Cut surfaces at the four corners of the objective cover glass 91 are illustrated as cut surfaces 224.

In comparison to the sixteenth configuration example, the endoscope 11 according to the seventeenth configuration example has a shape in which at least some of the four corners of the quadrangular shape of at least the imaging element 33 are cut. Some of the four corners member that the four angles of the quadrangular shape may be chamfered without exception or the number of such chamfered angles may be three or less. Examples of the way in which the chamfering is conducted include the method according to the ninth configuration example. In other words, the imaging element 33 may have an octagonal outer shape, a dodecagonal outer shape, or a polygonal outer shape with at least 13 sides.

The diagonal length of the imaging element 33 can be reduced in the endoscope 11 according to the seventeenth configuration example when at least some of the four corners of the imaging element 33 that has a quadrangular sectional shape in the front view are cut. Because the imaging element 33 and the sheath 61 are substantially in contact with each other, the diagonal length of the quadrangular sectional shape in the front view of the imaging element 33 and the length of the diameter of the circular section of the sheath 61 in the front view are substantially equal to each other. Accordingly, the length of the diameter of the sheath 61 that is placed on the outermost side of the endoscope 11 can be reduced, and thus the diameter of the endoscope 11 can be more reduced than in a case where the four corners of the imaging element 33 are not chamfered.

The lens 93 in the endoscope 11 may also have a shape in which at least some of the four corners of its quadrangular sectional shape in a front view are cut. Some of the four corners member that the four angles of the quadrangular shape may be chamfered without exception or the number of such chamfered angles may be three or less. Examples of the way in which the chamfering is conducted include a method similar to that by which the imaging element 33 is chamfered. In other words, the lens 93 may have an octagonal outer shape, a dodecagonal outer shape, or a polygonal outer shape with at least 13 sides.

The imaging element 33 and the lens 93 may be chamfered by different methods, too. The imaging element 33 and the lens 93 may have different outer shapes as a result.

The diagonal length of the lens 93 can be reduced in the endoscope 11 when at least some of the four corners of the lens 93 that has a quadrangular sectional shape in the front view are cut. In a case where the lens 93 and the sheath 61 are substantially in contact with each other, the diagonal length of the quadrangular sectional shape in the front view of the lens 93 and the length of the diameter of the circular section of the sheath 61 in the front view are substantially equal to each other. Accordingly, the length of the diameter of the sheath 61 that is placed on the outermost side of the endoscope 11 can be reduced, and thus the diameter of the endoscope 11 can be more reduced than in a case where the four corners of the lens 93 are not chamfered.

In general, it is more difficult to reduce the size of the imaging element 33 than to reduce the size of the lens 93. Accordingly, the diagonal length of the imaging element 33 becoming a bottleneck in reducing the diameter of the tip portion 15 of the endoscope 11 is observed in a case where the diameter of the endoscope 11 is minimized. Accordingly, the imaging element 33 may be chamfered without the lens 93 being chamfered in a case where the area of the quadrangular sectional shape in the front view of the imaging element 33 (non-chamfered area) exceeds the area of the quadrangular sectional shape in the front view of the lens 93. In this case, a reduction in the diameter of the tip portion 15 of the endoscope 11 is pursued by the diagonal length of the quadrangular sectional shape in the front view of the lens 93 and the length of the diameter of the sheath 61 being allowed to become substantially equal to each other. In addition, chamfering may also be performed on both the imaging element 33 and the lens 93 in the case where the area of the quadrangular sectional shape in the front view of the imaging element 33 exceeds the area of the quadrangular sectional shape in the front view of the lens 93. Then, the diameter of the tip portion 15 of the endoscope 11 can be more reduced than in a case where the imaging element 33 is chamfered without the lens 93 being chamfered.

The area of the quadrangular sectional shape in the front view of the imaging element 33 may fall short of the area of the quadrangular sectional shape in the front view of the lens 93 as well. In this case, the lens 93 may be chamfered without the imaging element 33 being chamfered. In this case, a reduction in the diameter of the tip portion 15 of the endoscope 11 is pursued by the diagonal length of the quadrangular sectional shape in the front view of the imaging element 33 and the length of the diameter of the sheath 61 being allowed to become substantially equal to each other. In addition, chamfering may also be performed on both the imaging element 33 and the lens 93 in the case where the area of the imaging element 33 falls short of the area of the lens 93. Then, the diameter of the tip portion 15 of the endoscope 11 can be more reduced than in a case where the lens 93 is chamfered without the imaging element 33 being chamfered.

The element cover glass 43 and an objective cover glass 44 may be chamfered as is the case with the imaging element 33 and the lens 93. Exemplified in FIG. 42 is a state where the four corners of the imaging element 33, the element cover glass 43, the lens 93, and the objective cover glass 91 are chamfered by being cut in the form of the cut surfaces 221, 222, 223, and 224, respectively.

The number of the optical fibers 59 that are placed in parallel (in a row herein) along each of two parallel sides of the imaging element 33 is six in FIG. 40. The number of the optical fibers 59 that are placed in parallel (in a row herein) along each of the four sides of the imaging element 33 is three in FIG. 41. In the present configuration example, any number can be the number of sides along which the optical fiber 59 is arranged and the number of the optical fibers 59 arranged along each side.

The shapes of the transmission cable 31 in the plan sectional view illustrated in FIG. 42 including the chamfered imaging element 33 and in the plan sectional view illustrated in FIG. 29 including the non-chamfered imaging element 33 differ from each other, but any of the configurations can be adopted. In other words, the transmission cable 31 illustrated in FIG. 29 may be described in FIG. 42 and the transmission cable 31 illustrated in FIG. 42 may be described in FIG. 29.

The mold resin 145 extends from the tip of the tip portion 15 up to the sectional position of the imaging element 33 in FIG. 29 whereas the mold resin 145 extends from the tip of the tip portion 15 up to the sectional position of the electric wire 45 beyond the imaging element 33 in FIG. 42. Any of the configurations can be adopted. In other words, the mold resin 145 illustrated in FIG. 29 may be described in FIG. 42 and the mold resin 145 illustrated in FIG. 42 may be described in FIG. 29.

Eighteenth Configuration Example

As illustrated in FIGS. 37 and 40, for example, the endoscope 11 according to the eighteenth configuration example is provided with a single lens (such as the lens 93) that has a substantially quadrangular outer shape (such as a square shape, a rectangular shape, and a chamfered quadrangular shape) in the direction perpendicular to the optical axis or the lens center. The endoscope 11 is provided with the imaging element 33 that has a substantially quadrangular outer shape (such as a square shape and a rectangular shape) in the direction perpendicular to the lens center with the length of its one side being equal to the length of one side of the single lens. The endoscope 11 is provided with the element cover glass 43 covering the imaging surface 41 of the imaging element 33 and having the same outer shape as the imaging element 33 in the direction perpendicular to the lens center. The endoscope 11 is provided with the sheath 61 placed coaxially with respect to the lens center, surrounding the outside surfaces of the single lens, the element cover glass 43, and the imaging element 33, and having a circular outer shape. The sheath 61 is substantially in contact with the imaging element 33. In addition, the endoscope 11 is provided with the lighting member (such as the optical fibers 59) placed along the lens center and inserted between the respective outside surfaces of the single lens and the imaging element 33 and the inner peripheral surface of the sheath 61. The number of the lighting member is at least two. The plurality of lighting member is placed in parallel (in a row, for example) along at least one side of the single lens or the imaging element 33 (sides H1 to H4, for example).

A holder that holds the lens 93 and the imaging element 33 can be omitted from the endoscope 11 according to the eighteenth configuration example. Accordingly, a space that is equivalent to the holder can be removed. In addition, since the imaging element 33 and the sheath 61 are substantially in contact with each other with the four corners of the imaging element 33 chamfered or not chamfered, the diagonal length of the quadrangular sectional shape in the front view of the imaging element 33 and the length of the diameter of the sheath 61 are substantially equal to each other, which contributes to a reduction in the diameter of the tip portion 15 of the endoscope 11.

This leads to member placement density improvement in the tip portion 15 of the endoscope 11 as the space resulting from the difference in shape between the part of the sheath 61 that has a circular section in the front view and the parts of the lens 93 and the imaging element 33 that have a quadrangular sectional shape in the front view can be used for the placement of the light guide 57 (the plurality of optical fibers 59 herein). As a result, a useless space in the tip portion 15 can be suppressed in the endoscope 11.

In the endoscope 11, the plurality of optical fibers 59 is not placed in an arbitrary way in the space resulting from the shape difference. Instead, the plurality of optical fibers 59 are arranged in parallel along at least one side of the lens 93 or the imaging element 33. Accordingly, the number of the optical fibers 59 that can be arranged in the space of the same size is larger than in a case where the plurality of optical fibers 59 is placed in an arbitrary way. As a result, the number of illuminations increases, which leads to an increase in the brightness of lighting.

As described above, both a reduction in the size of the endoscope 11 and lighting efficiency improvement can be achieved from the endoscope 11.

Nineteenth Configuration Example

In the endoscope 11 according to the nineteenth configuration example, the plurality of lighting member (such as the optical fibers 59) are placed in parallel along each of at least two sides of the single lens (such as the lens 93) or the imaging element 33 and are placed in point symmetry with respect to the lens center.

In FIGS. 38 and 41, the number of the optical fibers 59 that are placed in parallel (in a row herein) along each of the four sides H1 to H4 of the quadrangular sectional shape in the front view of the imaging element 33 is three. Referring to FIGS. 38 and 41, it can be appreciated that the optical fibers 59 are placed at the respective positions of point symmetry with respect to the center of the imaging element 33. The center of the imaging element 33 corresponds to the lens center in the cross section perpendicular to the optical axis or the lens center.

The optical fibers 59 in the endoscope 11 according to the nineteenth configuration example are equidistantly placed across the center of the imaging element 33, and thus the object of observation can be illuminated in a uniform manner. Accordingly, uneven illumination by the endoscope 11 can be reduced, the quantity of the light that is obtained from the subject can be equalized in the respective pixels of the imaging element 33, and the pixels can be given a uniform image quality. As a result, the quality of the image of the subject obtained with the endoscope 11 is improved.

Any number can be the number of the optical fibers 59 according to the present configuration example. In addition, the optical fibers can be placed in parallel along any of the sides of the quadrangular shape. The parallel placement may be performed in a row with respect to at least one side of the imaging element 33. As long as a space for placement is allowed, the parallel placement may be performed in two or more rows.

Figure 43:
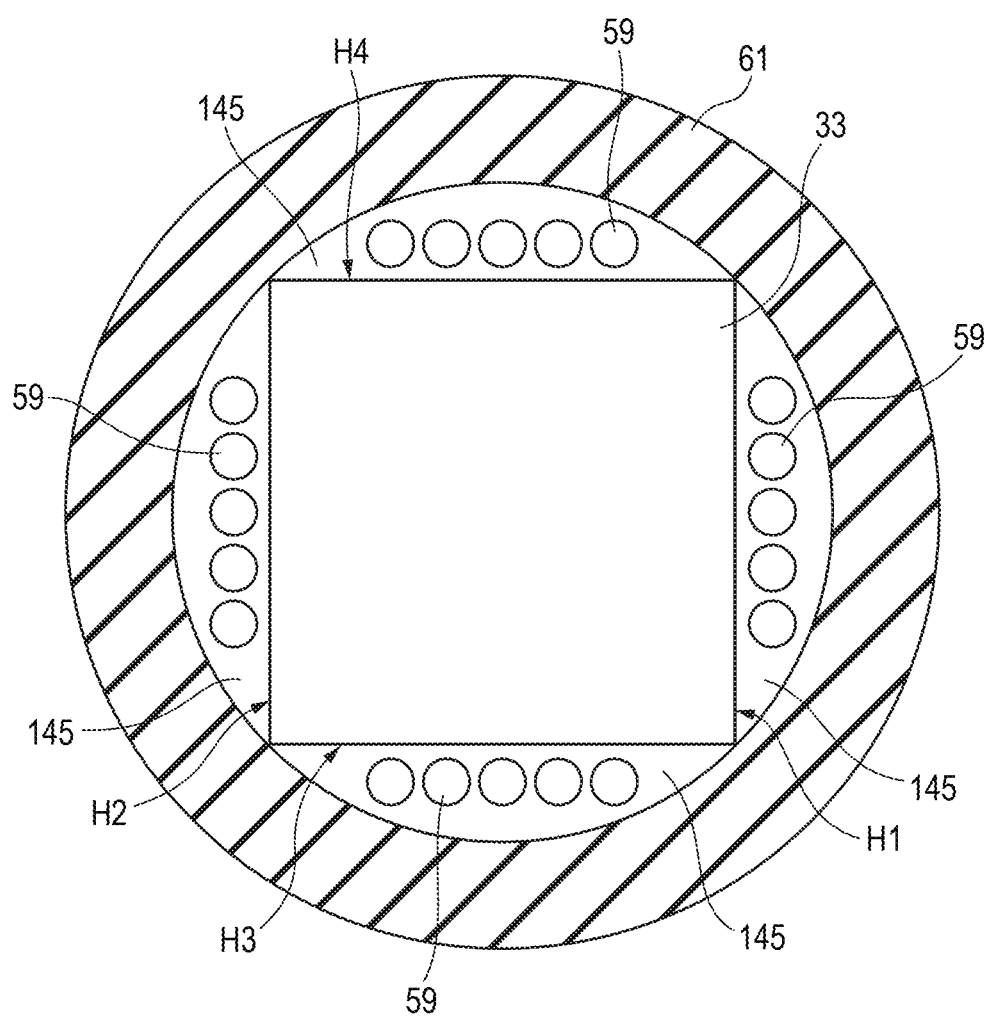
FIG. 43 is a front sectional view in which a plurality of the optical fibers is arranged along four sides of the imaging element of the endoscope according to the present embodiment.

FIG. 43 is a drawing illustrating a first modification example of the arrangement of the plurality of optical fibers 59. The number of the optical fibers 59 that are placed in parallel (in a row herein) along each of the four sides H1 to H4 of the quadrangular sectional shape in the front view of the imaging element 33 is five in FIG. 43.

Figure 44:
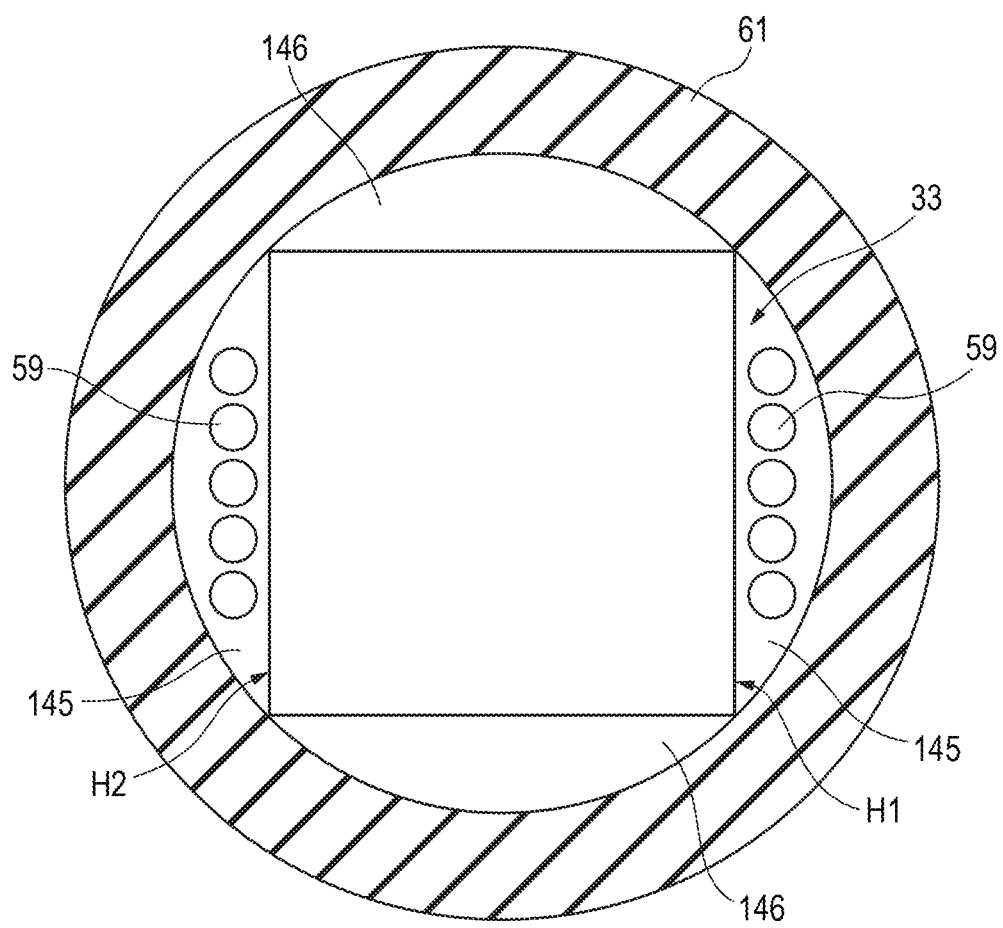
FIG. 44 is a front sectional view in which a plurality of the optical fibers is arranged along two sides of the imaging element of the endoscope according to the present embodiment.

FIG. 44 is a drawing illustrating a second modification example of the arrangement of the plurality of optical fibers 59. The number of the optical fibers 59 that are placed in parallel (in a row herein) along the two sides H1 and H2 of the quadrangular sectional shape in the front view of the imaging element 33 is five in FIG. 44. The two sides H1 and H2 in FIG. 44 are sides at positions of point symmetry with respect to the center of the imaging element 33. The respective optical fibers 59 are arranged in point symmetry with respect to the center of the imaging element 33.

Twentieth Configuration Example

Figure 45:
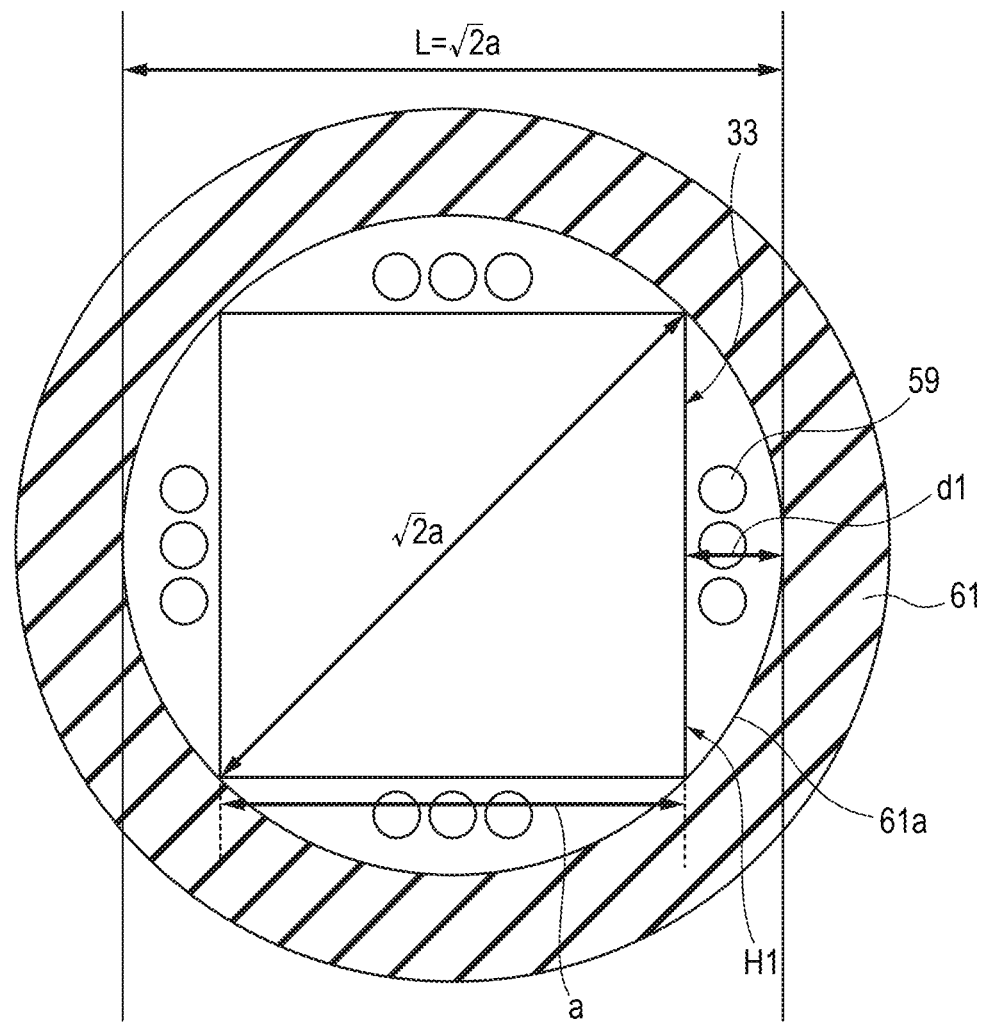
FIG. 45 is a diagram for showing the length of the diameter of the optical fiber of the endoscope according to the present embodiment.
Figure 46:
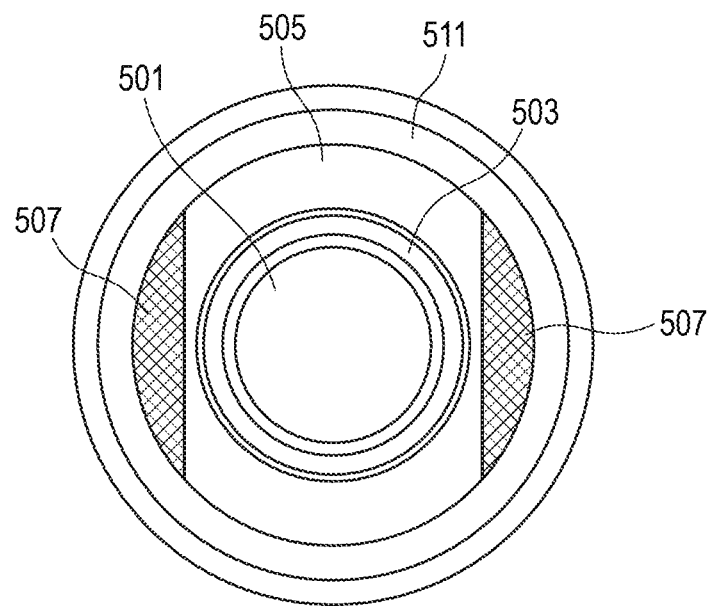
FIG. 46 is a front view of a tip portion of a small-diameter electronic endoscope according to the related art.
Figure 47:
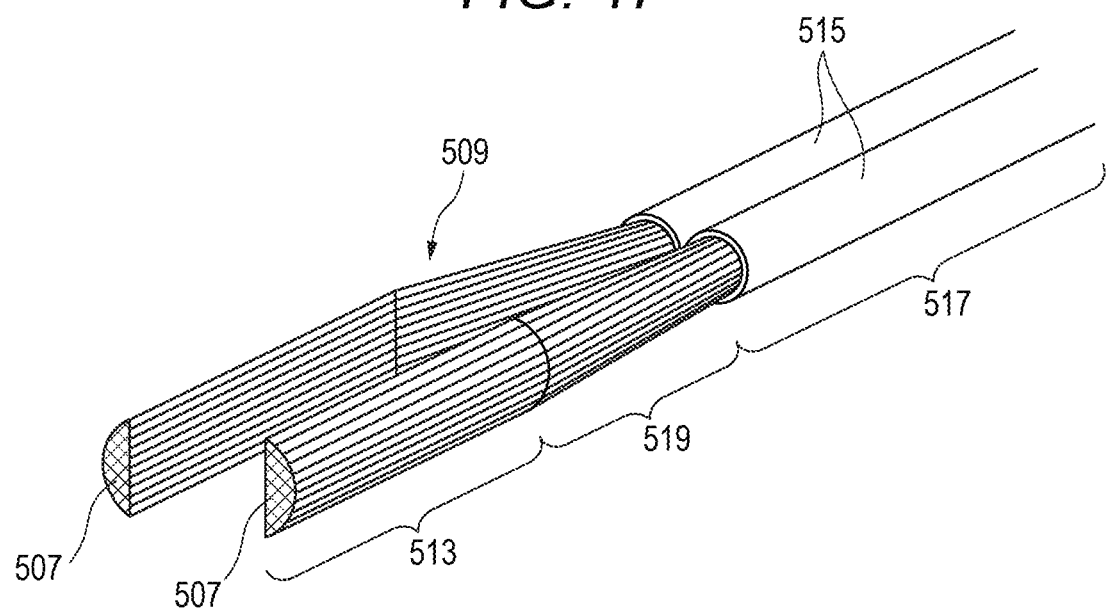
FIG. 47 is a perspective view of a light guide fiber bundle unit in the tip portion of the small-diameter electronic endoscope.

FIG. 45 is a diagram for showing an example of the length of the diameter of the optical fiber 59 of the endoscope 11 according to the present embodiment.

The imaging element 33 in the endoscope 11 according to the twentieth configuration example has a square outer shape in the direction perpendicular to the lens center. The length of the diameter of the lighting member (such as the optical fiber 59) is 20% or less of the length of one side of the imaging element 33.

In the endoscope 11 according to the twentieth configuration example, accommodating in a space sp resulting from the difference in shape between the part of the sheath 61 that has a circular section in the front view and the part of the lens 93 that has a quadrangular sectional shape in the front view can be conducted with consideration given to the length of the diameter of the optical fiber 59.

Assuming that the length of one side of the imaging element 33 is "a", the imaging element 33 has a diagonal length of "√2a" in FIG. 45. √A is the square root of Value A. Accordingly, √2 is the square root of Value 2. According to FIG. 45, the four corners of the square sectional shape in the front view of the imaging element 33 are substantially in contact with an inner peripheral surface 61a of the sheath 61. Since the sheath 61 has a circular outer shape, the length of the diameter of the sheath 61 is "√2a".

In the cross section illustrated in FIG. 45, the space sp is formed between the sheath 61 having a circular cross section in the front view and the imaging element 33 having a square sectional shape in the front view, which are substantially in contact with each other. In the space sp, the maximum length of the diameter of the optical fiber 59 is equivalent to a distance d1, which is the distance from the inner peripheral surface 61a of the sheath 61 to the side H1 of the imaging element 33 orthogonal to the radial direction of the circular cross section in the front view of the sheath 61. The distance d1 is represented by the following (Equation 1).

$$d1=(\sqrt{2}a-a)/2 \approx 0.2a \quad \text{(Equation 1)}$$

In other words, the diameter of the optical fiber 59 that can be inserted into the space sp is 20% or less of the length a of one side of the imaging element 33.

The length a of one side of the imaging element 33 is, for example, 500 μm. The length of the diameter of the optical fiber 59 is, for example, 50 μm. In this case, the diameter of the optical fiber 59 becomes 10% of one side of the imaging element 33 and satisfies (Equation 1) related to the maximum length d1 of the diameter of the optical fiber 59.

The embodiment has been described above with reference to the accompanying drawings. It is a matter of course that the present invention is not limited to the example. It is obviously conceivable that various modified or correction examples are available within the scope of the claims depending on those skilled in the art and it is clearly understood that such examples naturally pertain to the technical scope of the present invention. Elements constituting the embodiment may be appropriately combined with each other in any form without departing from the purpose of the present invention.

The present disclosure is effective as, for example, a small-diameter endoscope with which stray light from lighting member can be prevented with high-strength fixing of a lens and an imaging element facilitated and size reduction ensured by space efficiency (that is, member placement density) improvement (that is, suppression of a useless space) being allowed in an insertion tip surface.

What is claimed is:

1. An endoscope comprising:
   a lens that has a quadrangular outer shape in a direction perpendicular to a center axis of the lens;
   an imaging element that has a quadrangular outer shape in the direction perpendicular to the center axis;
   an element cover glass configured to cover an imaging surface of the imaging element;
   a lighting member that is disposed outside at least one side of the lens and extends along the center axis;
   a light-shielding member that is disposed between the lens and the lighting member; and
   an objective cover glass, wherein the element cover glass is disposed between the objective cover glass and the imaging element,
   wherein the light-shielding member has a first side portion disposed on a first side of the lens and a second side portion disposed on a second side of the lens,
   wherein both of the first side portion and the second side portion have a length equal to or greater than a length from an insertion tip surface in a tip portion of the endoscope to the imaging surface of the imaging element,
   wherein the lens and the imaging element are disposed between a first end and a second end of the first side portion of the light-shielding member when viewed from the direction perpendicular to the center axis,
   wherein the lens and the imaging element are disposed between a first end and a second end of the second side portion of the light-shielding member when viewed from the direction perpendicular to the center axis,
   wherein the light-shielding member includes a front portion and a back portion that is adjacent to the front portion,
   wherein the back portion of the light-shielding member has a quadrangular outer shape,
   wherein an aperture having a quadrangular outer shape is formed in the front portion of the light-shielding member, and the objective cover glass is disposed within the aperture, and
   wherein an outer diameter of the back portion of the light-shielding member is less than an outer diameter of the front portion of the light-shielding member.

2. The endoscope according to claim 1,
   wherein the light-shielding member is a holder coaxially accommodating the lens and the imaging element; and
   wherein a notch is provided on an outer peripheral surface of the holder and extends in a direction along the center axis to place the lighting member thereon.

3. The endoscope according to claim 1,
   wherein the light-shielding member is a holder coaxially accommodating the lens and the imaging element; and
   wherein a through-hole is provided between an outer peripheral surface of the holder and one side of the lens and extends in a direction along the center axis to place the lighting member therein.

4. The endoscope according to claim 1,
   wherein the light-shielding member is comprised of resin and configured to cover an outside surface of the lighting member.

5. The endoscope according to claim 1,
   wherein the light-shielding member is a pipe into which the lighting member is inserted.

6. The endoscope according to claim 1, wherein the light-shielding member has an end surface including both the first end of the first side portion and the first end of the second side portion.

7. The endoscope according to claim 1, wherein the first side portion of the light-shielding member is separated from the second side portion of the light-shielding member.

8. The endoscope according to claim 1, wherein the front portion includes the first side portion and the second side portion.

\* \* \* \* \*